United States Patent
Redondo Moya et al.

(10) Patent No.: US 12,163,161 B2
(45) Date of Patent: *Dec. 10, 2024

(54) IN VITRO METHOD FOR IDENTIFYING THORACIC AORTIC ANEURYSMS (TAA) IN A SUBJECT

(71) Applicants: CENTRO NACIONAL DE INVESTIGACIONES CARDIOVASCULARES CARLOS III (F.S.P.), Madrid (ES); CONSEJO SUPERIOR DE INVESTIGACIONES CIENTÍFICAS, Madrid (ES); UNIVERSIDAD AUTÓNOMA DE MADRID, Madrid (ES)

(72) Inventors: Juan Miguel Redondo Moya, Madrid (ES); Nerea Méndez-Barbero, Madrid (ES); Jorge Oller Pedrosa, Madrid (ES); Miguel Ramón Campanero Garcia, Madrid (ES)

(73) Assignees: CENTRO NACIONAL DE INVESTIGACIONES CARDIOVASCULARES CARLOS III (F.S.P.), Madrid (ES); CONSEJO SUPERIOR DE INVESTIGACIONES CIENTÍFICAS, Madrid (ES); UNIVERSIDAD AUTÓNOMA DE MADRID, Madrid (ES)

( * ) Notice: Subject to any disclaimer, the term of this patent is extended or adjusted under 35 U.S.C. 154(b) by 1002 days.

This patent is subject to a terminal disclaimer.

(21) Appl. No.: 17/122,962

(22) Filed: Dec. 15, 2020

(65) Prior Publication Data
US 2021/0363501 A1 Nov. 25, 2021

Related U.S. Application Data

(63) Continuation of application No. 16/083,165, filed as application No. PCT/EP2016/082925 on Dec. 30, 2016, now Pat. No. 10,907,135.

(30) Foreign Application Priority Data

Mar. 7, 2016 (EP) ..................................... 16382103

(51) Int. Cl.
G01N 33/68 (2006.01)
C12N 9/02 (2006.01)

(52) U.S. Cl.
CPC .... *C12N 9/0075* (2013.01); *C12Y 114/13039* (2013.01); *G01N 33/6893* (2013.01); *G01N 2333/96419* (2013.01); *G01N 2800/329* (2013.01)

(58) Field of Classification Search
CPC .......... C12N 9/0075; C12Y 114/13099; G01N 33/6893
USPC ...................................................... 435/69.1
See application file for complete search history.

(56) References Cited

U.S. PATENT DOCUMENTS

| | | | |
|---|---|---|---|
| 10,683,493 | B2 | 6/2020 | Saborit et al. |
| 2017/0184576 | A1 | 6/2017 | Esteve Tintóet al. |
| 2018/0328838 | A1 | 11/2018 | Oliva Ramírez et al. |
| 2018/0355427 | A1 | 12/2018 | Martín Fernández et al. |
| 2019/0037900 | A1 | 2/2019 | Torres Olivares et al. |
| 2020/0270310 | A1 | 8/2020 | Ibáñez De Cáceres et al. |
| 2020/0282897 | A1 | 9/2020 | Simón et al. |
| 2020/0345701 | A1 | 11/2020 | López Serrano et al. |
| 2021/0077609 | A1 | 3/2021 | Grilló Dolset et al. |
| 2021/0181189 | A1 | 6/2021 | Esteve Tintóet al. |
| 2021/0186989 | A1 | 6/2021 | Sancho Madrid et al. |

FOREIGN PATENT DOCUMENTS

| | | |
|---|---|---|
| WO | 03/026668 A1 | 4/2003 |
| WO | 2014/004889 A2 | 1/2014 |

OTHER PUBLICATIONS

Alderton et al., "Nitric oxide synthases: structure, function and inhibition," *Biochem. J.* 357:593-615, 2001.
Armstrong et al., "Suppression of Experimental Aortic Aneurysms: Comparison of Inducible Nitric Oxide Synthase and Cyclooxygenase Inhibitors," *Ann Vasc Surg* 19:248-257, 2005.
Cardenas et al., "An HDAC9-MALAT1-BRG1 complex mediates smooth muscle dysfunction in thoracic aortic aneurysm," *Nature Communications* DOI: 10.1038/s41467-018-3394-7, 2018, 14 pages.
Cikach et al., "Massive aggrecan and versican accumulation in thoracic aortic aneurysm and dissection," *JCI Insight.* 3(5):e97167, 2018.
Danyi et al., "Medical Therapy of Thoracic Aortic Aneurysms, Are We There Yet?" *Circulation* 124:1469-1476, 2011.
Elefteriades et al., "Thoracic Aortic Aneurysm: Clinically Pertinent Controversies and Uncertainties," *Journal of the American College of Cardiology* 55(9):841-857, 2010.
Gao et al., "A disintegrin and metalloproteinase with thrombospondin motif 1 (ADAMTS1) expression increases in acute aortic dissection," *Sci China Life Sci* 59:59-67, 2016.
Goyal, et al., "The Genetics of Aortopathies in Clinical Cardiology," *Clinical Medicine Insights: Cardiology* 11:1-11, 2017.

(Continued)

*Primary Examiner* — Yevgeny Valenrod
(74) *Attorney, Agent, or Firm* — Seed IP Law Group LLP

(57) ABSTRACT

The present invention refers to an In vitro method for screening for subjects at risk of developing thoracic aortic aneurysm (TAA) or a disease causing TAA comprising: (a) measuring the expression pattern or level of at least A Disintegrin And Metalloproteinase with Thrombospondin Motifs 1 (ADAMTS1) obtained from an isolated biological sample of the subjects to be screened; and (b) comparing said expression pattern or level of at least ADAMTS1 of the subjects to be screened with an already established expression pattern or level, wherein reduced expression of at least ADAMTS1 is indicative of a thoracic aortic aneurysm (TAA).

12 Claims, 38 Drawing Sheets
Specification includes a Sequence Listing.

(56) References Cited

OTHER PUBLICATIONS

Habashi et al., "Losartan, an ATI Antagonist, Prevents Aortic Aneurysm in a Mouse Model of Marfan Syndrome," *Science* 312(5770):117-121, 2006.
Habashi et al., "Oxytocin antagonism prevents pregnancy-associated aortic dissection in a mouse model of Marfan syndrome," *Sci. Transl. Med.* 11, 2019, 11 pages.
Hibender et al., "Resveratrol Inhibits Aortic Root Dilatation in the Fbn1CI Marfan Mouse Model," *Arterioscler Thromb Vasc Biol.* 36:1618-1626, 2016.
Holm et al., "Noncanonical TGFβ Signaling Contributes to Aortic Aneurysm Progression in Marfan Syndrome Mice," *Science* 332(6027):358-361, 2011.
Humphrey, "Possible Mechanical Roles of Glycosaminoglycans in Thoracic Aortic Dissection and Associations with Dysregulated Transforming Growth Factor-β," *J. Vasc. Res.* 50:1-10, 2013.
Johanning et al., "Inhibition of inducible nitric oxide synthase limits nitric oxide production and experimental aneurysm expansion," *J Vasc Surg* 33:579-86, 2001.
Johanning et al., "Nitric Oxide in Experimental Aneurysm Formation: Early Events and Consequences of Nitric Oxide Inhibition," *Annals of Vascular Surgery* 16(1):65-72, 2002.
Judge et al., "Evidence for a critical contribution of haploinsufficiency in the complex pathogenesis of Marfan syndrome," *The Journal of Clinical Investigation* 144(2):172-181, 2004.
Li et al., "Tgfbr2 disruption in postnatal smooth muscle impairs aortic wall homeostasis," *The Journal of Clinical Investigation* 124(2):755-767, 2014.
Liao et al., "Suppression of experimental abdominal aortic aneurysms in the rat by treatment with angiotensin-converting enzyme inhibitors," *J Vasc Surg* 33:1057-1064, 2001.
Milewicz et al., "Altered Smooth Muscle Cell Force Generation as a Driver of Thoracic Aortic Aneurysms and Dissections," *Arterioscler Thromb Vasc Biol.* 37:26-34, 2017.
Ramirez-Marrero et al., "Marfan Syndrome—Advances in Diagnosis and Management," *Aneurysm*, 26 pages, 2012.
Ren et al., "ADAMTS-1 and ADAMTS-4 Levels Are Elevated in Thoracic Aortic Aneurysms and Dissections," *Ann Thorac Surg* 95:570-578, 2013.
Saratzis et al., "The genetic basis for aortic aneurysmal disease," *Heart* 100:916-922, 2014.
Shen et al., "Unfolding the Story of Proteoglycan Accumulation in Thoracic Aortic Aneurysm and Dissection," *Arterioscler Thromb Vasc Biol.* 39:1899-1901, 2019.
Tan et al., "SMAD3 Deficiency Promotes Inflammatory Aortic Aneurysms in Angiotensin II-Infused Mice via Activation of iNOS," J AM Heart Assoc. doi:10.1161, 2013, 28 pages.
Víteček et al., "Arginine-Based Inhibitors of Nitric Oxide Synthase: Therapeutic Potemtial and Challenges," *Mediators of Inflammation* 2012, 22 pages, 2012.
Alderton et al., "GW274150 and GW273629 are potent and highly selective inhibitors of inducible nitric oxide synthase in vitro and in vivo," *British Journal of Pharmacology* 145:301-312, 2005.
Chung et al., "Endothelial dysfunction and compromised eNOS/Akt signaling in the thoracic aorta during the progression of Marfan syndrome," *British Journal of Pharmacology* 150:1075-1083, 2007.
Yang et al., "Vasomotor dysfunction in the thoracic aorta of Marfan syndrome is associated with accumulation of oxidative stress," *Vascular Pharmacology* 52:37-45, 2010.

SEQUENCE LISTING

<160> NUMBER OF SEQ ID NOS: 26

<210> SEQ ID NO 1
<211> LENGTH: 20
<212> TYPE: DNA
<213> ORGANISM: Artificial Sequence

```
<220> FEATURE:
<223> OTHER INFORMATION: Adamts1 primer

<400> SEQUENCE: 1
acactggcgg ttggcatcgt                                                   20

<210> SEQ ID NO 2
<211> LENGTH: 20
<212> TYPE: DNA
<213> ORGANISM: Artificial Sequence
<220> FEATURE:
<223> OTHER INFORMATION: Adamts1 primer

<400> SEQUENCE: 2
gccagccctg gtcaccttgc                                                   20

<210> SEQ ID NO 3
<211> LENGTH: 21
<212> TYPE: DNA
<213> ORGANISM: Artificial Sequence
<220> FEATURE:
<223> OTHER INFORMATION: Nos2 primer

<400> SEQUENCE: 3
cagctgggct gtacaaacct t                                                 21

<210> SEQ ID NO 4
<211> LENGTH: 21
<212> TYPE: DNA
<213> ORGANISM: Artificial Sequence
<220> FEATURE:
<223> OTHER INFORMATION: Nos2 primer

<400> SEQUENCE: 4
cattggaagt gaagcgtttc g                                                 21

<210> SEQ ID NO 5
<211> LENGTH: 25
<212> TYPE: DNA
<213> ORGANISM: Artificial Sequence
<220> FEATURE:
<223> OTHER INFORMATION: Adamts1 mice primer

<400> SEQUENCE: 5
gccatcgggg tcagcttttc aaatg                                             25

<210> SEQ ID NO 6
<211> LENGTH: 25
<212> TYPE: DNA
<213> ORGANISM: Artificial Sequence
<220> FEATURE:
<223> OTHER INFORMATION: Adamts1 mice primer

<400> SEQUENCE: 6
gggccagctc attcctccca ctcat                                             25

<210> SEQ ID NO 7
<211> LENGTH: 25
<212> TYPE: DNA
<213> ORGANISM: Artificial Sequence
<220> FEATURE:
<223> OTHER INFORMATION: Adamts1 mice primer

<400> SEQUENCE: 7
ggttgtagtt tcgcgctgag ttttg                                             25
```

```
<210> SEQ ID NO 8
<211> LENGTH: 20
<212> TYPE: DNA
<213> ORGANISM: Artificial Sequence
<220> FEATURE:
<223> OTHER INFORMATION: Nos2-/- mice primer

<400> SEQUENCE: 8
acatgcagaa tgagtaccgg                                              20

<210> SEQ ID NO 9
<211> LENGTH: 20
<212> TYPE: DNA
<213> ORGANISM: Artificial Sequence
<220> FEATURE:
<223> OTHER INFORMATION: Nos2-/- mice primer

<400> SEQUENCE: 9
tcaacatctc ctggtggaac                                              20

<210> SEQ ID NO 10
<211> LENGTH: 20
<212> TYPE: DNA
<213> ORGANISM: Artificial Sequence
<220> FEATURE:
<223> OTHER INFORMATION: Nos2-/- mice primer

<400> SEQUENCE: 10
aatatgcgaa gtggacctcg                                              20

<210> SEQ ID NO 11
<211> LENGTH: 21
<212> TYPE: DNA
<213> ORGANISM: Artificial Sequence
<220> FEATURE:
<223> OTHER INFORMATION: Fbn1C1039G/+ mice primer

<400> SEQUENCE: 11
ctcatcattt ttggccagtt g                                            21

<210> SEQ ID NO 12
<211> LENGTH: 20
<212> TYPE: DNA
<213> ORGANISM: Artificial Sequence
<220> FEATURE:
<223> OTHER INFORMATION: Fbn1C1039G/+ mice primer

<400> SEQUENCE: 12
gcacttgatg cacattcaca                                              20

<210> SEQ ID NO 13
<211> LENGTH: 29
<212> TYPE: DNA
<213> ORGANISM: Artificial Sequence
<220> FEATURE:
<223> OTHER INFORMATION: #siRNA27

<400> SEQUENCE: 13
ggaaagaatc cgcagcttta gtccactca                                    29

<210> SEQ ID NO 14
<211> LENGTH: 29
<212> TYPE: DNA
<213> ORGANISM: Artificial Sequence
<220> FEATURE:
<223> OTHER INFORMATION: #siRNA57
```

```
<400> SEQUENCE: 14
accgccagtg tcagtttaca ttcggagag                                    29

<210> SEQ ID NO 15
<211> LENGTH: 29
<212> TYPE: DNA
<213> ORGANISM: Artificial Sequence
<220> FEATURE:
<223> OTHER INFORMATION: #siRNA69

<400> SEQUENCE: 15
cttccgaatg tgcaaaggaa gtgaagcca                                    29

<210> SEQ ID NO 16
<211> LENGTH: 19
<212> TYPE: DNA
<213> ORGANISM: Artificial Sequence
<220> FEATURE:
<223> OTHER INFORMATION: siCtl

<400> SEQUENCE: 16
gggtgaactc acgtcagaa                                               19

<210> SEQ ID NO 17
<211> LENGTH: 19
<212> TYPE: DNA
<213> ORGANISM: Artificial Sequence
<220> FEATURE:
<223> OTHER INFORMATION: Tgfbeta1 primer

<400> SEQUENCE: 17
cgccatctat gagaaaacc                                               19

<210> SEQ ID NO 18
<211> LENGTH: 17
<212> TYPE: DNA
<213> ORGANISM: Artificial Sequence
<220> FEATURE:
<223> OTHER INFORMATION: Tgfbeta1 primer

<400> SEQUENCE: 18
gtaacgccag gaattgt                                                 17

<210> SEQ ID NO 19
<211> LENGTH: 18
<212> TYPE: DNA
<213> ORGANISM: Artificial Sequence
<220> FEATURE:
<223> OTHER INFORMATION: Ctgf primer

<400> SEQUENCE: 19
gtgccagaac gcacactg                                                18

<210> SEQ ID NO 20
<211> LENGTH: 18
<212> TYPE: DNA
<213> ORGANISM: Artificial Sequence
<220> FEATURE:
<223> OTHER INFORMATION: Ctgf primer

<400> SEQUENCE: 20
ccccggttac actccaaa                                                18

<210> SEQ ID NO 21
```

```
<211> LENGTH: 19
<212> TYPE: DNA
<213> ORGANISM: Artificial Sequence
<220> FEATURE:
<223> OTHER INFORMATION: Col1a1 primer

<400> SEQUENCE: 21
gctcctctta ggggccact                                                  19

<210> SEQ ID NO 22
<211> LENGTH: 19
<212> TYPE: DNA
<213> ORGANISM: Artificial Sequence
<220> FEATURE:
<223> OTHER INFORMATION: Col1a1 primer

<400> SEQUENCE: 22
ccacgtctca ccattgggg                                                  19

<210> SEQ ID NO 23
<211> LENGTH: 25
<212> TYPE: DNA
<213> ORGANISM: Artificial Sequence
<220> FEATURE:
<223> OTHER INFORMATION: Pai-1 primer

<400> SEQUENCE: 23
gccagattta tcatcaatga ctggg                                           25

<210> SEQ ID NO 24
<211> LENGTH: 25
<212> TYPE: DNA
<213> ORGANISM: Artificial Sequence
<220> FEATURE:
<223> OTHER INFORMATION: Pai-1 primer

<400> SEQUENCE: 24
ggagaggtgc acatctttct caaag                                           25

<210> SEQ ID NO 25
<211> LENGTH: 19
<212> TYPE: DNA
<213> ORGANISM: Artificial Sequence
<220> FEATURE:
<223> OTHER INFORMATION: Nos3 primer

<400> SEQUENCE: 25
gtttgtctgc ggcgatgtc                                                  19

<210> SEQ ID NO 26
<211> LENGTH: 17
<212> TYPE: DNA
<213> ORGANISM: Artificial Sequence
<220> FEATURE:
<223> OTHER INFORMATION: Nos3 primer

<400> SEQUENCE: 26
catgccgccc tctgttg                                                    17
```

IN VITRO METHOD FOR IDENTIFYING THORACIC AORTIC ANEURYSMS (TAA) IN A SUBJECT

STATEMENT REGARDING SEQUENCE LISTING

The Sequence Listing associated with this application is provided in text format in lieu of a paper copy, and is hereby incorporated by reference into the specification. The name of the text file containing the Sequence Listing is 210241_401C1_SEQUENCE_LISTING.txt. The text file is 5.1 KB, was created on Dec. 7, 2020, and is being submitted electronically via EFS-Web.

FIELD OF THE INVENTION

The present invention can be included in the field of personalized medicine, wherein specific biomarkers are used for identifying a given disease or disorder and for treating said disease or disorder. In particular, biomarker ADAMTS1 is used in the present invention for identifying human subjects at risk of developing a disease causing thoracic aortic aneurysm (TAA), preferably Marfan syndrome.

BACKGROUND OF THE INVENTION

Aortic aneurysm (AA) is characterized by vascular smooth muscle cell (VSMC) dysfunction and adverse extracellular matrix remodeling that together predispose the vessel wall to dilation, dissection and rupture. AA is often asymptomatic until rupture, causing significant morbidity and mortality. No single gene or locus has been identified as sufficient cause of abdominal AA (AAA), at least in the absence of a more systemic aortopathy. In contrast, thoracic AA (TAA) is strongly associated with familial genetic predisposition and involves gene variants that show high penetrance. Familial TAA and dissections (FTAAD) appear in isolation or together with features of a systemic connective tissue disorder (syndromic FTAAD). Marfan syndrome (MFS) patients and mouse models show skeletal, lung, muscle, and eye abnormalities.

Syndromic and non-syndromic FTAAD is associated with increased TGFβ signaling. TGFβ activation is proposed to cause aortic medial degeneration, a typical histopathologic feature of TAA characterized by an enlarged and weakened medial layer, fibrosis, proteoglycan accumulation, and elastic fiber disorganization and fragmentation. However, it is unclear whether TGFβ activation is cause or consequence of FTAAD.

Since the risk of aortic dissection or rupture escalates with increasing aortic size, the main treatment goals are to limit structural changes to the aortic wall and to slow aneurysm growth. Consistent with a pathogenic role of TGFβ in TAA, neutralizing anti-TGFβ antibodies prevent aortic dilation and inhibit elastic lamellae fragmentation in a mouse model of mild MFS. In the same model, these processes are also inhibited by losartan, an Angiotensin-II (Ang-II) type I receptor (AT1R) antagonist that inhibits TGFβ signaling. However, losartan is less effective in a model of severe MFS, and in randomized clinical trials losartan was no more effective at reducing the rate of aortic root enlargement than the beta-blocker atenolol, and dual therapy with atenolol produced no additional benefit.

Despite the disappointing performance of losartan in clinical trials, it seems clear that Ang-II and AT1R are involved in the development and progression of TAA and AAA in mouse models. Little is known about the mechanisms by which Ang-II promotes aneurysm. However, the authors of the present invention, recently showed that Ang-II and other stimuli associated with vascular remodeling act through AT1R to induce aortic expression of ADAMTS1 (A Disintegrin And Metalloproteinase with Thrombospondin Motifs 1). ADAMTS1, a member of the proteoglycan-degrading ADAMTS metalloproteinase family, is involved in tissue remodeling, ovulation, wound healing and angiogenesis. It is expressed in aortic endothelial and vascular smooth muscle cells (VSMCs) during development and in adulthood and in atherosclerotic lesions. Adamts1 is also expressed in TAA tissue and is active in normal aortic tissue, where it cleaves versican and aggrecan. Adamts1−/− mice have congenital kidney malformations and high perinatal mortality, but no vascular phenotype has been reported.

To investigate the possible role of Adamts1 as a mediator of Ang-II-induced AA, we used Adamts1−/− mice and a model of aortic Adamts1 deficiency based on targeted knockdown. Our data unexpectedly show that Adamts1 deficiency does not inhibit Ang-II-induced aneurysm, and on the contrary, induces a severe aortopathy similar to MFS that affects all aortic segments. ADAMTS1 is weakly expressed in MFS, which indicates a role for Adamts1 deficiency in the aortic phenotype of MFS. Results from the knockdown model shown herein have uncovered a critical role for nitric oxide (NO) in the pathogenesis of aneurysm formation and related to MFS thus providing new treatment methods for TAA and TAA related diseases. In addition, the present invention provides a solution for obtaining useful data for the diagnosis of TAA related diseases as Marfan syndrome or FTAAD.

BRIEF DESCRIPTION OF THE INVENTION

The present invention refers to an in vitro method for screening for subjects at risk of developing thoracic aortic aneurysm (TAA) or a disease causing TAA, comprising:
  (a) measuring the expression pattern or level of at least ADAMTS1 and/or at least the inducible form of the nitric oxide synthase (iNOS) and/or at least the expression pattern of any of the following ADAMTS1 substrates: Aggrecan, versican, tissue factor pathway inhibitor-2 (TFPI-2), semaphorin 3C, nidogen-1, nidogen-2, desmocollin-3, dystroglycan, mac-2, Collagen type I, amphiregulin, TGF-α, heparin-binding EGF, Syndecan 4, versican neoepitopes or aggrecan neoepitopes;
  b) comparing said expression pattern or level of at least ADAMTS1 and/or at least the inducible form of the nitric oxide synthase (iNOS) and/or at least the expression pattern of any of the following ADAMTS1 substrates: Aggrecan, versican, tissue factor pathway inhibitor-2 (TFPI-2), semaphorin 3C, nidogen-1, nidogen-2, desmocollin-3, dystroglycan, mac-2, Collagen type I, amphiregulin, TGF-α, heparin-binding EGF, Syndecan 4, versican neoepitopes or aggrecan neoepitopes, of the subjects to be screened with an already established expression pattern or level,
wherein reduced expression of at least ADAMTS1, Syndecan 4, versican neoepitopes and/or aggrecan neoepitopes and/or overexpression of at least iNOS, Aggrecan, versican, tissue factor pathway inhibitor-2 (TFPI-2), semaphorin 3C, nidogen-1, nidogen-2, desmocollin-3, dystroglycan, mac-2, Collagen type I, amphiregulin, TGF-α and/or heparin-binding EGF, in comparison to an already established expression pattern or level, is indicative of a thoracic aortic aneurysm (TAA) or of a disease causing TAA.

In addition, the present invention further refers to a method for the treatment, prevention or inhibition of a thoracic aortic aneurysm (TAA) in a subject in need of such treatment, prevention or inhibition, comprising administering to said subject an iNOS blocker or a pharmaceutically acceptable salt or prodrug thereof.

Lastly, the present invention refers to screening method for identifying compounds useful for the treatment, prevention or inhibition of a thoracic aortic aneurysm (TAA), comprising the following steps:
1. Identifying a compound or a group of compounds capable of acting as NOS inhibitors, in particular iNOS inhibitors, more particularly as iNOS selective inhibitors; and
2. Determining the usefulness of the selected compounds identified in 1) above for the treatment, prevention or inhibition of a thoracic aortic aneurysm (TAA) or of a disease causing TAA, by the corresponding in vivo or in vitro methods.

Figure 4:
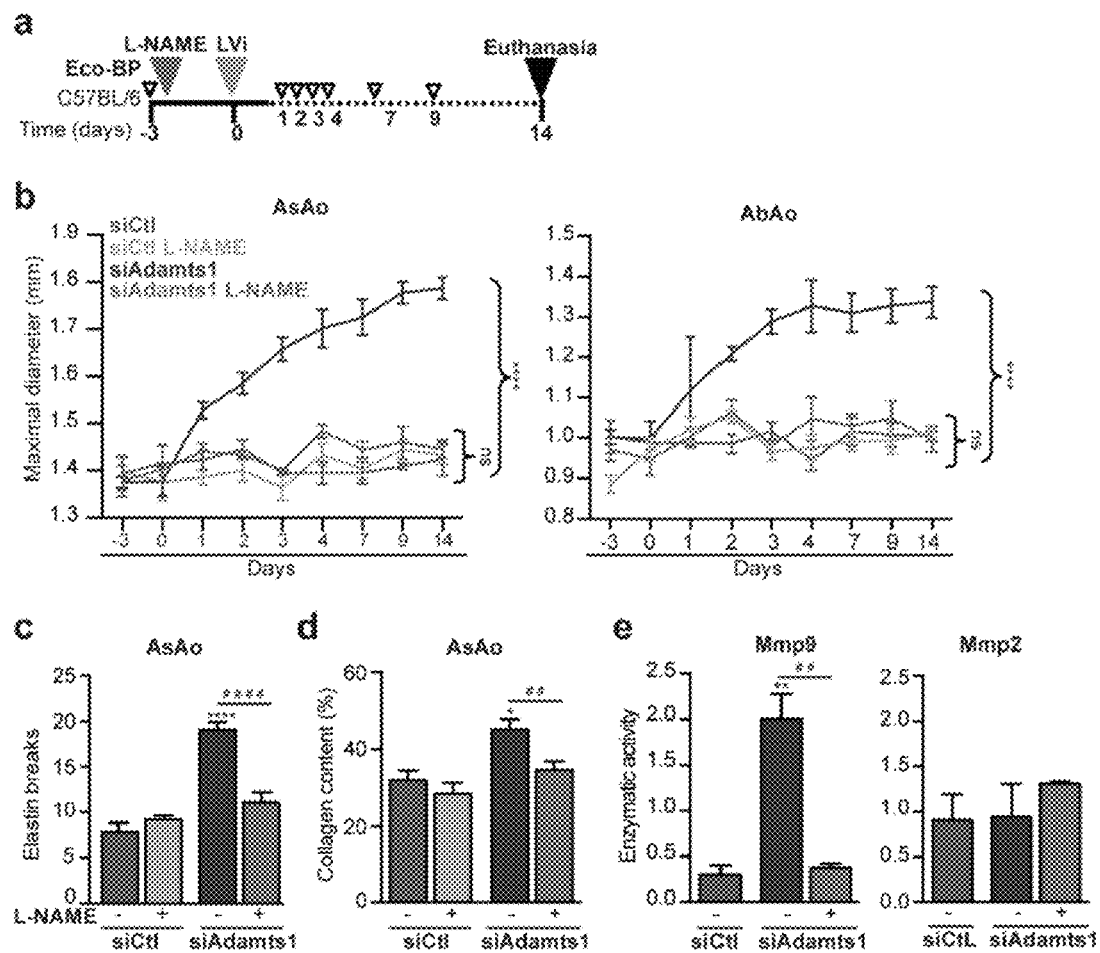
FIG. 4. The aortopathy induced by Adamts1 deficiency is mediated by NO. (a) Experimental design. Eight-week-old C57BL/6 mice were given the NOS inhibitor (L-NAME) in the drinking water, starting 3 days before siCtl or siAdamts1 lentivirus inoculation and continuing for next 14 days. (b) Maximal AsAo and AbAo diameter at the indicated times and end-of-experiment quantification of (c) elastin breaks and (d) collagen content in aortic sections (mean±SEM; n=5 for each group). (e) Quantification of Mmp2 and Mmp9 activity in aortic extracts from siAdamts1-transduced mice treated with L-NAME. (b) Two-way ANOVA of group means and (c-e) one-way ANOVA; *p<0.05, p<0.01, p<0.0001 vs siCtl; ##p<0.01, ####p<0.0001 L-NAME vs Control; ns, non-significant. (f-h) Eight-week-old Adamts1+/+ and Adamts1+/− mice were treated with L-NAME for 21 days. (f) Maximal AsAo and AbAo diameter (mean±SEM) at the indicated time points and end-of-experiment (g) systolic BP, (h) elastin breaks, and (i) collagen content in 12 Adamts1+/+, 13 Adamts1+/+L NAME, 14 Adamts1+/−, and 12 Adamts1+/−L-NAME mice. (f) Two-way ANOVA, *p<0.001, **p<0.0001 vs Adamts1+/−L-NAME at each time point. (g-i) One-way ANOVA, *p<0.001, ****p<0.0001, Adamts1+/+vs Adamts1+/−; #p<0.05, ###p<0.001 L-NAME vs Control.
Figure 4:
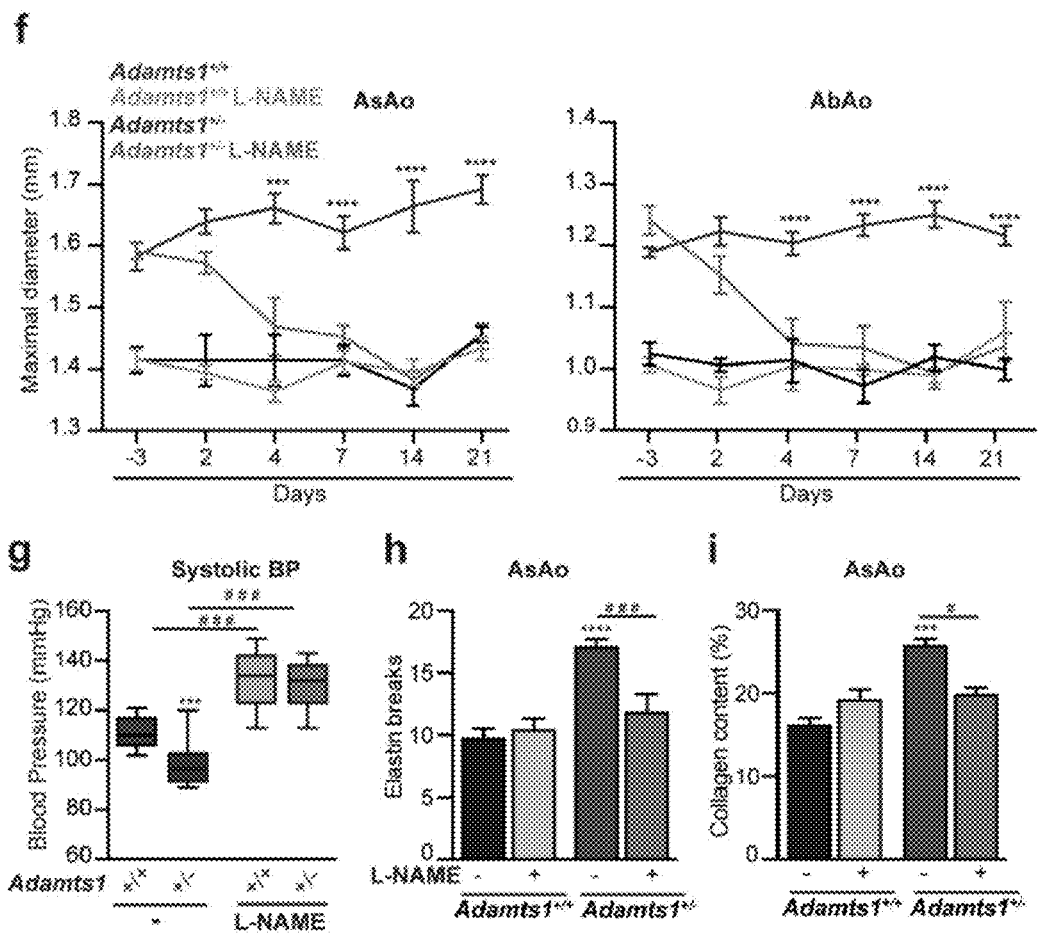
Figure 5:
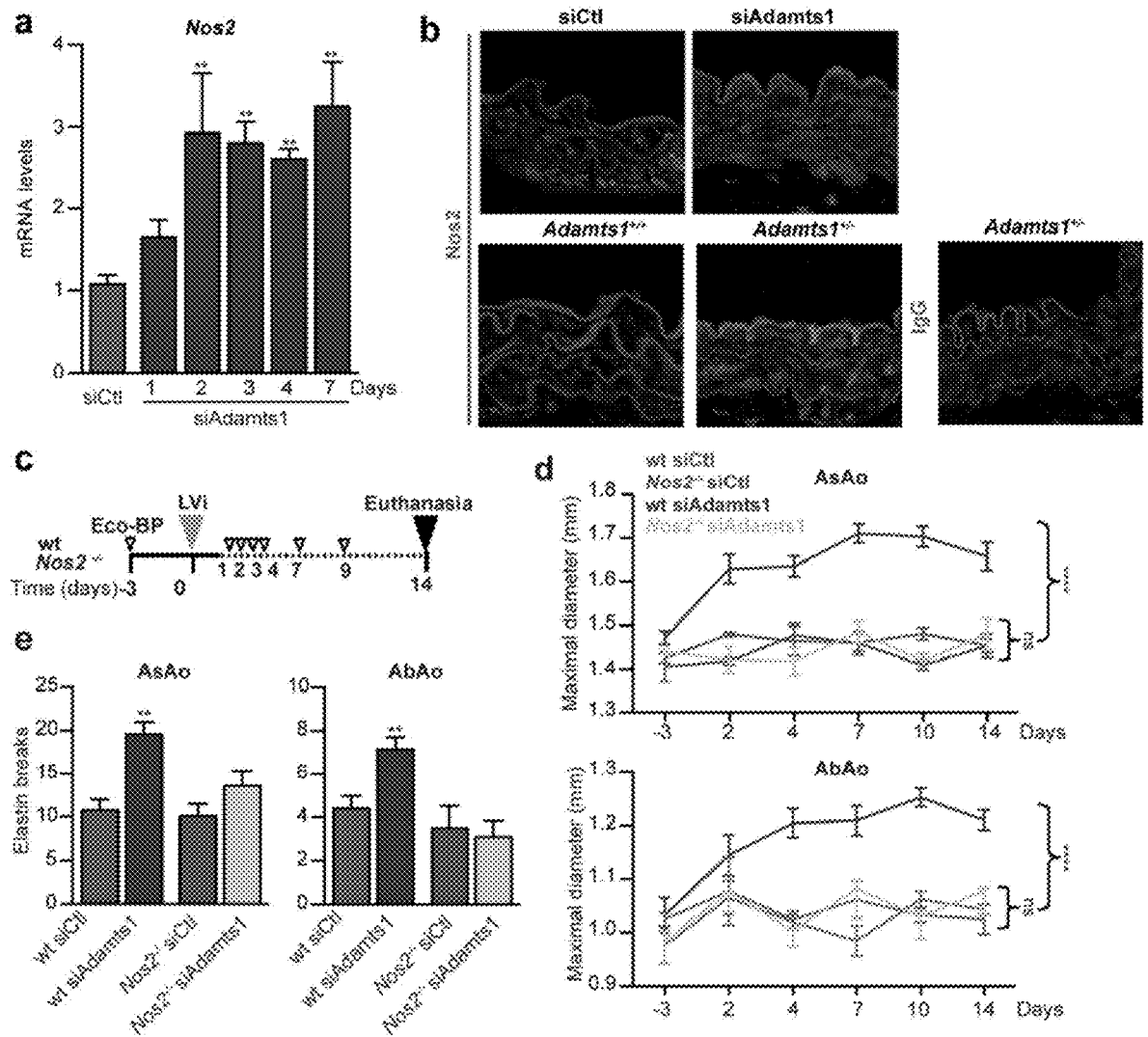
Figure 5:
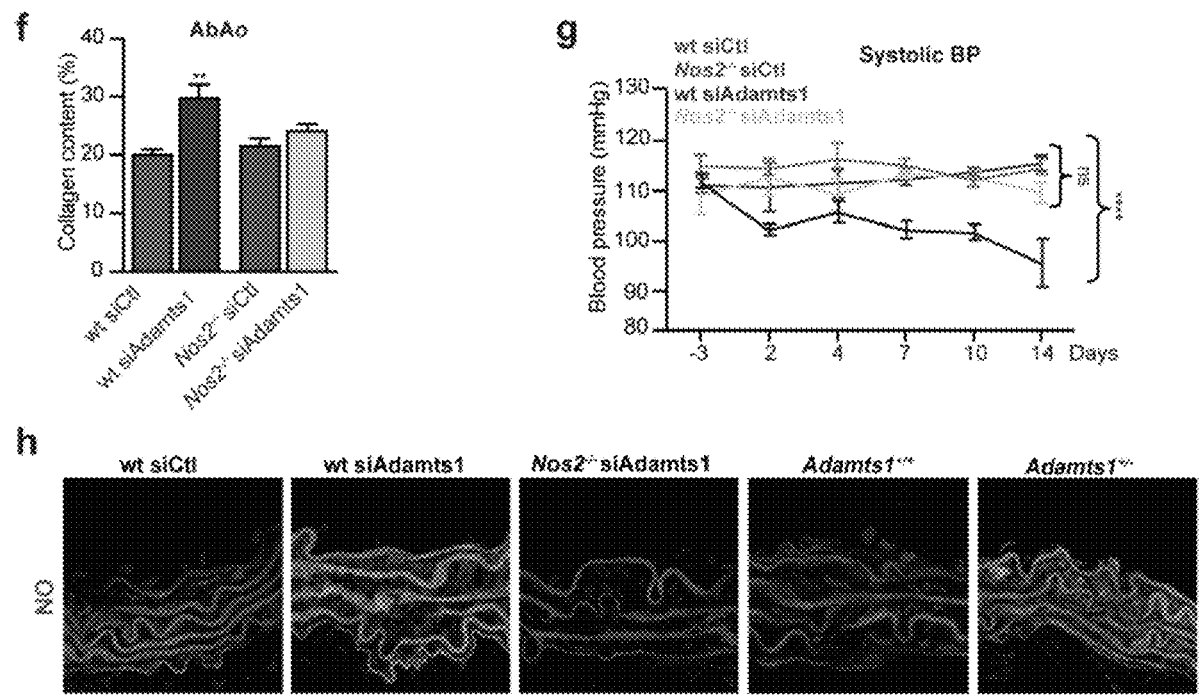
Figure 5:
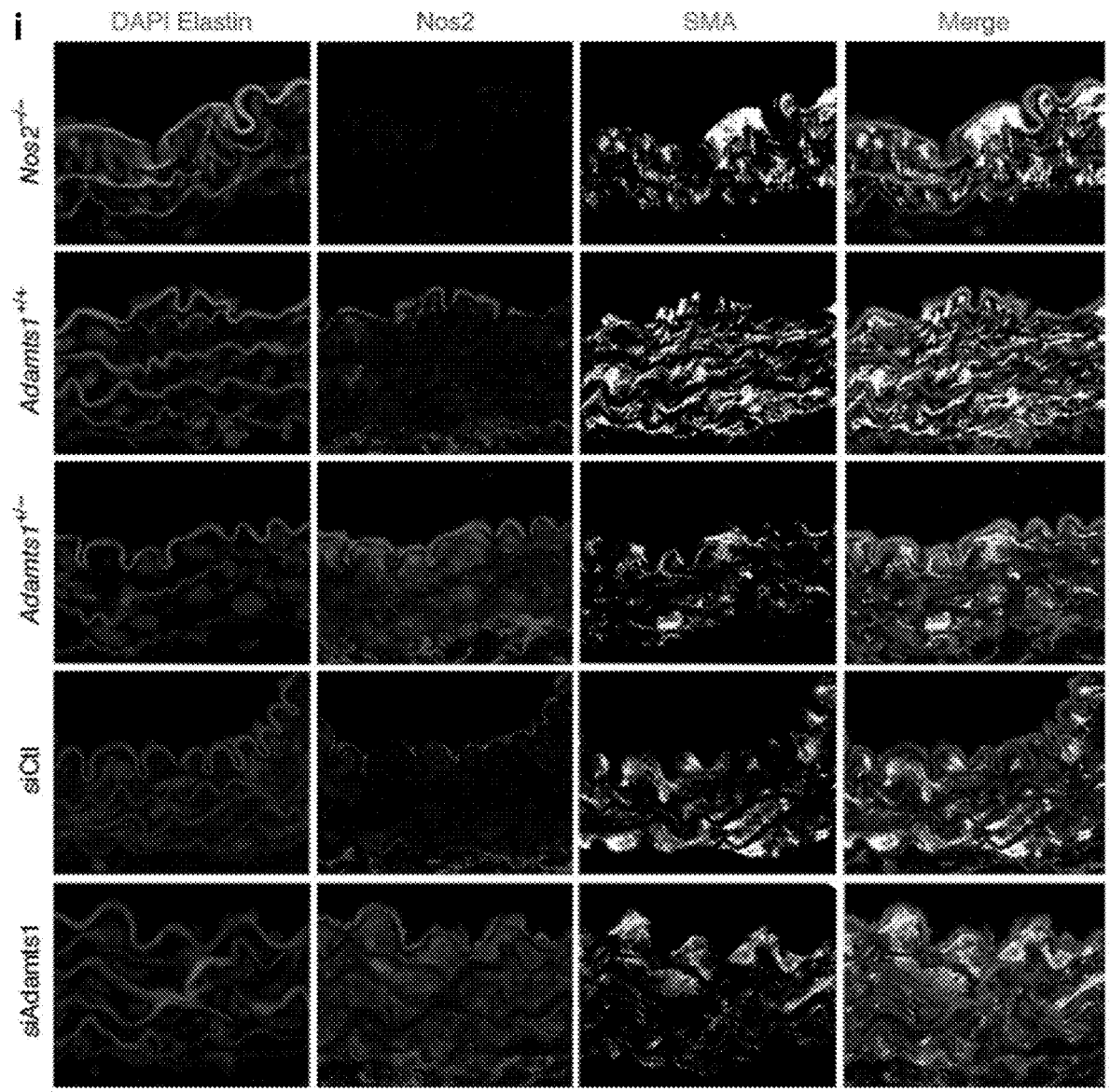
Figure 5:
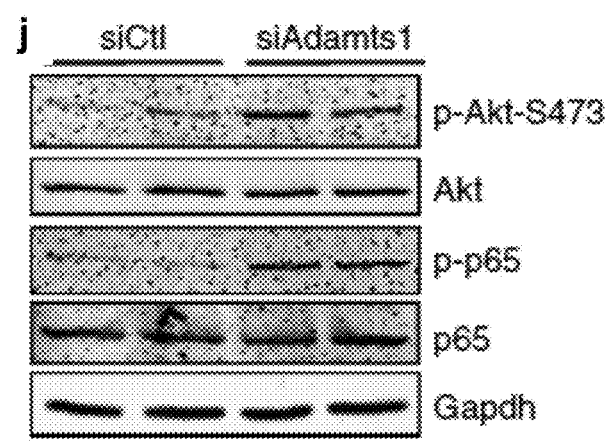

FIG. 5. Nos2 is a critical mediator of the aortopathy induced by Adamts1 deficiency. (a) RT-qPCR analysis of Nos2 mRNA in aortic extracts from siCtl- and siAdamts1-transduced mice at the indicated time points. One-way ANOVA (n=4), p<0.01, vs siCtl. siCtl levels were determined as in FIG. 4. (b) Representative immunofluorescence staining (n=3) of Nos2 (red), elastin autofluorescence (green) and DAPI-stained nuclei (blue) in aortic sections from siCtl and siAdamts1 mice (14 days post-inoculation) and from 12-week-old Adamts1+/+ and Adamts1+/− mice. IgG was used as negative control. Scale bar, 50 µm. (c) Experimental design. Eight-week-old Nos2−/− and wt mice were inoculated with siCtl and siAdamts1 lentivirus and monitored for aortic dilation and BP. (d) Maximal AsAo and AbAo diameter (mean±SEM) in 6 wt siCtl, 9 wt siAdamts1, 4 Nos2−/− siCtl, and 7Nos2−/− siAdamts1 mice at the indicated time points. Two-way ANOVA of group means; p<0.0001 vs Nos2−/− siAdamts1; ns, non-significant. End-of-experiment quantification of (e) elastin breaks in the AsAo and AbAo and (f) collagen content in the AbAo in the same animal cohort. (g) Systolic BP (mean±SEM) at the indicated time points in the same cohort of mice. Two-way ANOVA of group means; **p<0.0001 vs Nos2−/− siAdamts1; ns, non-significant. (h) Representative images (n=3) of NO production (red), elastin autofluorescence (green) and DAPI-stained nuclei (blue) in unfixed aortic tissue sections from siCtl, siAdamts1, and Nos2−/− siAdamts1 mice (14 days post-inoculation) and from 10-week-old Adamts1+/+ and Adamts1+/− mice. Scale bar, 50 µm. (i) Representative images of Nos2 (red) and SMA (white) immunofluorescence, elastin autofluorescence (green) and DAPI-stained nuclei (blue) in aortic sections from 16-week-old Nos2−/−, Adamts1+/+ and Adamts1+/− mice and from WT mice that were inoculated with siCtl- or siAdamts1-expressing lentivirus (4 d after inoculation) (n=4 mice per group). Scale bar, 50 µm. (j) Representative immunoblot analysis of total and phosphorylated Akt and p65 in aortic extracts of WT mice treated with siCtl- orsiAdamts1-expressing lentivirus (n=5 mice per group). Each lane represents one mouse. (i-1) Maximal AsAo (left) and AbAo (right) diameters at the indicated time points.

Figure 6:
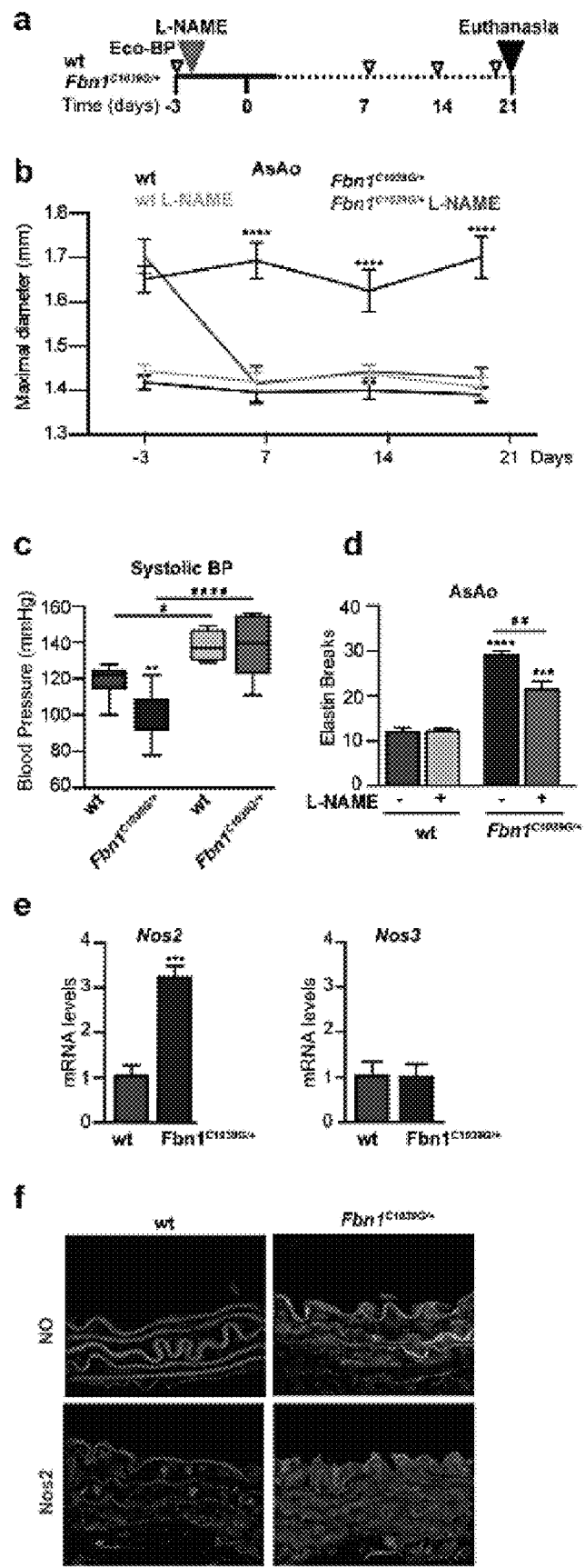
Figure 6:
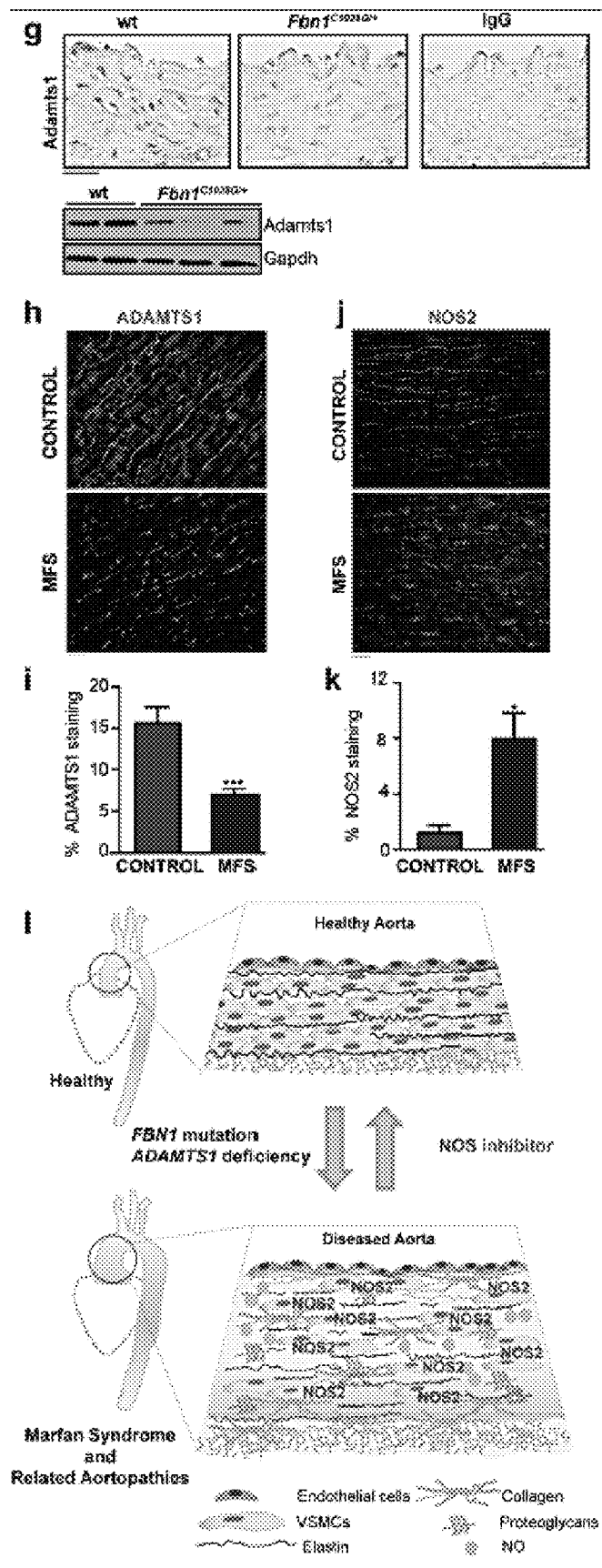
Figure 6:
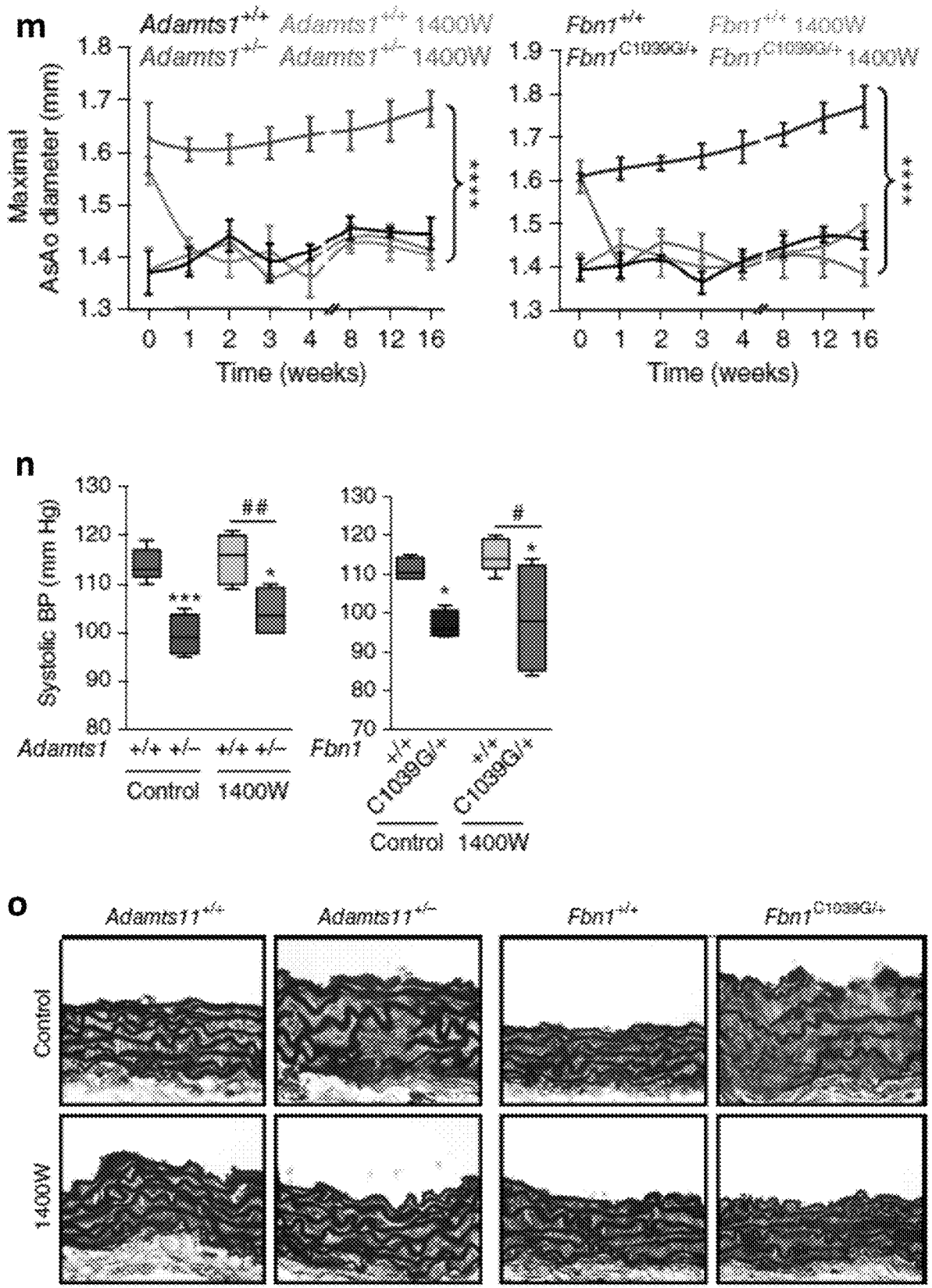
Figure 6:
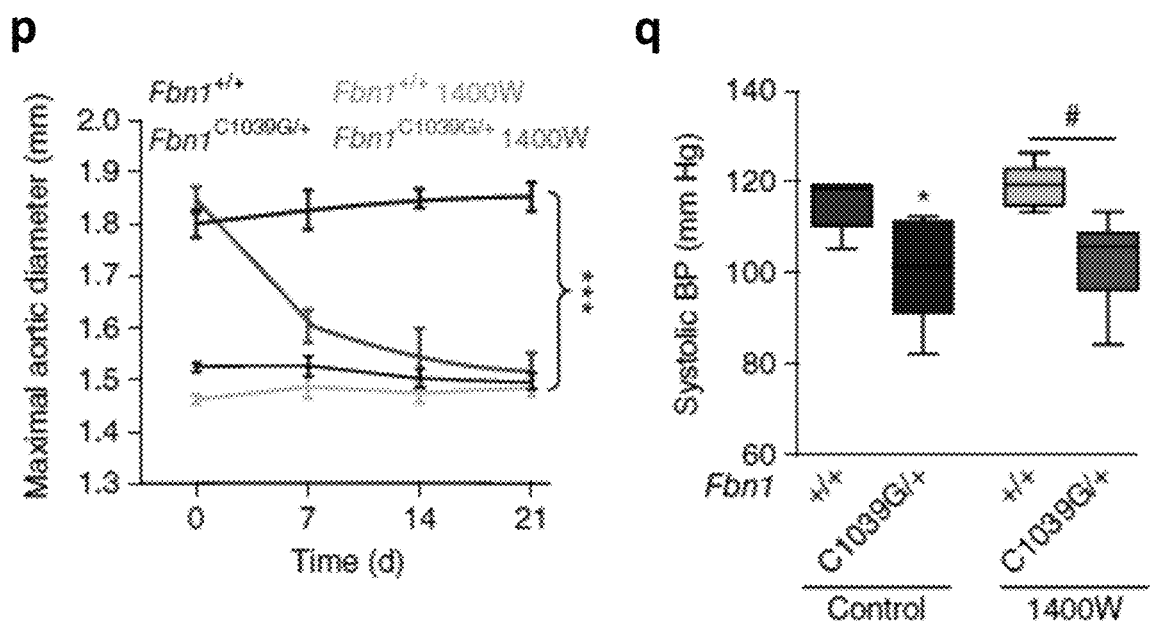

FIG. 6. Adamts1 and NO play a critical role in Marfan syndrome. (a) Experimental scheme. Twelve-week-old wt and Fbn1C1039G/+ mice were given L-NAME in the drinking water for 21 days. Aortic dilation and BP were determined at the indicated times and before euthanasia. (b) Maximal AsAo diameter (mean±SEM) at the indicated times and (c) End-of experiment quantification of systolic BP in 9 wt, 7 wt L-NAME, 8 Fbn1C1039G/+, and 8 Fbn1C1039G/+ L-NAME mice. (b) Two-way ANOVA, **<0.0001 vs Fbn1C1039G/+L-NAME. (c) One-way ANOVA, p<0.01 vs control wt; #p<0.05, ####p<0.0001 control vs L-NAME. (d) End-of-experiment quantification of elastin breaks in the AsAo in 6 wt, 3 wt L-NAME, 3 Fbn1C1039G/+, and 5 Fbn1C1039G/+L-NAME mice. One-way ANOVA; *p<0.001, p<0.0001, vs control wt; ##p<0.01 control vs L-NAME. (e) RT-qPCR analysis of Nos2 and Nos3 mRNA in aortic extracts from 6 wt and 3 Fbn1C1039G/+ mice. Student's t-test, *p<0.001. (f) Representative images (n=3) of NO production (red), Nos2 immunofluorescence (red), elastin autofluorescence (green), and DAPI-stained nuclei (blue) in aortic cross sections of wt and Fbn1C1039G/+ mice. (g) Representative Adamts1 immunohistochemistry in aortic sections from wt and Fbn1C1039G/+ mice and immunoblot analysis of Adamts1 in aortic extracts. IgG staining serves as a negative control. Scale bar, 20 µm. (h) Representative medial layer images of ADAMTS1 immunofluorescence (red; n=9) and (i) quantification of ADAMTS1-positive area in immunohistochemistry-stained sections of 5 control donors and 9 MFS patients. (j) Representative medial layer images of NOS2 immunofluorescence (red; n=6) and (k) quantification of NOS2-positive area in sections from 5 control donors and 8 MFS patients. Bar, 25 µm. (h,j) Elastin autofluorescence (green) and DAPI-stained nuclei (blue) are also shown. (i,k) Data are presented as mean+SEM. Student's t-test; *p<0.05, *p<0.001. (1) Model depicting the contribution of NO and NOS2 to the aortic phenotype in Marfan syndrome and the related aortopathy induced by Adamts1 deficiency. (m) Maximal AsAo diameter at the indicated time points in the groups of mice indicated (n=4 mice per group), end-of-experiment systolic BP (n=4 mice per group). (n) representative images of EVG staining in aortic sections (same cohorts of miceas in 1). (o) from 12-week-old Adamts1+/− and Fbn1+/C1039G mice and their corresponding WT littermates after treatment with 1400W (in the drinking water) for 16 weeks. Data are means±s.e.m. (p,q) Maximal AsAo diameter at the indicated time points (p) and end-of-experiment systolic BP (k) in 36-week-old Fbn1+/C1039G mice and their WT littermates treated with 1400W in the drinking water for 21 d (n=5 control or 1400W treated WT mice; n=7 control Fbn1+/C1039G mice; n=6 1400W-treated Fbn1+/C1039G mice). Data are means±s.e.m. (p) or box-and-whisker plots, with 75th and 25th percentiles; bars represent maximal and minimal values (q). *P<0.001 (versus 1400W-treated Fbn1+/C1039G mice); *P<0.05 (versus control WT); #P<0.05 (versus treated WT); by repeated-measurements two-way ANOVA of group means (o) or two-way ANOVA (q).

Figure 7:
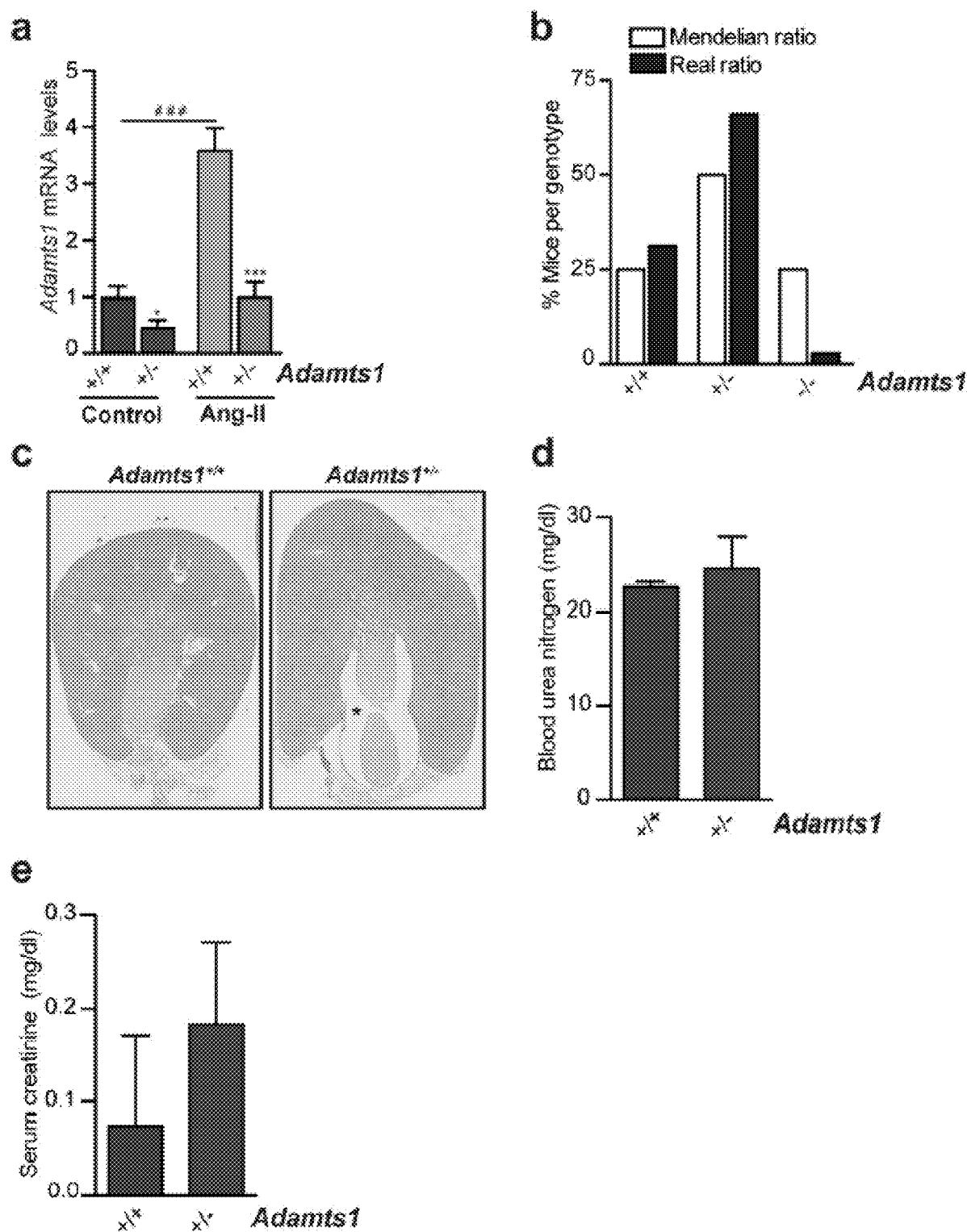

FIG. 7. (a) RT-qPCR analysis of Adamts1 mRNA expression in Adamts1+/+ and Adamts1+/− treated for 28 days as indicated. One-way ANOVA, *p<0.05, ***p<0.001 Adamts1+/+ vs Adamts1+/; ###p<0.001 Control Adamts1+/+ vs Ang-II Adamts1+/+. (b) Percentage of Adamts1+/+, Adamts1+/−, and Adamts1−/− mice alive at weaning vs their expected Mendelian ratio (n=151). (c) Representative hematoxylin-eosin (H&E) staining of transverse kidney sections from 3-4-month-old 10 Adamts1+/+ and 7 Adamts1+/− mice; *indicates hydronephrotic space. Scale bar, 500 µm. (d) Plasma urea and (e) plasma creatinine levels in 9-week-old Adamts1+/+(n=5) and Adamts1+/− (n=6) mice (mean+SEM).

Figure 8:
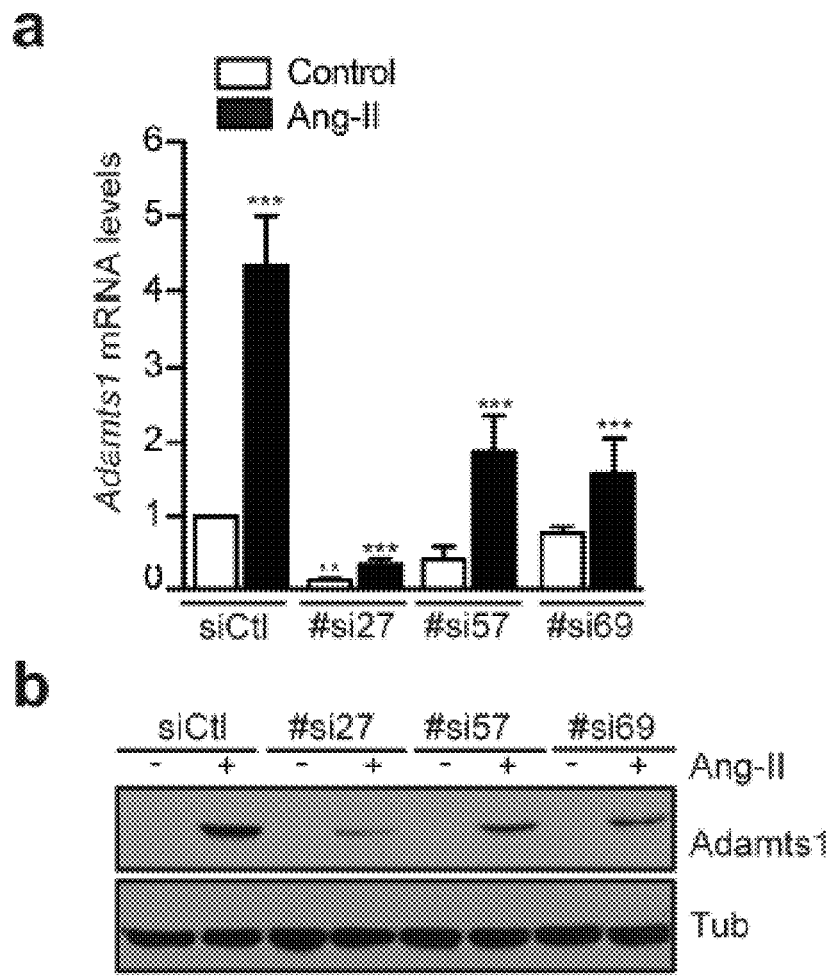
Figure 8:
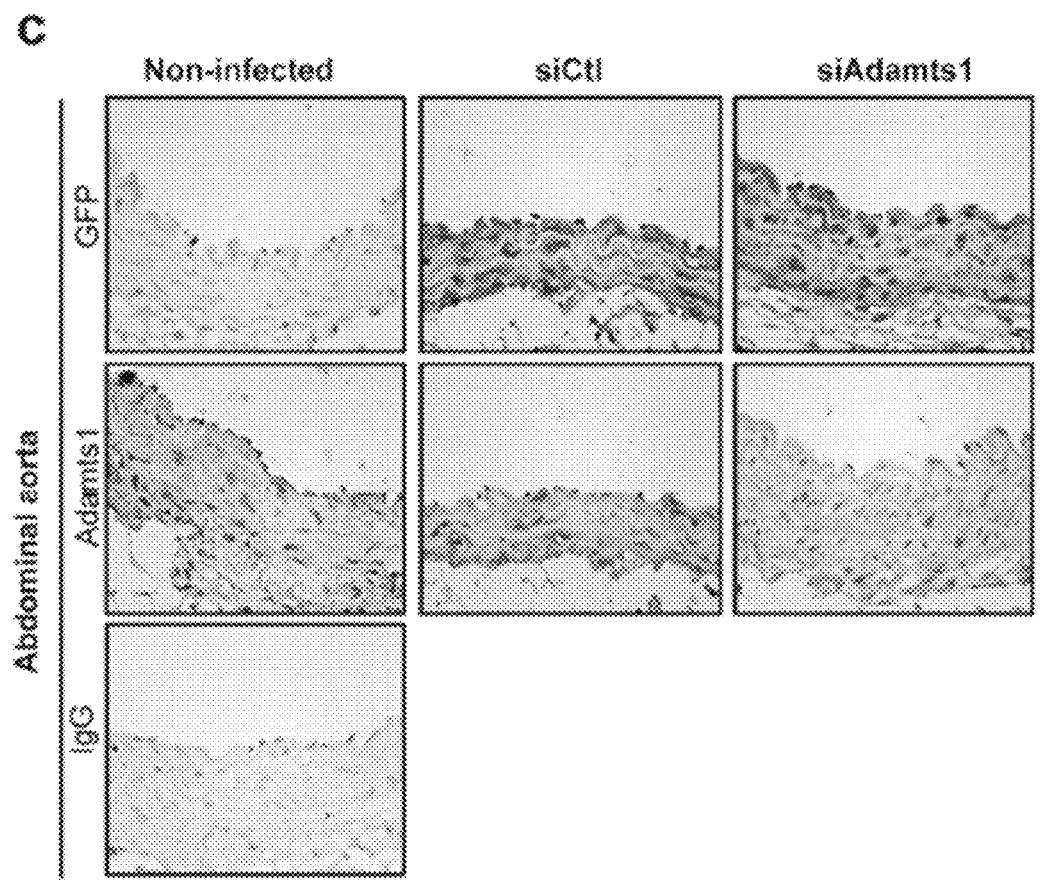
Figure 8:
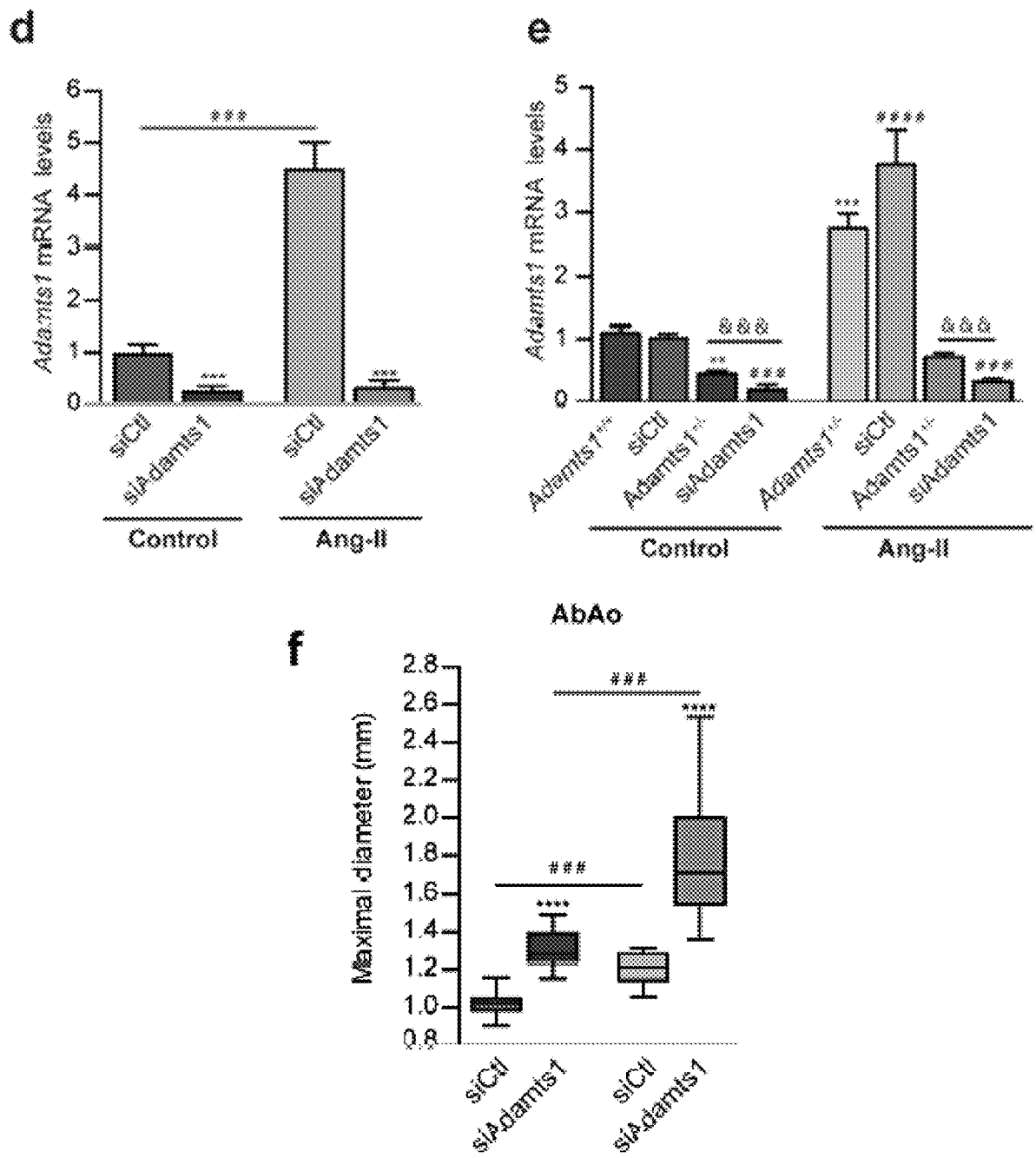

FIG. 8. (a-b) Vascular smooth muscle cells were transduced with lentivirus encoding Adamts1-specific siRNA (#si27, #si57, #si69) or a control siRNA (siCtl). Adamts1 levels were analyzed by (a) RT-qPCR and (b) immunoblot in extracts from these cells. mRNA amounts were normalized to Gapdh expression (mean+SEM; n=3). Oneway ANOVA, p<0.01, *p<0.001, **p<0.0001 vs untreated siCtl. Tubulin expression was used as a loading control. (c) Representative GFP and Adamts1 immunostaining on AbAo sections. IgG staining serves as a negative control. Scale bar, 50 µm.(d) Adamts1 mRNA levels in aortic samples from mice transduced with siCtl or siAdamts1 treated as indicated for 28 days. Numbers of mice per group were 12 control siCtl, 16 control siAdamts1, 13 Ang-II siCtl, and 16 Ang-II siAdamts1. mRNA amounts were normalized to Gapdh expression (mean+SEM). One-way ANOVA, *p<0.001 vs siCtl; ###p<0.001 vs control. (e) Adamts1 mRNA levels in aortic samples from the indicated mice and treatments (n>6). mRNA amounts were normalized to Gapdh expression (mean+SEM). One-way ANOVA, p<0.01, *p<0.001 vs control Adamts1+/+; ###p<0.001, ####p<0.0001 vs control siCtl; &&&p<0.001 Adamts1+/− vs siAdamts1. (f) End-of-experiment maximal aortic diameter (mean±SEM) analyzed in the same cohort of mice than (d). One-way ANOVA, ****p<0.001 siCtl vs siAdamts1; #p<0.05 and ###p<0.001 control vs Ang-II.

Figure 9:
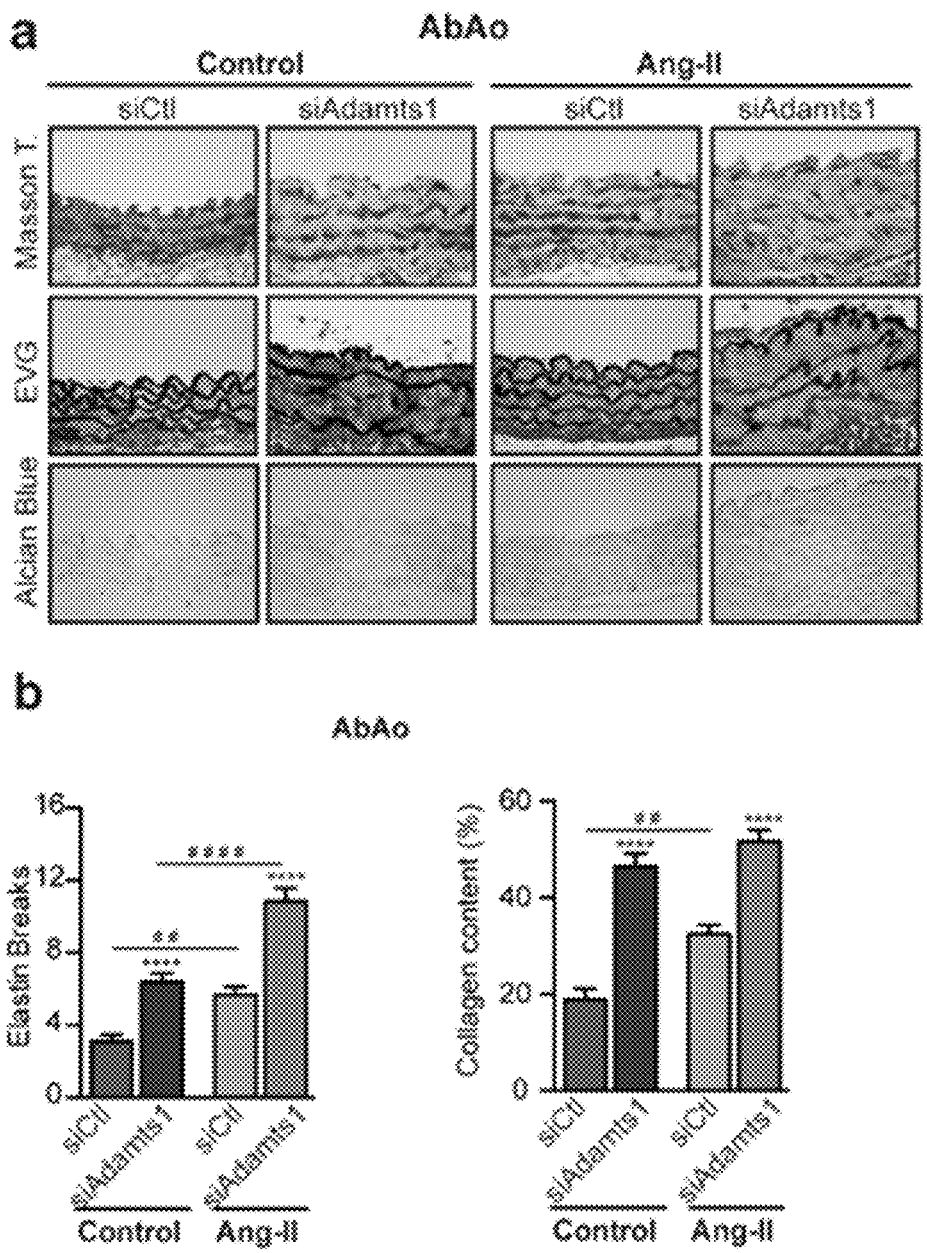
Figure 9:
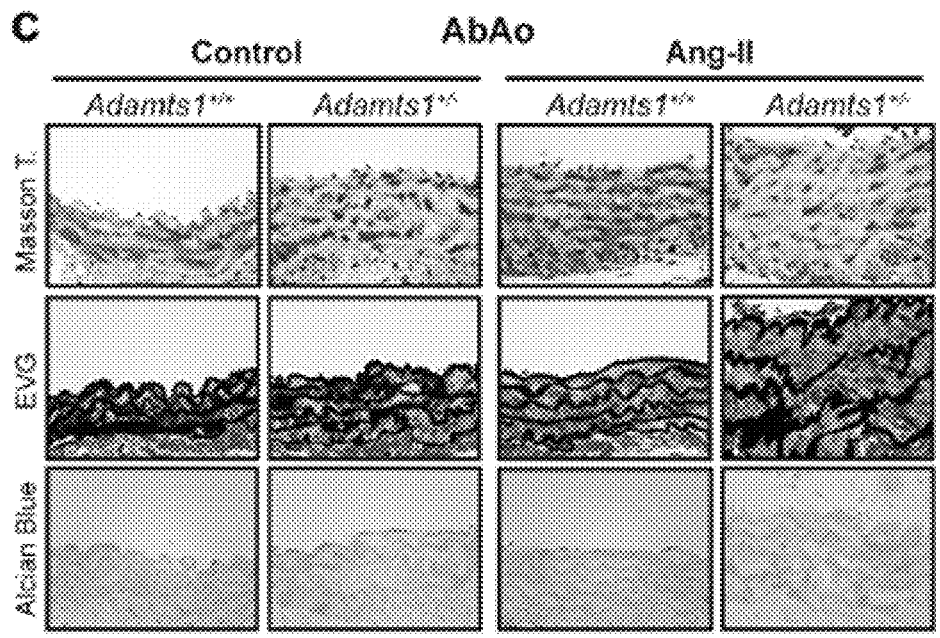
Figure 9:
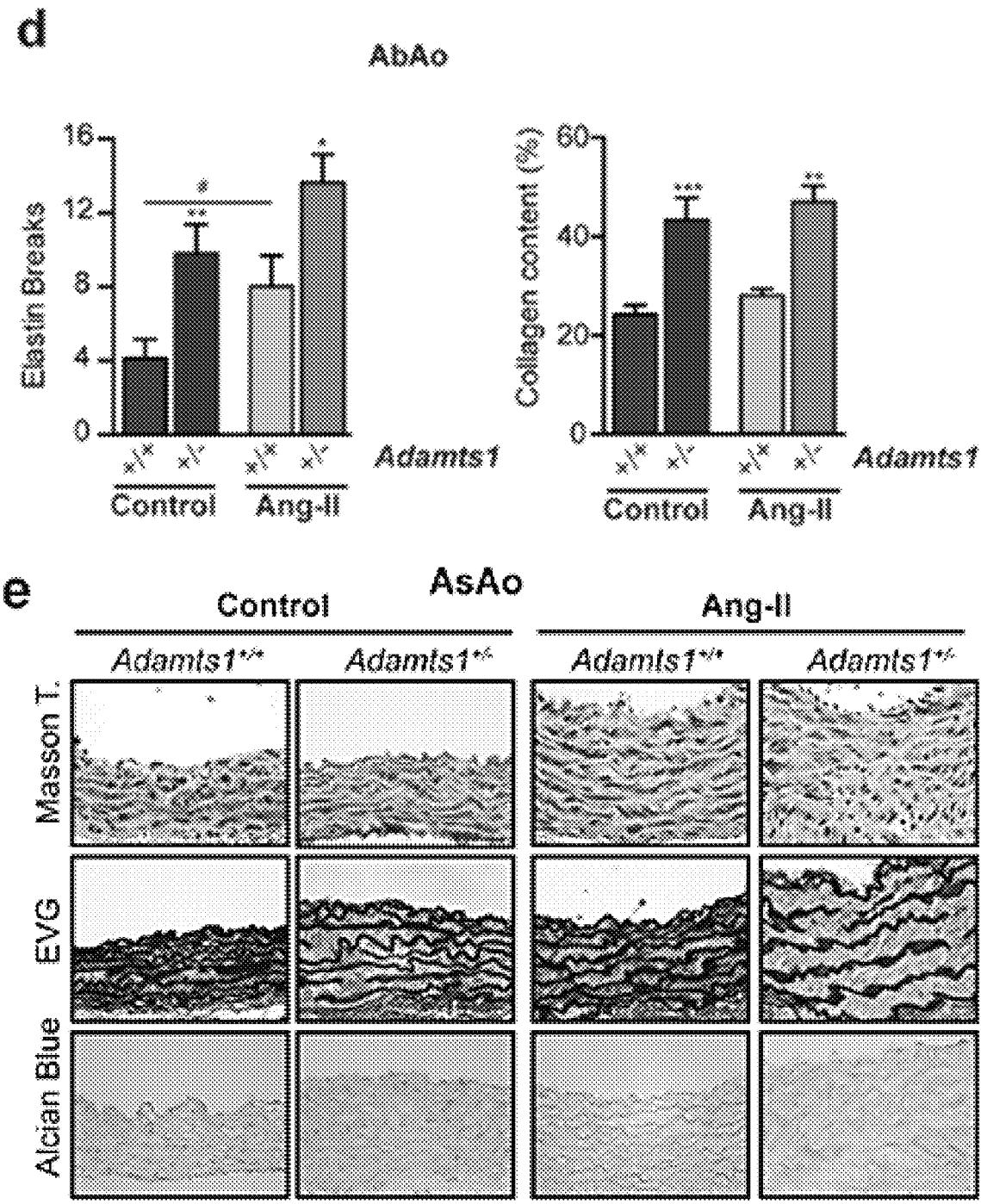

FIG. 9. (a) Representative Masson's trichrome (Masson T), elastin van Gieson (EVG), and alcian blue staining and (b) quantification of elastin breaks and collagen content in AbAo sections from the mouse cohorts shown in FIG. 2g. (c-e) Representative Masson's trichrome (Masson T), elastin van Gieson (EVG), and alcian blue staining on (c) AbAo and (e) AsAo sections and (d) quantification of elastin breaks and collagen content in AbAo sections from the mouse cohorts shown in FIG. 2h. (a,c,e) Scale bars, 50 µm. (b,d)) One-way ANOVA, *p<0.05, p<0.01, *p<0.001, ****p<0.0001 siCtl vs siAdamts1 or Adamts1+/+ vs Adamts1+/−; #p<0.05, ##p<0.01, ####p<0.0001 Control vs Ang-II.

Figure 10:
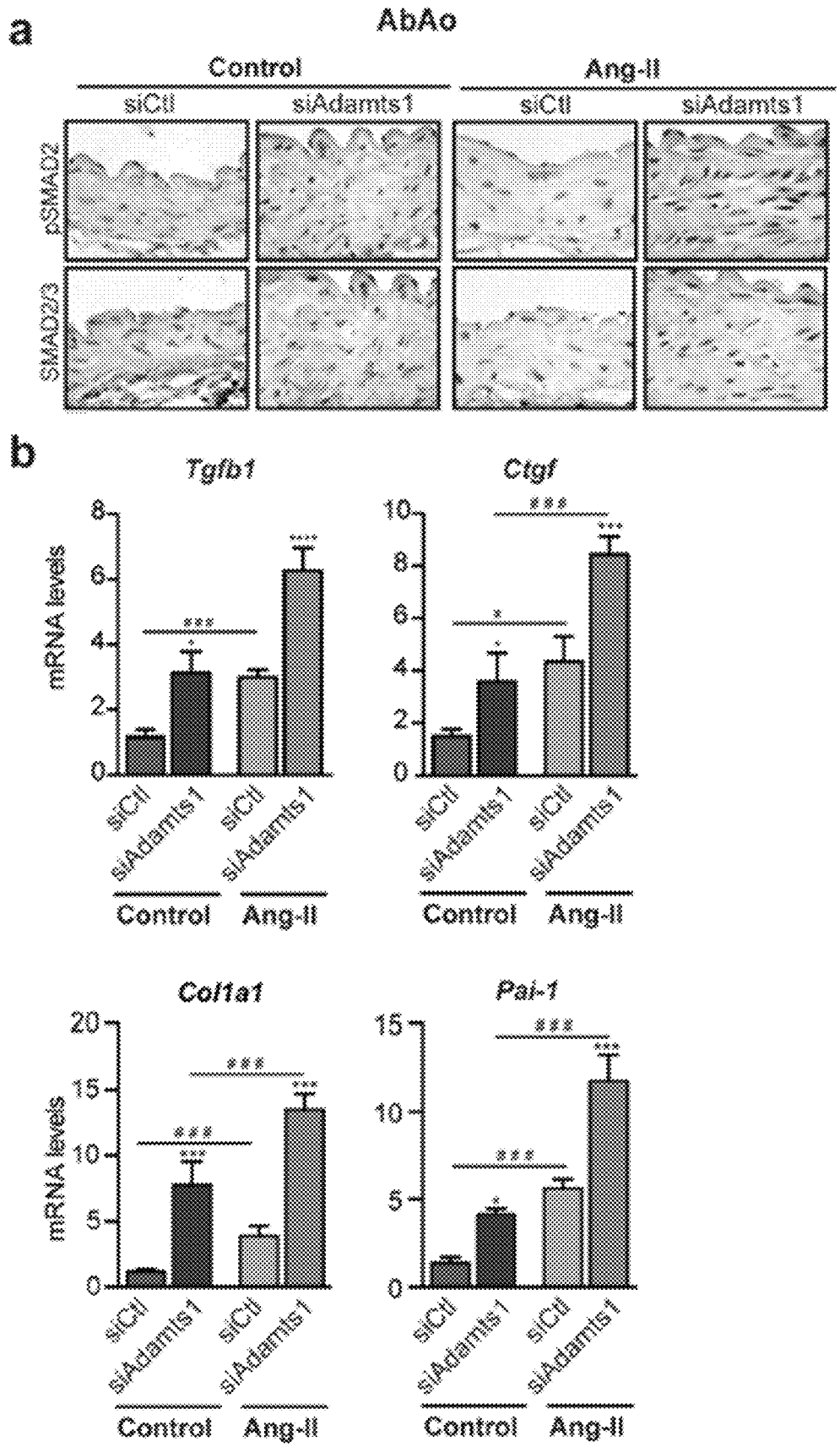
Figure 10:
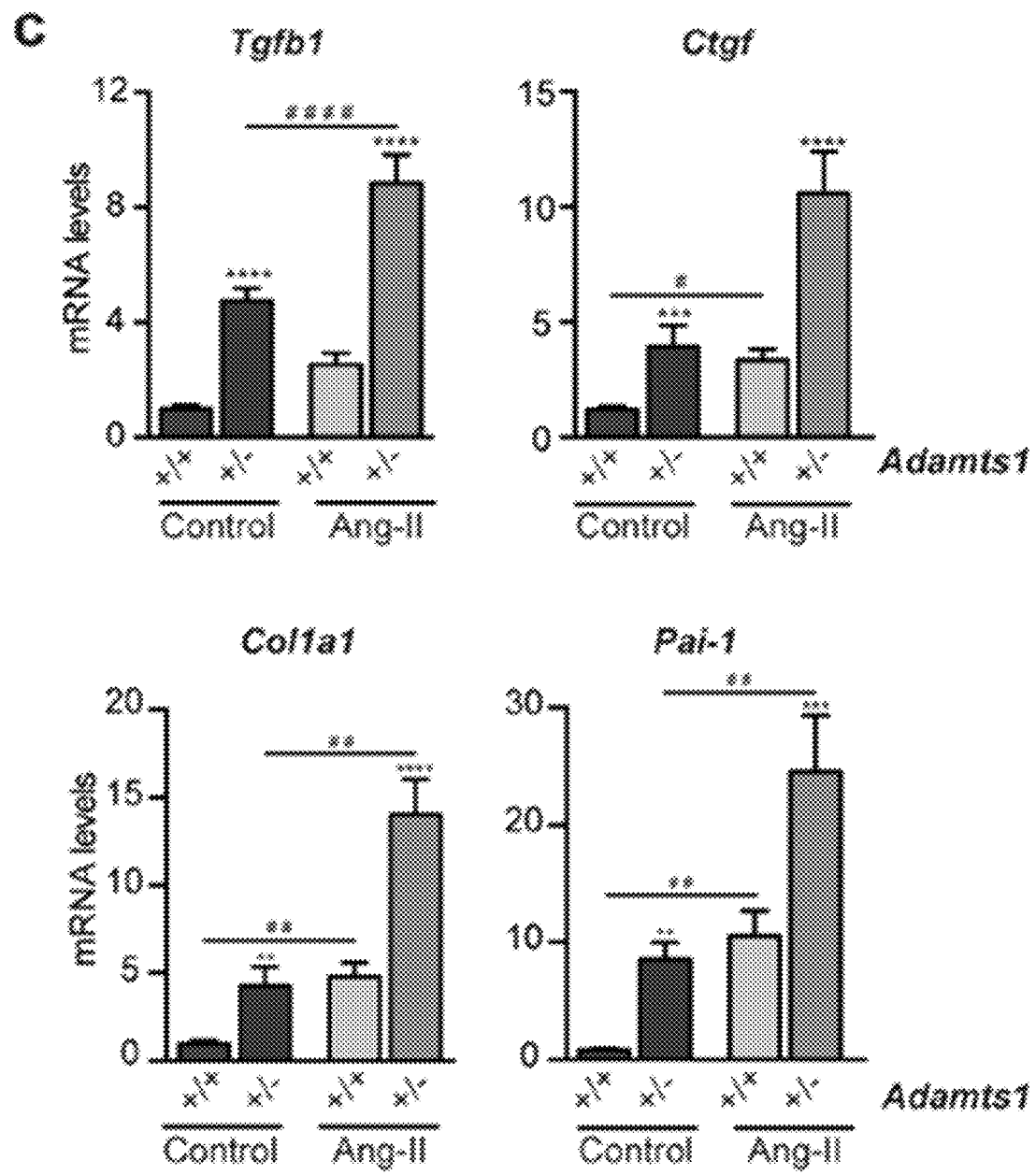
Figure 10:
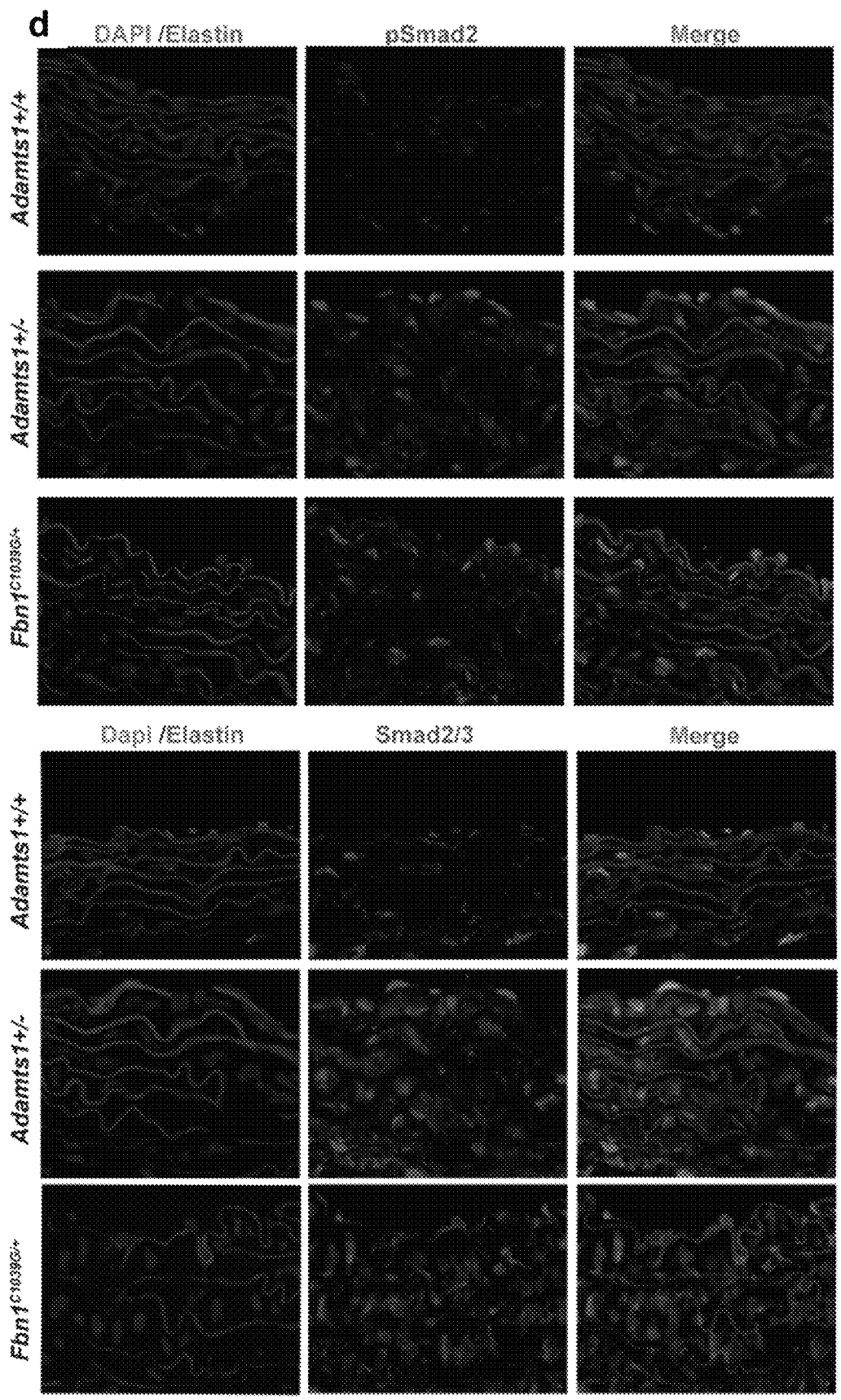

FIG. 10. (a) Representative pSMAD2 and SMAD2/3 immunostaining (n=3) on AbAo cross sections from siCtl- and siAdamts1-transduced mice treated as indicated. Scale bar, 50 µm. RT-qPCR analysis of Tgfb1, Ctgf, Col1a1, and Pai-1 mRNA expression in extracts from control and Ang-II-treated (b) siCtl- and siAdamts1-transduced mice and (c) Adamts1+/+ and Adamts1+/− mice. One-way ANOVA, *p<0.05, ***p<0.001, siCtl vs siAdamts1; #p<0.05, ###p<0.001 Control vs Ang-II. (d) Adamts1+/+ and Adamts1+/− mice. Two-way ANOVA, *p<0.05, *p<0.001, **p<0.0001, siCtivs siAdamts1; #p<0.05, ##p<0.01, ###p<0.001, ####p<0.0001, Control vs Ang-II.

Figure 11:
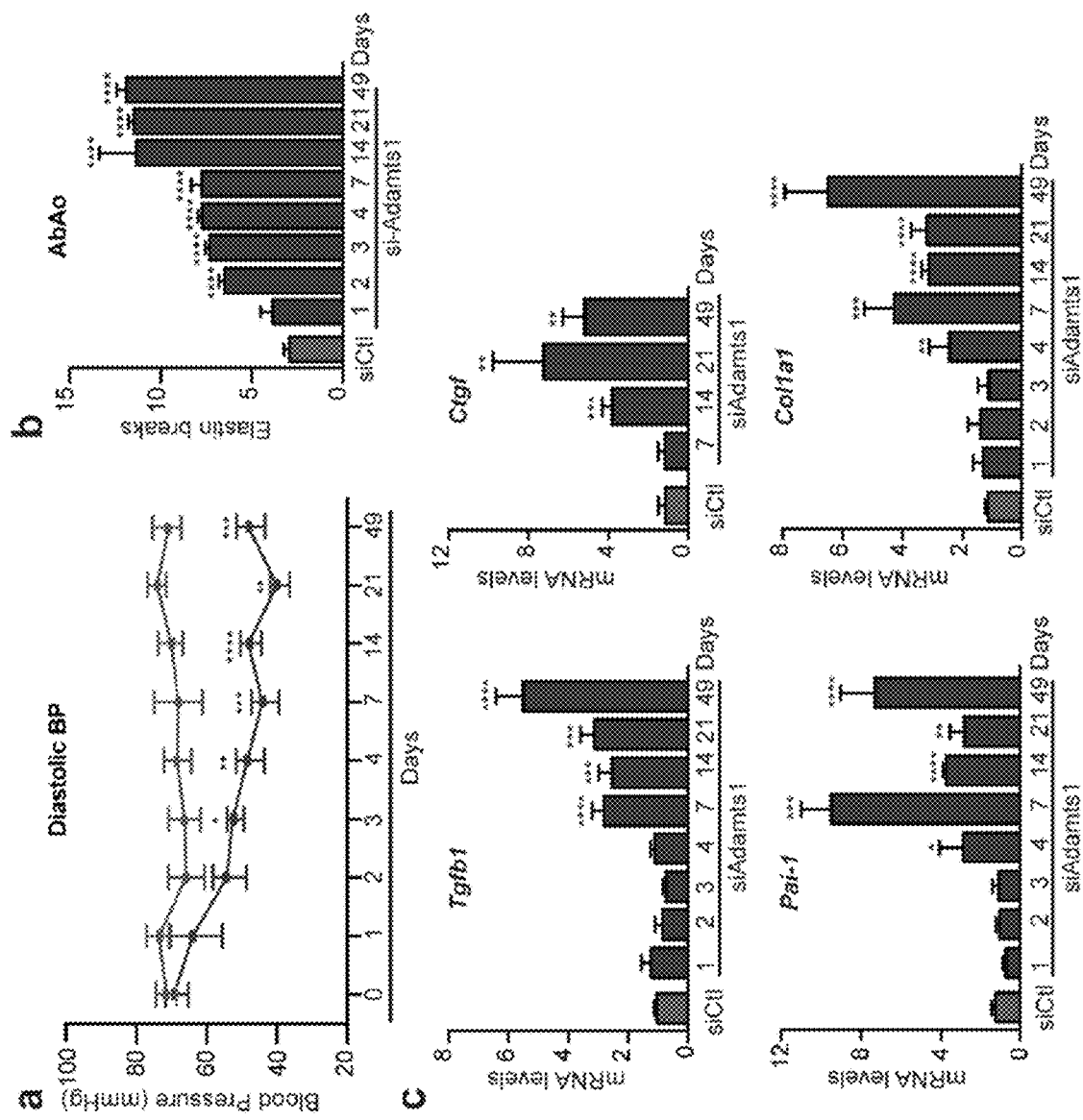
Figure 11:
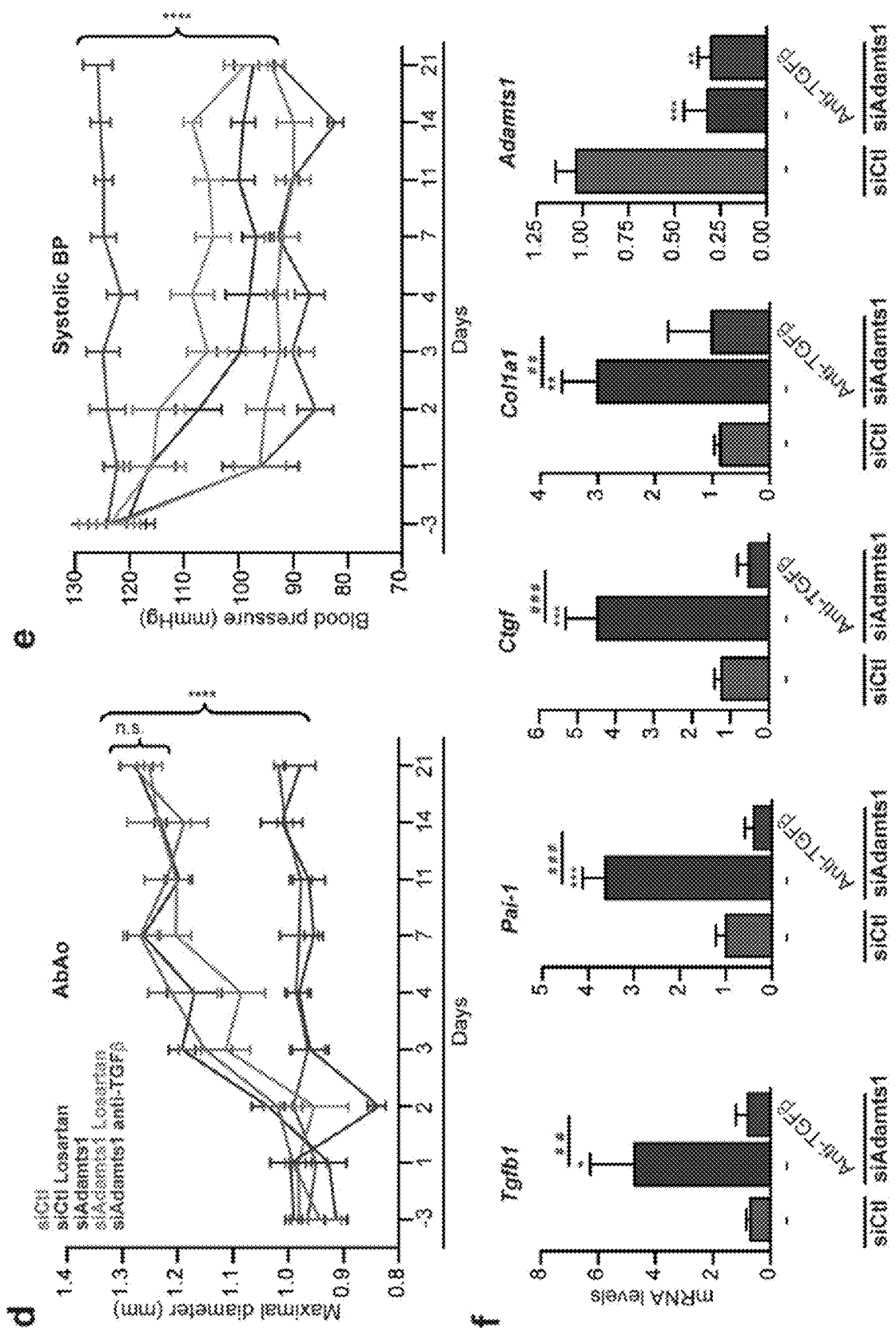

FIG. 11. (a) Diastolic BP (mean±SEM) measured at the indicated times in siCtl- and siAdamts1-transduced mice. Two-way ANOVA (n=5-12); *p<0.05, p<0.01, *p<0.001 vs siCtl at each time point. (b) Elastin breaks in AbAo cross sections from the same mice. (c) RT-qPCR analysis of Tgfb1, Ctgf, Col1a1 and Pai-1 expression in the same mice at the indicated times. mRNA amounts were normalized to Gapdh expression. One-way ANOVA; *p<0.05, p<0.01, *p<0.001, **p<0.0001 vs siCtl. siCtl results in (b,c) were stable throughout the experimental period, and data are means of readings at 2, 4, 7, 14, 21, and 49 days. (d) Maximal AbAo diameter (mean±SEM) and (e) systolic BP (mean±SEM) at the indicated times in 8 siCtl, 4 siCtl losartan, 5 siAdamts1, 7 siAdamts1 losartan, and 6 siAdamts1 anti-TGFβ mice. Two-way ANOVA of group means, **p<0.0001 vs siCtl; n.s., non-significant. (f) RT-qPCR analysis of Tgfb1, Pai-1, Ctgf, Col1a1 and Adamts1 mRNA. mRNA amounts were normalized to Gapdh expression. Oneway ANOVA; *p<0.05, p<0.01, *p<0.001 vs siCtl; ##p<0.05, ###p<0.001.

Figure 12:
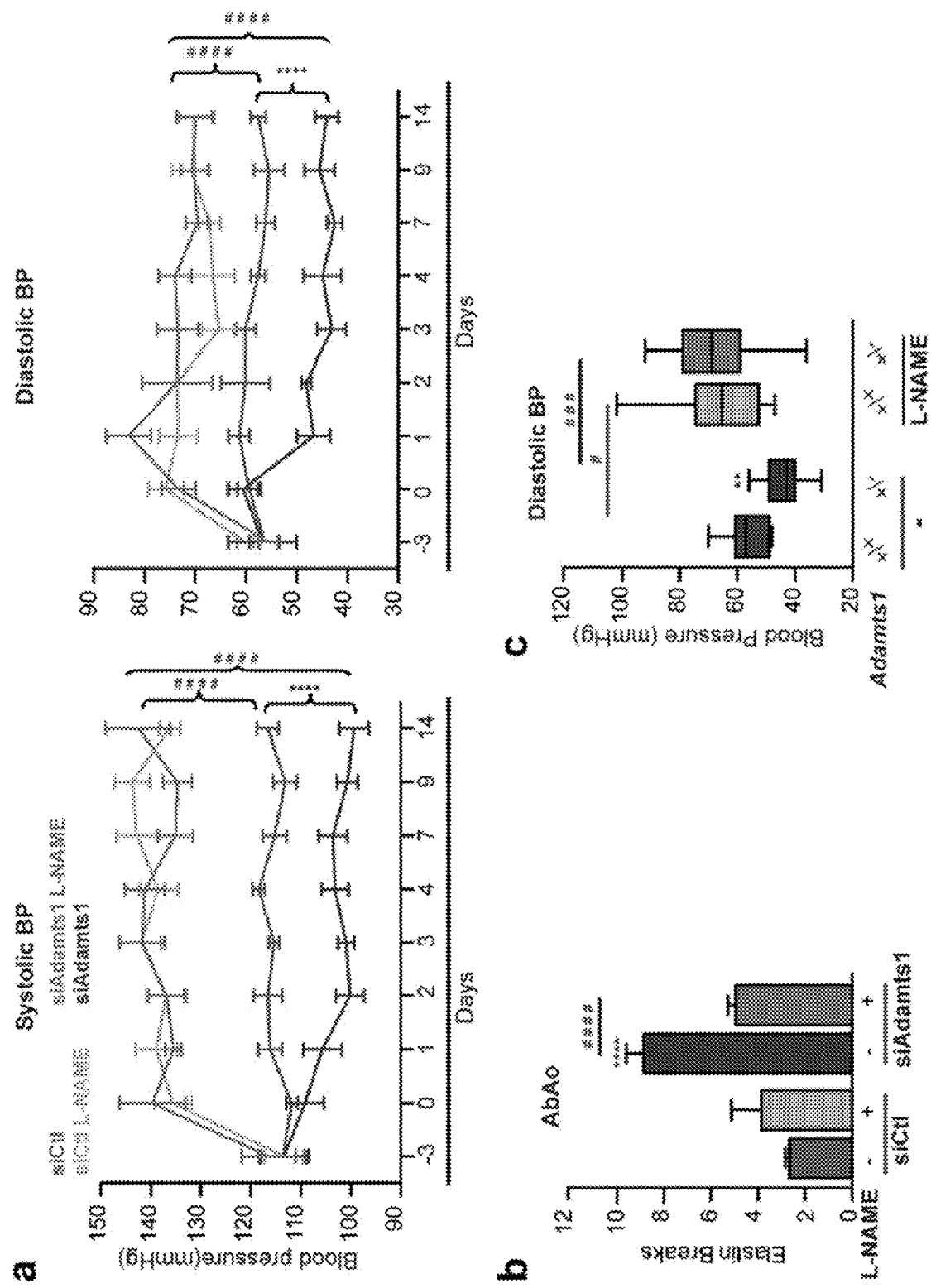

FIG. 12. (a) Systolic and diastolic BP at the indicated times in siCtl- and siAdamts1-transduced mice treated with L-NAME as indicated (mean±SEM; n=5 for each group). Two-way ANOVA of group means, **p<0.0001; ####p<0.0001 control vs L-NAME. (b) End-of-experiment quantification of elastin breaks in AbAo cross sections in the same group of mice. (c) End-of-experiment diastolic BP in the same cohort of mice shown in FIG. 4g. (b,c) One-way ANOVA, p<0.01, ****p<0.0001 vs untreated siCtl or Adamts1+/+ vs Adamts1+/−; #p<0.05, ###p<0.001, L-NAME vs untreated.

Figure 13:
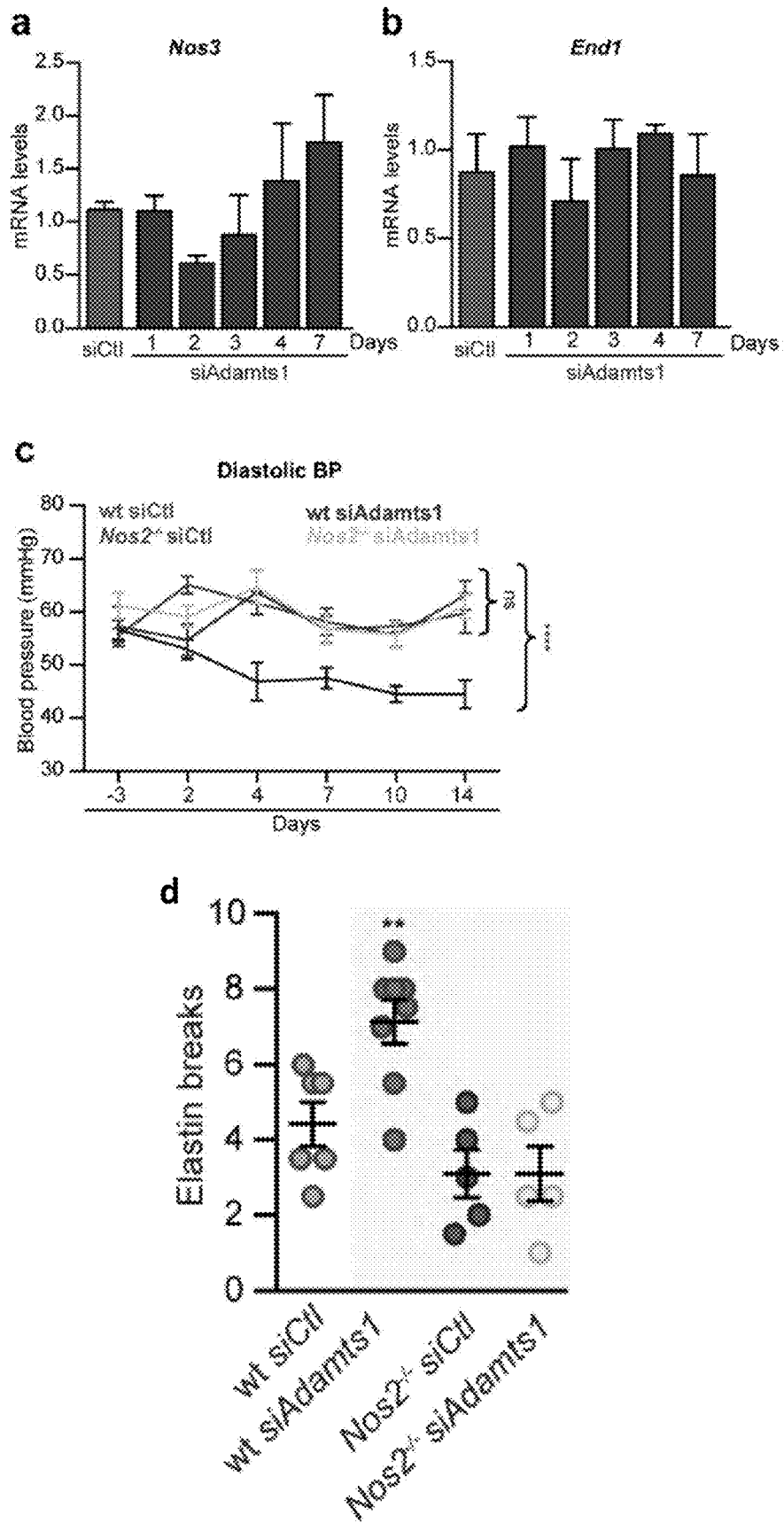
Figure 13:
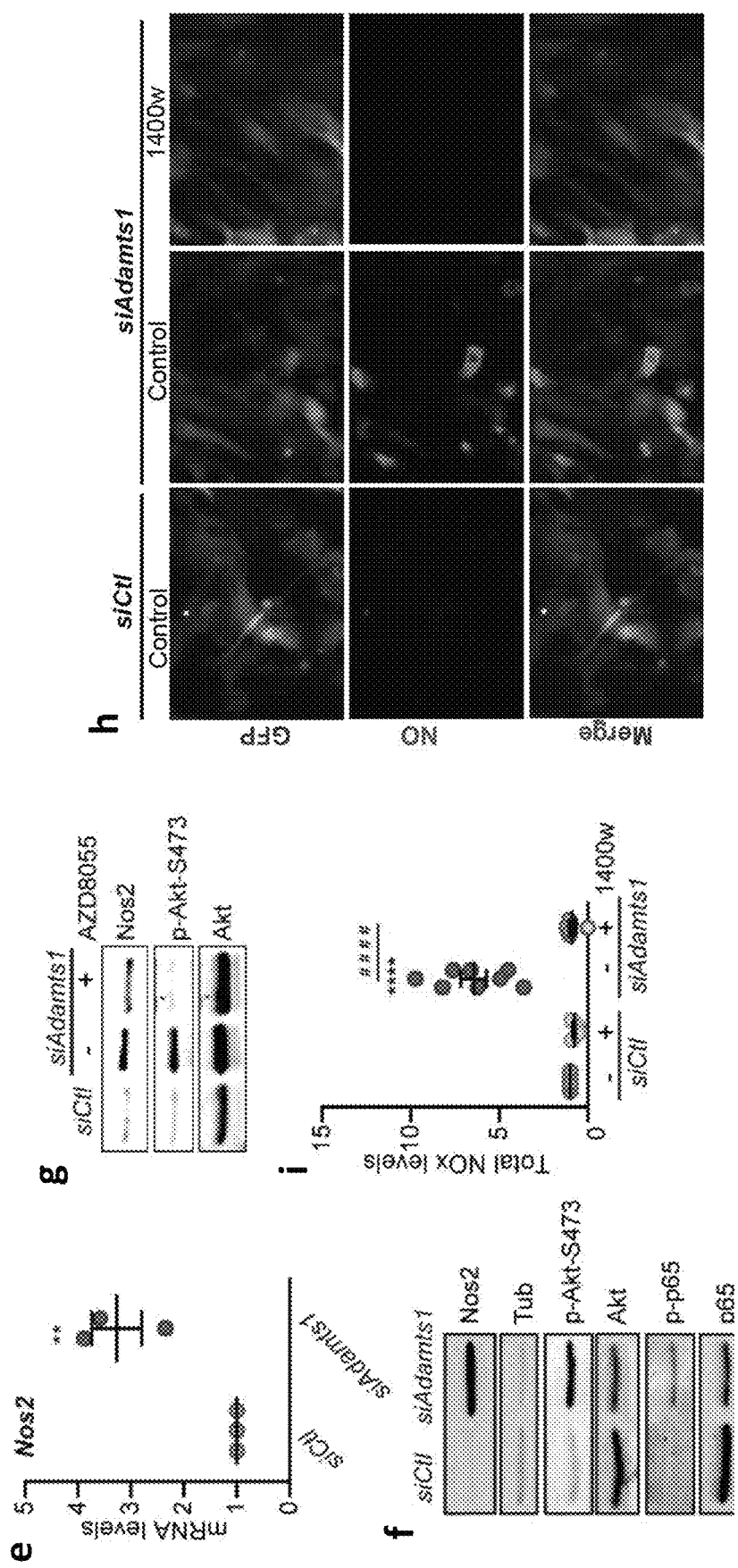

FIG. 13. RT-qPCR analysis of (a) Nos3 and (b) Endl mRNA expression at the indicated times in aortic extracts from siCtl- and siAdamts1-transduced mice. mRNA amounts were normalized to Gapdh expression. One-way ANOVA (n=4), *p<0.001 vs siCtl. (c) Diastolic BP (mean±SEM) in the same cohorts of mice shown in FIG. 5g. Twoway ANOVA of group means, p<0.0001 vs Nos2−/− siAdamts1; ns, non-significant. (d) End-of-experiment quantification of elastin breaks (mean±SEM) in the AbAo of 6 siCtl-treated WT mice, 8 siAdamts1-treated WT mice, 5 siCtl-treated Nos2−/− mice, and 5 siAdamts1-treated Nos2−/− mice. (e) RT-qPCR analysis of Nos2 mRNA in extracts form VSMCs transduced with siCtl or siAdamts1 (mean±SEM, n=3 mice per group). Student's t-test, p<0.01. (f) Representative immunoblot analysis of Nos2 (n=4 per group), p-Akt-5473 (n=3 per group), Akt (n=3 per group), p-p65-5536 (n=3 per group), and p65 (n=3 per group) in extracts from VSMCs transduced with siCtl or siAdamts1. Tubulin (n=4 per group) was used as loading control. (g) Representative immunoblot analysis (n=3 per group) of Nos2, pAkt-S473, and Akt in extracts from VSMCs transduced with siCtl or siAdamts1 and treated with the mTOR inhibitor AZD8055 as indicated. (h) Nitrites and Nitrates (total NOx) quantitation in conditioned media from VSMCs transduced with siCtl or siAdamts1 and treated with the Nos2 inhibitor 1400w as indicated. 8 untreated and 6 treated siCtl mice, and 8 untreated and 6 treated siAdamts1 mice. (i) Representative images (n=3 per group) of NO production (red), and GFP fluorescence (green) in unfixed VSMCs transduced with siCtl or siAdamts1 and treated with the Nos2 inhibitor 1400w as indicated. Bar, 50 µm.

Figure 14:
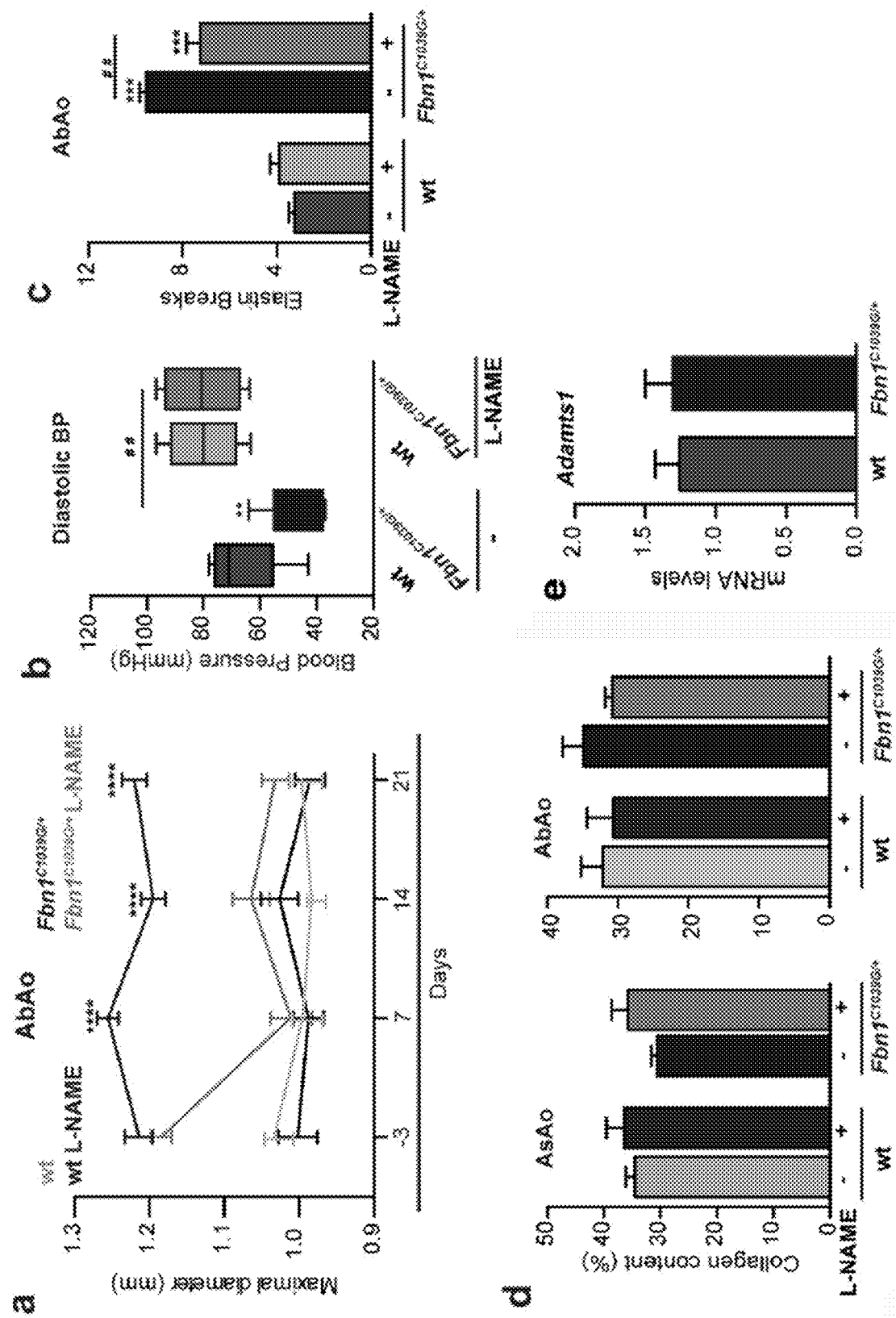
Figure 14:
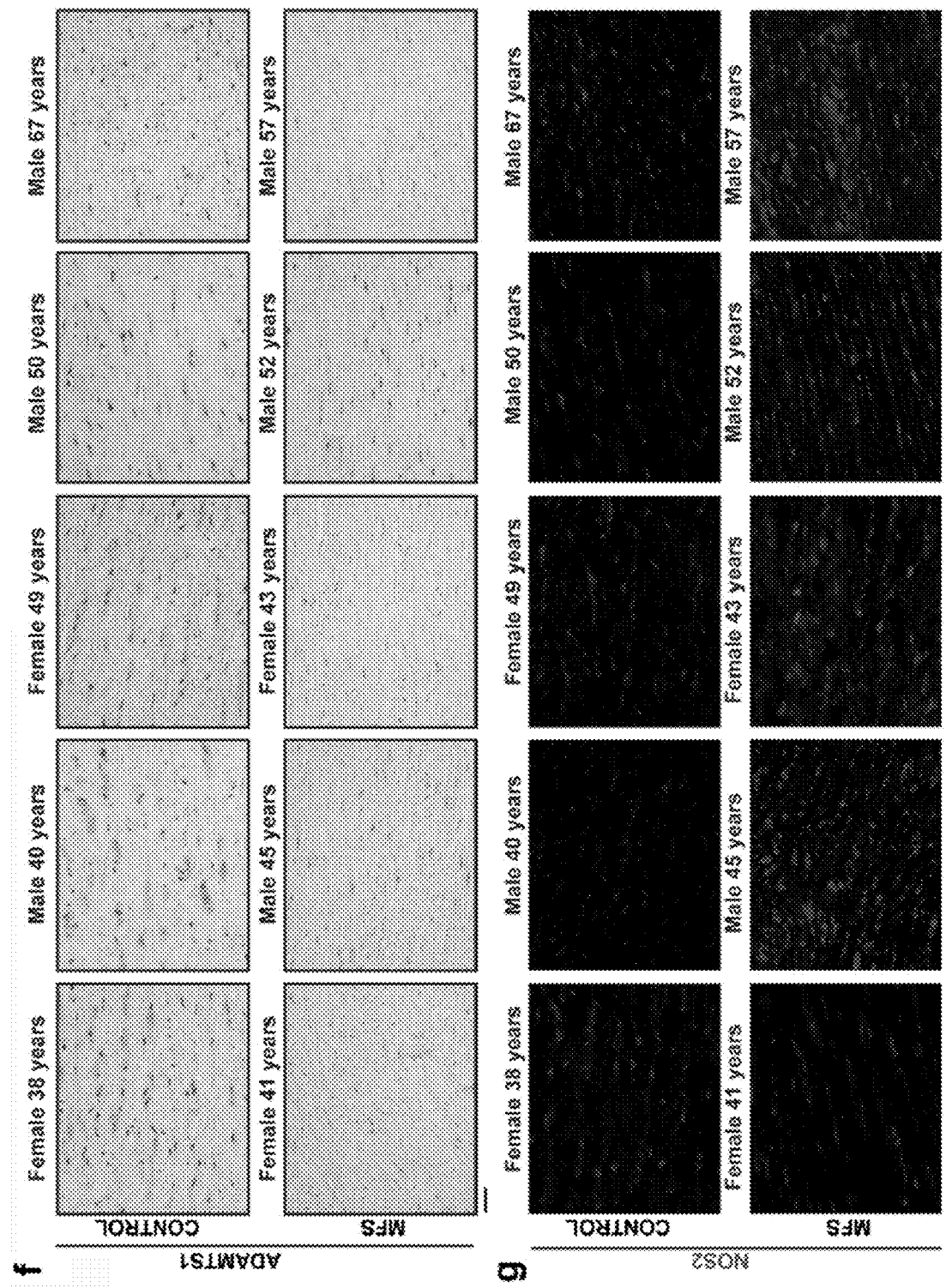
Figure 14:
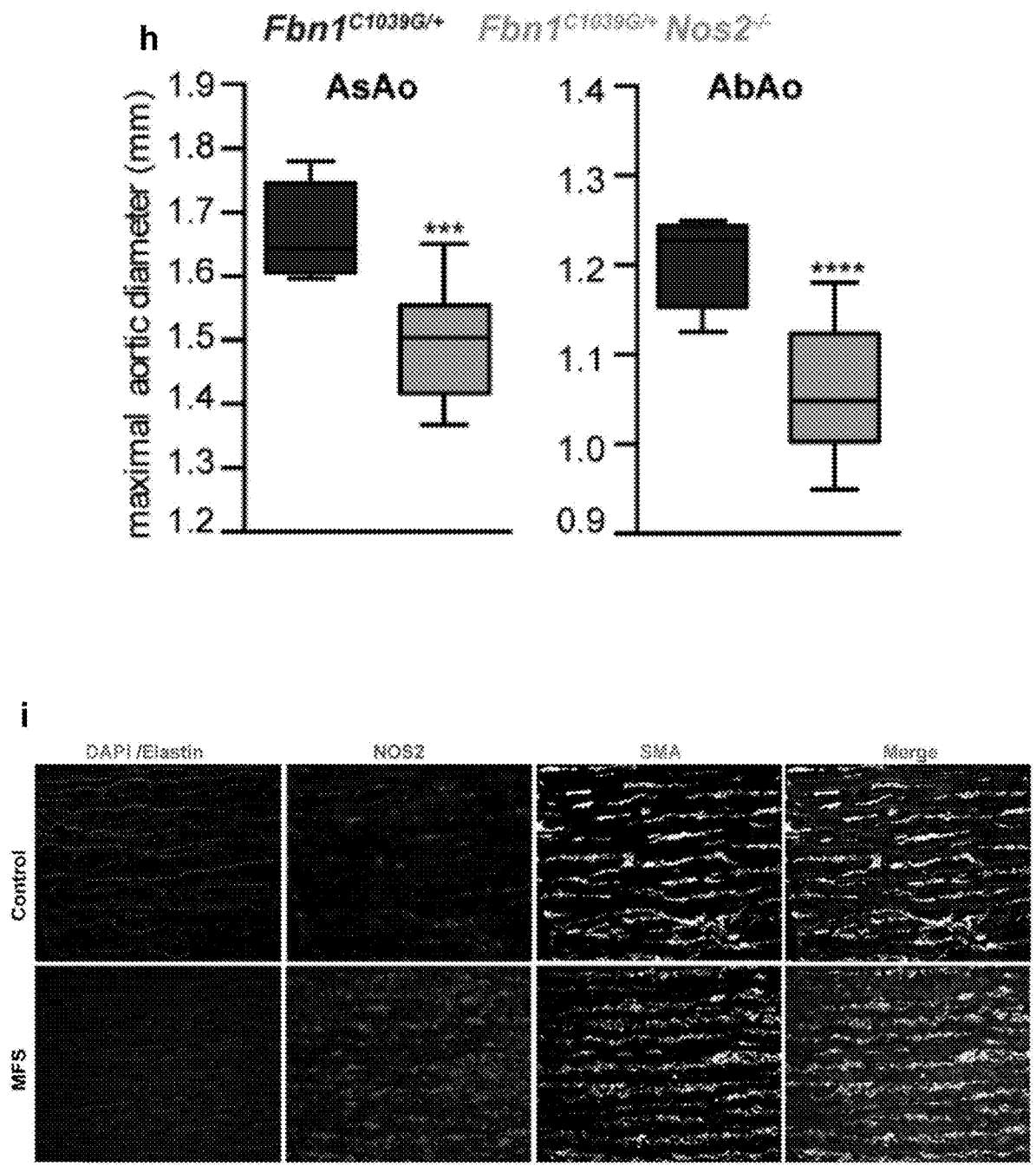

FIG. 14. (a) Maximal AbAo diameter (mean±SEM) at the indicated times in 9 wt, 7 wt L-NAME, 8 Fbn1C1039G/+, and 8 Fbn1C1039G/+L-NAME mice. Two-way ANOVA, **p<0.0001 vs Fbn1C1039G/+L-NAME. (b) End-of-experiment quantification of diastolic BP in the same mice. One-way ANOVA, <0.01 vs untreated wt; ##p<0.01 control vs L-NAME. End-of-experiment quantification of (c) elastin breaks in the AbAo and (d) collagen content in AsAo and AbAo in 6 wt, 3 wt L-NAME, 3 Fbn1C1039G/+, and 5 Fbn1C1039G/+L-NAME mice. One-way ANOVA; *p<0.001, vs untreated wt; ##p<0.01, untreated vs L-NAME. (e) RTqPCR analysis of Adamts1 mRNA in aortic extracts from 6 wt and 3 Fbn1C1039G/+ mice. (f) Representative medial layer images of ADAMTS1 immunohistochemistry in aortic cross sections of human samples from 5 healthy donors and 9 MFS patients. Bar, 25 µm. (g) Representative medial layer images of NOS2 immunofluorescence (red; n=6) and DAPIstained nuclei (blue) in sections from 5 control donors and 8 MFS patients. Bar, 25 µm. (h) The ADAMTS1-NOS2 axis is deregulated in aortic samples of human MFS. Maximal AsAo and AbAo diameter (mean±SEM) of 8 Fbn1C1039G/+ and 14 Fbn1C1039G/+; Nos2−/− at 12 weeks of age. Student's t-test, *p<0.001, ****p<0.0001.(i) The ADAMTS1-NOS2 axis is deregulated in aortic samples of human MFS. Representative medial layer images of NOS2 (red) and SMA (white) immunofluorescence, elastin autofluorescence (green), and DAPI-stained nuclei (blue) in sections from 5 control donors and 8 MFS patients. Bar, 25 μm.

Figure 15:
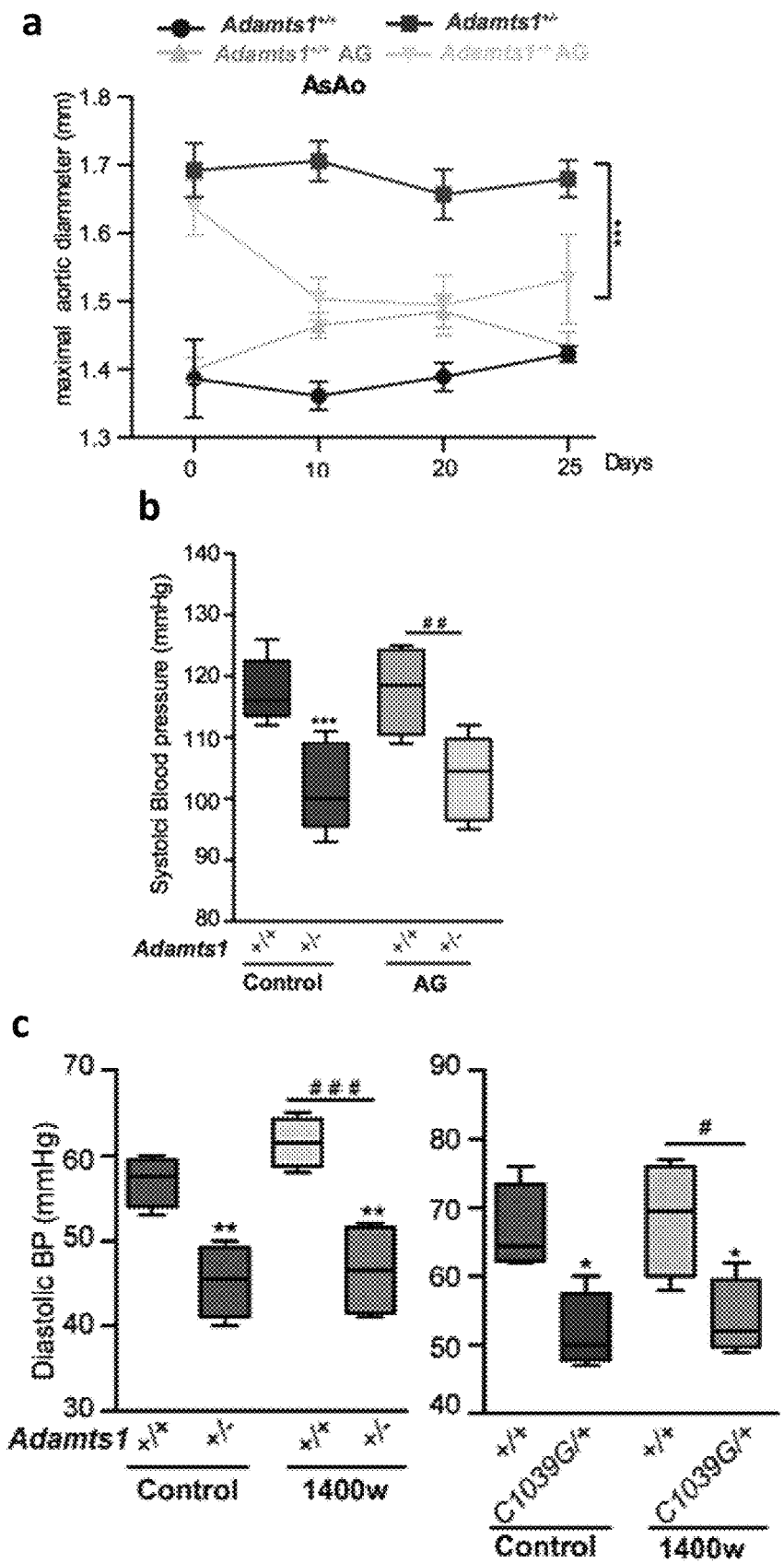
Figure 15:
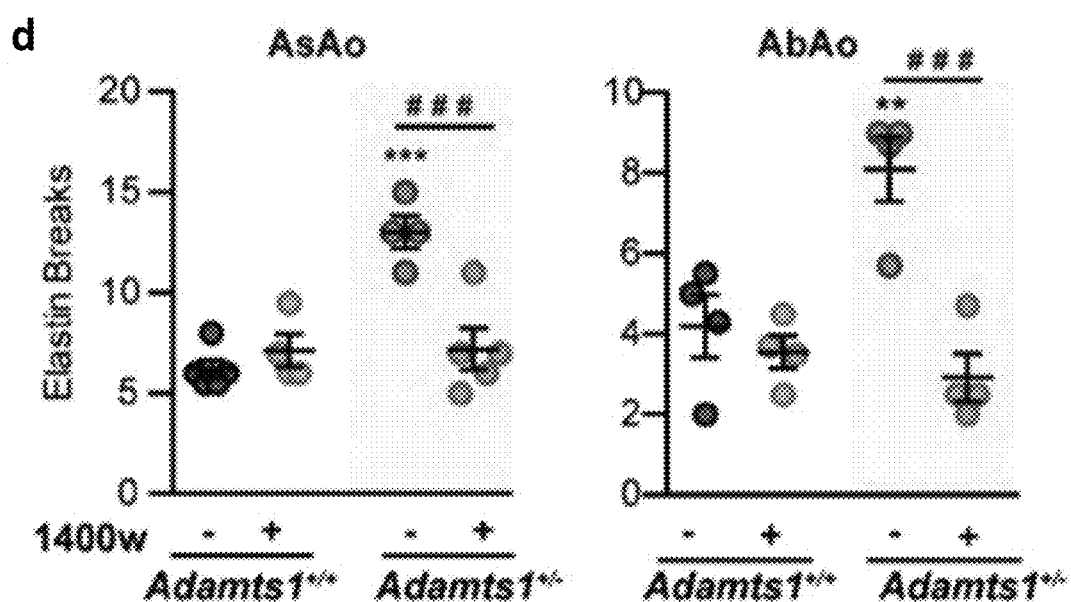

FIG. 15. (a) The Nos2 inhibitor aAminoguanidine (AG), reduces aortic diameter in Adamts1+/− mice. Ascending and abdominalaorta diameter (mean±SEM) from Adamts1+/+ (n=4) and Adamts1+/− (n=5) treated with or without AG (1.5 gr/1 in drinking water). Repeated-measurements two-way ANOVA *p<0.001 and p<0.001. (b) The Nos2 inhibitor aAminoguanidine (AG), reduces aortic diameter in Adamts1+/− mice. Systolic blood pressure (mean±SEM) from mice shown in (a). One-way ANOVA, *p<0.001 control Adamts1+/+ vs Adamts1+/−; ##p<0.01 AG treated Adamts1+/+ vs Adamts1. (c) End-of-experiment quantification of diastolic BP in the same mice. Two-way ANOVA, *p<0.05, **p<0.01 vs untreated wt; #p<0.05 ###p<0.001. and (d) quantification of elastin breaks (mean±SEM) in the same cohort of animals. Scale bar, 50 μm. Two-way ANOVA, *p<0.05 p<0.01, *p<0.001, ****p<0.0001 vs untreated wt; ###p<0.001.

Figure 16:
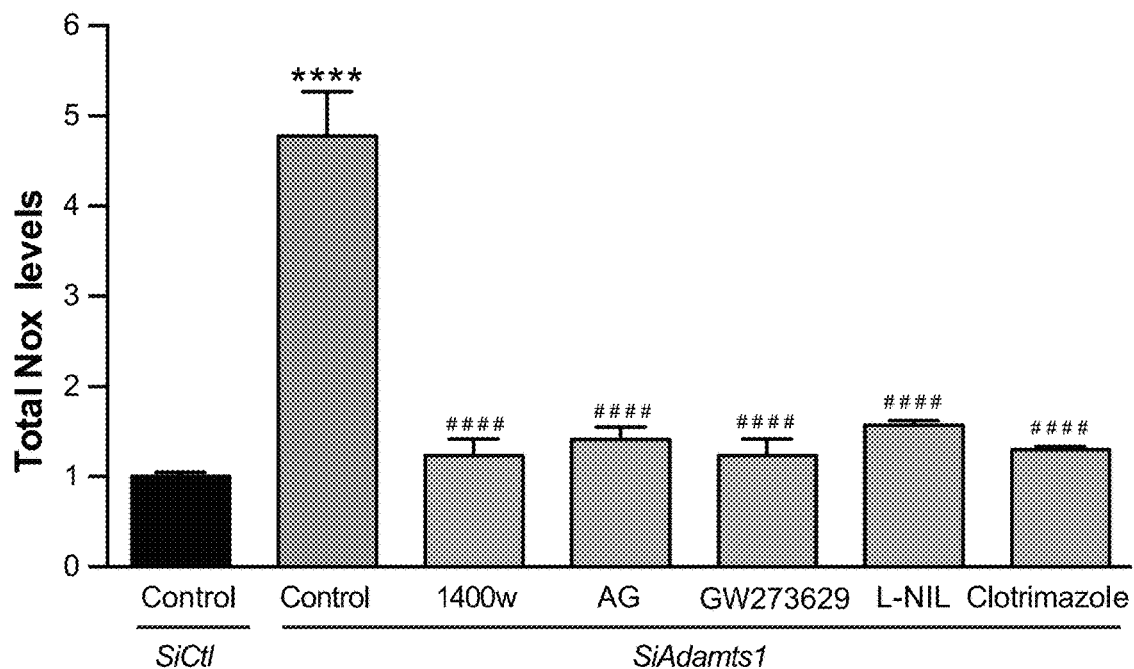

FIG. 16. Nitrites and Nitrates (total NOx) quantitation in conditioned media from VSMCs transduced with siCtl or siAdamts1 lentivirus and treated with the Nos2 inhibitors: 1400W (2 μm), Aminoguanidine (AG) (10004), GW273629 (20 μm), 1-NIL (3 mM), Clotrimazole (20 μM) as indicated. Data are means±s.e.m; n=4 per group; ****P<0.0001 (versus Control-siCTL), ####P<0.0001 (versus Control-siAdamts1).

Figure 17:
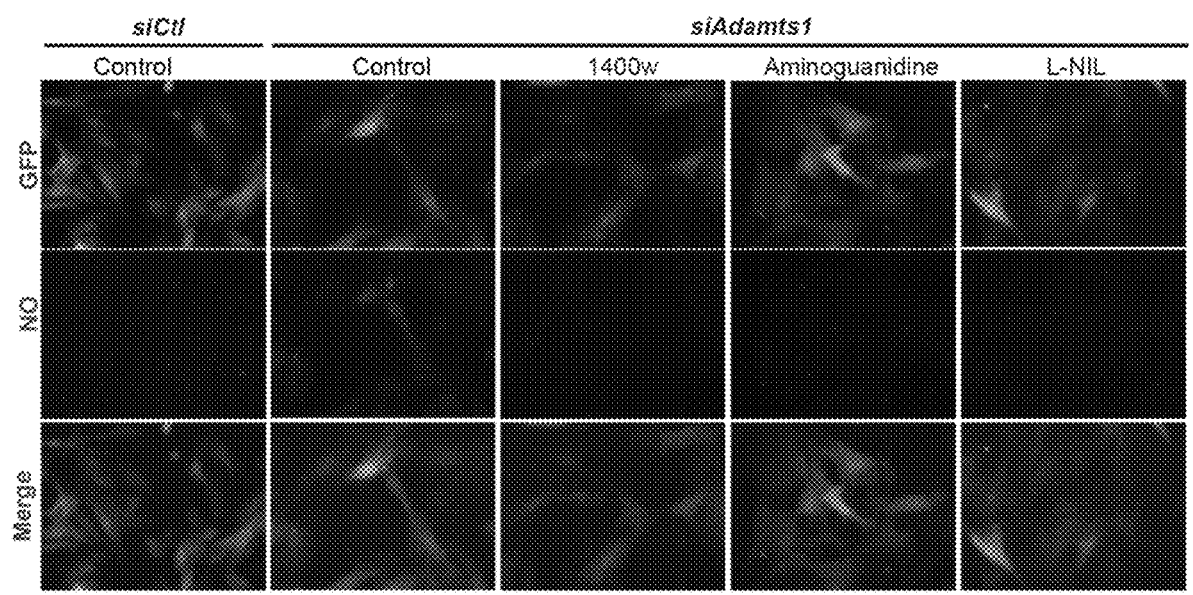

FIG. 17. Representative images (n=4) of NO production (red) and GFP fluorescence (green) in unfixed VSMCs transduced with siCtl or siAdamts1 and treated with the Nos2 inhibitors as indicated. Bar, 50 μm.

Figure 18:
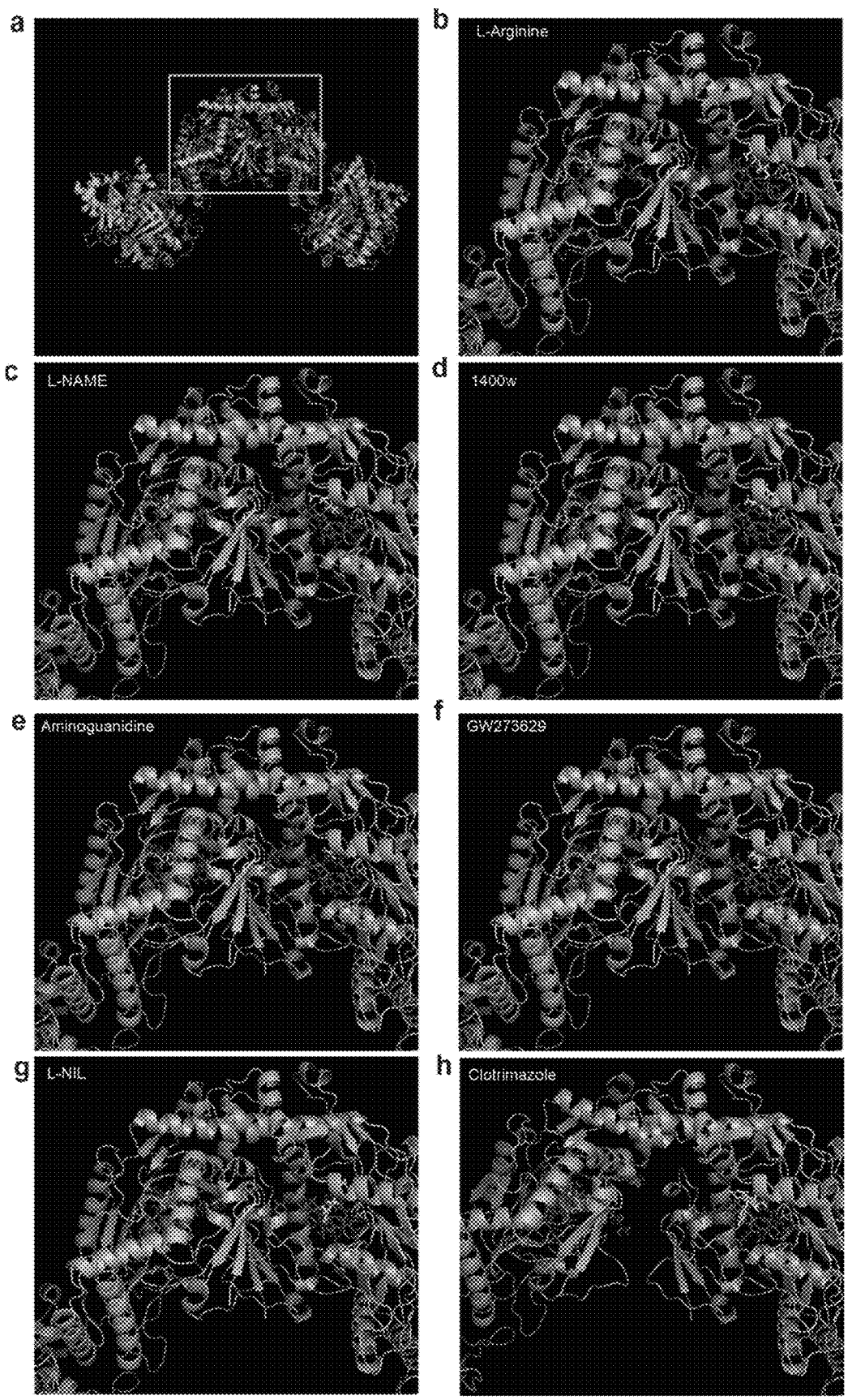

FIG. 18. 3D view of the NOS2 structure, ligands and inhibitors binding sites. (a) Human NOS2 structure and native ligands and (b), zoom of the dimer interface and the ligands region, showing the A (green) and B (cyan) chains of the human NOS2 as cartoon and the native ligands (Hemo and H4B in red and L-Arginine in yellow) as sticks. All the inhibitors models bind in the guanidine site of the ligand region (in yellow as sticks). The binding site for L-NAME in (c), 1400w in (d), Aminoguanidine in (e), GW273629 in (f), L-NIL in (g) and Clotrimazole in (h) are shown. In the case of Clotrimazole, as reported previously, inhibits the dimerization of NOS2 modifying the dimer interface.

DETAILED DESCRIPTION OF THE INVENTION

Definitions

The terms "nitric oxide synthase" and "NOS" as used interchangeably herein refer to any of the isoforms of isoforms of the enzyme nitric oxide synthase, including eNOS, nNOS and iNOS.

The terms "inducible nitric oxide synthase," "NOS-2" and "iNOS" as used interchangeably herein refer to the $Ca^{+2}$-independent, inducible isoform of the enzyme nitric oxide synthase.

The terms "nitric oxide synthase inhibitor" and "NOS inhibitor" as used interchangeably herein denote a compound that reduces the physiological effect of a nitric oxide synthase enzyme. Such an inhibitor may be selective for a particular isoform of nitric oxide synthase, or may be substantially non-selective, that is, effective to a large extent on two or more isoforms of nitric oxide synthase.

The terms "selective nitric oxide synthase inhibitor" and "selective NOS inhibitor" denote a compound capable of reducing the physiological effect of a particular isoform of nitric oxide synthase preferentially over other isoforms of nitric oxide synthase.

The terms "selective inducible nitric oxide synthase inhibitor," "selective NOS-2 inhibitor," and "selective NOS inhibitor" denote a compound capable of reducing the physiological effect of the calcium ion independent isoform of nitric oxide synthase preferentially over other isoforms of nitric oxide synthase. In one embodiment, a selective iNOS inhibitor produces the selective inhibition of iNOS compared to either endothelial NOS or neuronal NOS such that in vivo administration results in efficacy ($ED_{50}$) of less than 100 mg/kg. In another embodiment, a selective iNOS inhibitor produces the selective inhibition of iNOS compared to either endothelial NOS or neuronal NOS such that in vivo administration results in efficacy ($ED_{50}$) of less than 10 mg/kg in a rodent endotoxin model). In a further embodiment, an iNOS inhibitor exhibits selectivity of about 20-fold with respect to eNOS as measured by elevation in mean arterial blood pressure. In yet another embodiment, an iNOS inhibitor exhibits 100-fold or greater selectivity fold with respect to eNOS as measured by elevation in mean arterial blood pressure. In still another embodiment, an iNOS inhibitor exhibits selectivity of at about 20-fold with respect to nNOS as measured by reductions in gastrointestinal transit or penile erection. In another embodiment, an iNOS inhibitor exhibits about 100-fold or greater selectivity with respect to nNOS as measured by reductions in gastrointestinal transit or penile erection.

The term "screening" is understood as the examination or testing of a group of individuals pertaining to the general population, at risk of suffering from a thoracic aortic aneurysm (TAA) as defined below, with the Objective of discriminating healthy individuals from those who are suffering from an undiagnosed thoracic aortic aneurysm (TAA) or who are at high risk of suffering from said indications.

The term "thoracic aortic aneurysm (FAA)" includes the well-accepted medical definition that defines TAA as a localized pathologic dilatation of the thoracic segment of the aortic wall at least 50%>normal, true aneurysm contains all layers of vessel wall. The present invention includes diseases that results in a TAA such as Syndromic thoracic aortic aneurysm (TAA) such as Marfan Syndrome, vascular Ehlers Danlos, Loeys Dietz Syndrome (Types 1 and 2), and Familial thoracic aortic aneurysm and dissection (familial TAAD); non-syndromic TAAs; or any other disease associated with an aorthopathy triggered by Adamts1 deficiency. Non-syndromic thoracic aortic aneurysm (TA) includes those diseases not understood as syndromes that result in a thoracic aortic aneurysm (TAA). The present invention also comprises diseases that result in TAA such as bicuspid aortic valve, wherein Adamts1 null mice develop biscuspid aortic valve in most cases.

The expression "minimally-invasive biological sample" refers to any sample which is taken from the body of the patient without the need of using harmful instruments, other than fine needles used for taking the blood from the patient, and consequently without being harmfully for the patient. Specifically, minimally-invasive biological sample refers in the present invention to: blood, serum, or plasma samples.

The term "up-regulated" or "over-expressed" of any of the biomarkers or combinations thereof described in the present invention, refers to an increase in their expression level with respect to a given "threshold value" or "cutoff value" by at least 5%, by at least 10%, by at least 15%, by at least 20%, by at least 25%, by at least 30%, by at least 35%, by at least 40%, by at least 45%, by at least 50%, by at least 55%, by at least 60%>, by at least 65%>, by at least 70%, by at least 75%, by at least 80%, by at least 85%, by at least 90%, by at least 95%, by at least 100%, by at least 110%, by at least 120%, by at least 130%, by at least 140%, by at least 150%, or more. In addition, the term up-regulated" or "over-expressed" of any of the biomarkers or combinations thereof described in the present invention, also refers to an increased in their expression level with respect to a given "threshold value" or "cutoff value" by at least about 1.5-fold, about 2-fold, about 5-fold, about 10-fold, about 15-fold, about 20-fold, about 50-fold, or of about 100-fold.

The term "Adamts1" refers to the A disintegrin and metalloproteinase with thrombospondin motifs 1, in particular an enzyme that in humans is encoded by the ADAMTS1 gene.

The term "reduced expression" of any of the biomarkers or combinations thereof described in the present invention, refers to a reduction in their expression level with respect to a given "threshold value" or "cutoff value" by at least 5%, by at least 10%, by at least 15%, by at least 20%, by at least 25%, by at least 30%, by at least 35%, by at least 40%, by at least 45%, by at least 50%, by at least 55%, by at least 60%>, by at least 65%>, by at least 70%, by at least 75%, by at least 80%, by at least 85%, by at least 90%, by at least 95%, by at least 100%, by at least 110%, by at least 120%, by at least 130%, by at least 140%, by at least 150%, or more. In addition, the term "reduced expression" of any of the biomarkers or combinations thereof described in the present invention, also refers to a decreased in their expression level with respect to a given "threshold value" or "cutoff value" by at least about 1.5-fold, about 2-fold, about 5-fold, about 10-fold, about 15-fold, about 20-fold, about 50-fold, or of about 100-fold.

The term "threshold value" or "cutoff value", when referring to the expression levels of Adamts1 or iNOS described in the present invention, refers to a reference expression level indicative that a subject is likely to suffer from a syndromic or nonsyndromic thoracic aortic aneurysm (TAA) with a given sensitivity and specificity if the expression levels of the patient are above or below said threshold or cut-off or reference levels. In the context of the present invention, said "threshold value" or "cutoff value" is a reference expression level taken from a healthy subject.

A variety of statistical and mathematical methods for establishing the threshold or cutoff level of expression are known in the prior art. A threshold or cutoff expression level for a particular biomarker may be selected. One of skill in the art will appreciate that these threshold or cutoff expression levels can be varied, for example, by moving along the ROC plot for a particular biomarker or combinations thereof, to obtain different values for sensitivity or specificity thereby affecting overall assay performance. For example, if the objective is to have a robust diagnostic method from a clinical point of view, we should try to have a high sensitivity. However, if the goal is to have a cost-effective method we should by to get a high specificity. The best cutoff refers to the value obtained from the ROC plot for a particular biomarker that produces the best sensitivity and specificity. Sensitivity and specificity values are calculated over the range of thresholds (cutoffs). Thus, the threshold or cutoff values can be selected such that the sensitivity and/or specificity are at least about 70%, and can be, for example, at least 75 at least 80%, at least 85 at least 90%, at least 95 at least 96%, at least 97 at least 98%, at least 99% or at least 100% in at least 60% of the patient population assayed, or in at least 65%, 70%, 75 or 80% of the patient population assayed.

As used herein, the expression "C1-6 alkyl" includes methyl and ethyl groups, and straight-chained or branched propyl, butyl, pentyl and hexyl groups. Particular alkyl groups are methyl, ethyl, n-propyl, isopropyl and Cert-butyl. Derived expressions such as "C1-6alkoxy", "C1-6alkoxyC1-6alkyl", "hydroxyC1-6alkyl", "C1-6alkylcarbonyl", "C1-6alkoxycarbonylC1-6alkyl", "C1-alkoxycarbonyl", "aminoC1-6alkyl", "C1-6alkylcarbarnoylC1-6alkyl", "C1-6dialkylcarbamoylC1-6alkyl" "mono- or di-C1-6alkylaminoC1-6alkyl", aminoC1-6alkylcarbonyl", "diphenylC 1-6alkyl", "arylC1-6alkyl", "arylcarbonylC1-6alkyl" and "alkyloxyC1-6alkyl" are to be construed accordingly.

As used herein, the expression "C2-6alkenyl" includes ethenyl and straight-chained or branched propenyl, butenyl, pentenyl and hexenyl groups. Similarly, the expression "C2-6alkynyl" includes ethynyl and propynyl, and straight-chained or branched butynyl, pentynyl and hexynyl groups.

As used herein "aryl" represents a carbocyclic aromatic ring system such as phenyl, biphenyl, naphthyl, anthracenyl, phenanthrenyl, fluorenyl, indenyl, pentalenyl, azulenyl, biphenylenyl and the like. Aryl is also intended to include the partially hydrogenated derivatives of the carbocyclic aromatic systems enumerated above. Non-limiting examples of such partially hydrogenated derivatives are 1,2,3,4-tetrahydronaphthyl, 1,4-dihydronaphthyl and the like.

As used herein "aryloxy" represents a group —O-aryl wherein aryl is as defined above.

As used herein "heteroaryl" (on its own or in any combination, such as "heteroaryloxy", or "heteroaryl alkyl")—a 5-10 membered aromatic ring system in which one or more rings contain one or more heteroatoms selected from the group consisting of N, O or S, such as, but not limited, to pyrrole, pyrazole, furan, thiophene, quinoline, isoquinoline, quinazolinyl, pyridine, pyrimidine, oxazole, thiazole, thiadiazole, tetrazole, triazole, imidazole, or benzimidazole.

As used herein "heterocyclic or heterocyclyl." (on its own or in any combination, such as "heterocyclylalkyl")—a saturated or partially unsaturated 4-10 membered ring system in which one or more rings contain one or more heteroatoms selected from the group consisting of N, O, or S; such as, but not limited to, pyrrolidine, piperidine, piperazine, morpholine, tetrahydro pyran, or imidazolidine.

As used herein, the expression "C1-6 perfluoroalkyl" means that all of the hydrogen atoms in said alkyl group are replaced with fluorine atoms. Illustrative examples include trifluoromethyl and pentafluoroethyl, and straight-chained or branched heptafluoropropyl, nonafluorobutyl, undecafluoropentyl and tridecafluorohexyl groups. Derived expression, "C1-6 perfluoroalkoxy", is to be construed accordingly.

As used herein, the expression "C3-8cycloalkyl" means cyclopropyl, cyclobutyl, cyclopentyl, cyclohexyl, cycloheptyl and cyclooctyl.

As used herein, the expression "C3-8cycloalkylC1-6alkyl" means that the C3-8cycloalkyl as defined herein is further attached to C1-6alkyl as defined herein. Representative examples include cyclopropylmethyl, 1-cyclobutylethyl, 2-cyclopentylpropyl, cyclohexylmethyl, 2-cycloheptylethyl and 2-cyclooctylbutyl and the like.

As used herein "halogen" or "halo" means chloro, fluoro, bromo, and iodo.

As used herein "C1-6alkylsulfonyl" in the present context designates a group —S(=O)2C1-6alkyl wherein C1-6alkyl is as defined above. Representative examples include, but are not limited to, methylsulfonyl, ethylsulfonyl, n-propylsulfonyl, isopropylsulfonyl, butylsu Ifonyl, iso-butylsulfonyl, sec-butylsulfonyl, tert-butylsulfonyl, n-pentylsulfonyl, isopentylsulfonyl, neopentylsulfonyl, tert-pentylsulfonyl, n-hexylsulfonyl, isohexylsulfonyl and the like.

As used herein "arylsulfonyl" represents a group —S(=O)2aryl wherein aryl is as defined above.

As used herein "heteroarysulfonyl" represents a group —S(=O)2heteroaryl wherein heteroaryl is as defined above.

As used herein, "patient" means a warm blooded animal, such as for example rat, mice, dogs, cats, guinea pigs, and primates such as humans.

As used herein, the expression "pharmaceutically acceptable carrier" means a non-toxic solvent, dispersant, excipient, adjuvant, or other material which is mixed with the compound of the present invention in order to permit the formation of a pharmaceutical composition, i.e., a dosage form capable of administration to the patient. One example of such a carrier is a pharmaceutically acceptable oil typically used for parenteral administration.

The term "pharmaceutically acceptable salts" as used herein means that the salts of the compounds of the present invention can be used in medicinal preparations. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, hydrobromic acid, sulfuric add, methanesulfonic acid, 2-hydroxyethanesulfonic acid, p-toluenesulfonic acid, fumaric acid, maleic acid, hydroxymaleic acid, malic acid, ascorbic acid, succinic acid, glutaric acid, acetic acid, salicylic acid, cinnamic acid, 2-phenoxybenzoic acid, hydroxybenzoic acid, phenylacetic acid, benzoic acid, oxalic acid, citric acid, tartaric acid, glycolic acid, lactic add, pyruvic acid, malonic acid, carbonic add or phosphoric acid. The acid metal salts such as sodium monohydrogen orthophosphate and potassium hydrogen sulfate can also be formed. Also, the salts so formed may present either as mono- or di-acid salts and can exist either as hydrated or can be substantially anhydrous. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

"Substituted" means substituted by 1 to 2 substituents independently selected from the group consisting of C1-6 alkyl, C1-6 perfluoroalkyl, hydroxy, —CO2H, an ester, an amide, C1-C6 alkoxy, C1-C6 perfluoroalkoxy, NH2, Cl, Br, I, F, NH-lower alkyl, and —N(lower alkyl)2.

"Therapeutically effective amount" means an amount of e compound which is effective in treating the named disorder or condition.

The term "comprising" it is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

It is also noted that the term "kit" as used herein is not limited to any specific device and includes any device suitable for working the invention such as but not limited to microarrays, bioarrays, biochips or biochip arrays.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

DESCRIPTION

The present invention identifies the NO pathway, in particular iNOS, as an essential mediator of aortic disease in mouse models and suggests such pathway as a possible target for intervention in thoracic aortopathies, in particular in human TAAs. In addition, we show that Adamts1 is an important mediator of vascular wall homeostasis whose expression is decreased in thoracic aortic aneurysms, in particular in syndromic thoracic aortic aneurysms (TAA), more particularly in MFS. In fact, the resemblance of the aortopathy in Adamts1-deficient mice to human syndromic FTAAD suggests that the ADAMTS1 downregulation in MFS may underlie the aortic phenotype of MFS patients.

The authors of the present invention previously reported that lentivirus tropism depends on the administration route and that injection into the jugular vein yields stable and efficient transduction of the aortic wall. This approach achieves long-term silencing of Adamts1 throughout the aorta, and provides an alternative to the use of genomically modified mice for the analysis of genes expressed in the vascular wall. The silencing model results in aortic phenotypic changes and symptoms indistinguishable from those of Adamts1+/− mice. A key experimental benefit of lentiviral silencing is the controlled timing of gene targeting. Achieving this in the aortic wall with a conditional knockout approach would require simultaneous use of specific drivers for the 3 major cell types, and would not be viable. In contrast, a single lentivirus type knocks down gene expression in all vascular wall cells. Moreover, timed knockdown provides a unique model for studying aortic disorders, enabling us to define the pathological sequence leading to disease: siAdamts1 transduction triggered immediate hypotension and elastolysis, followed rapidly by aortic dilation, whereas the TGFβ-Smad pathway was not activated until 1-2 weeks after lentiviral infection.

Although aortic medial degeneration and dilation are associated with activation of the TGFβ and AngII pathways in syndromic and non-syndromic aortic disease, blockade of these pathways had no significant effect on siAdamts1- mediated aortic dilation, medial degeneration or hypotension, at least in the first 2 weeks of disease. Our data are nonetheless compatible with a role for these pathways at later stages. In this regard, TGFβ neutralization also failed to inhibit aneurysm progression at the early stages of a progressively severe form of MFS (Fbn1mgR/mgR mice), but was protective at later stages.

Hypertension is considered a risk factor in AA; however, our results show that the hypertensive effects of L-NAME are compatible with reversal of aortic dilation in Adamts1+/− and MFS mice. Reversal of dilation was remarkably fast, being complete in 1 week. Elastic fiber and collagen deposition in these mice returned to normal levels 3 weeks after NOS inhibition, suggesting activation of mechanisms for collagen clearance from the aortic wall and the induction of elastin synthesis. We used NOS inhibitors in 3-4-month-old mice, and their therapeutic effect in older mice has yet to be determined. Nonetheless, our results clearly indicate that NO is a primary trigger of aortic diseases and is also required to sustain their symptoms.

Previous reports implicating NO in mouse models of cerebral and abdominal AA provide contradictory data, often related to pharmacological versus targeted genetic deletion approaches. For example, inhibitory or stimulatory roles for Nos2 have been reported in models of AAA. In cerebral aneurysm, results with pharmacological inhibitors indicate that Nos2 is critical for disease development; however, Nos2−/− and wt mice have a similar incidence of cerebral aneurysm. In our analysis, the genetic studies support the results obtained with L-NAME: Nos2−/− mice were resistant to siAdamts1-triggered aortopathy. The pathological role of NO in this model is thus mediated by Nos2, which is induced as early as 2 days after Adamts1 silencing. It is important to note that although Nos2 is not normally expressed in resting cells, once induced, it remains highly active. We show high Nos2 protein in 2 mouse models of Adamts1 deficiency, in MFS mice and, more importantly, in aortic sections of MFS patients. Together our results indicate that NOS2-mediated NO production plays an essential role in the pathogenesis of TAA, in particular in the pathogenesis of syndromic thoracic aortic aneurysms (TAA), in particular in MFS and the aortopathy triggered by Adamts1 deficiency.

Thus a first aspect of the present invention refers to a composition useful in a method for the treatment, prevention or inhibition of a thoracic aortic aneurysm (TAA) in a subject in need of such treatment, prevention or inhibition, comprising administering to said subject an iNOS blocker/inhibitor or a pharmaceutically acceptable salt or prodrug thereof. It is important to note that the method of the first aspect of the invention is useful no matter if the subject has been diagnosed with TAA or at risk of developing TAA according to the methodology described later-on in the present invention or if the subject has been diagnosed with TAA or at risk of developing TAA with any other known clinically effective methodology.

It is further noted that TAAs can be subdivided into syndromic presentations that exhibit prominent features of systemic connective tissue disease (such as Marfan syndrome, ADESAD (Adamts1-deficiency elicited syndromic aortic disease (ADESAD)) and Loeys-Dietz syndrome (LDS)) and non-syndromic presentations, such as bicuspid aortic valve with TAA and isolated familial TAA. The authors of the present invention have clearly illustrated throughout the present specification, in particular in FIGS. 6m and 6o, that iNOS inhibitors are useful as a medical therapy directed at preventing, limiting and reverting the progressive TAA expansion in two syndromic presentations, in particular in Marfan and ADESAD. In addition, please note that it is well known that syndromic presentations in general present similar attributes in terms of disease development and subsequent progression, in particular they all develop with medial degeneration, which is characterized by elastic fibers fragmentation, among other features; it thus appears more than plausible that a medical treatment that works well in two syndromic presentations reverting common attributes such as medial degeneration would also work in other syndromic presentations such as Loeys-Dietz syndrome (LDS) (see FIGS. 4h, 4i (elastin breaks and fibrosis, respectively, in ADESAD) (please also refer to FIGS. 6o, 6h and 6j). As regards non-syndromic presentations, such as bicuspid aortic valve with TAA and isolated familial TAA, the authors of the present invention have created an animal model for non-syndromic presentations of the disease (please refer to FIGS. 2e, 2f, and 2g wherein medial degeneration and aortic dilation is shown in this model). In addition, FIGS. 4b, 4c, 4d, 5d, 5e and 5f illustrate that treatment with iNOS inhibitors prevents aortic dilation and medial degeneration in such non-syndromic presentation model and that iNOS knock-out mice in said non-syndromic presentation of the disease do not develop media degeneration or aortic dilation.

We thus honestly believe that the evidence provided in the present specification demonstrates the usefulness of iNOS inhibitors as a medical therapy directed at preventing, limiting and reverting the progressive TAA expansion in syndromic and non-syndromic presentations of the disease. Consequently, the present specification demonstrates the usefulness of iNOS inhibitors in the treatment of TAA.

In a preferred aspect of the invention, the iNOS inhibitor is capable of binding in the guanidine site of the L-arginine ligand region of the human NOS2 structure and inhibiting the human NOS2 isoform in the presence of L-arginine. In this sense, we have further depicted the expression "iNOS inhibitors" by characterizing these by their capacity to bind the guanidine site of the L-arginine ligand region of the human NOS2 structure and inhibiting the human NOS2 isoform in the presence of L-arginine. Please note that from the early days of drug discovery it has been known that molecules of different structural types can elicit the same biological action. In the present case and as illustrated throughout the specification, structurally diverse compounds bind to the common target in the same way as illustrated in FIG. 18, they all inhibit the human NOS2 isoform in the presence of L-arginine and reduced the expression of NO as illustrated in FIG. 17 or FIG. 61 for 1400W, aminoguanidine (FIGS. 15a and 15b), L-Name (FIG. 4b), GW273629, L-NIL and Clotrimazole (FIG. 16). Consequently, there is no doubt that all iNOS inhibitors falling within the scope of claim 2 should be useful in the implementation of the present invention.

In another preferred embodiment of the first aspect, the iNOS inhibitor comprises the following chemical moiety covalently bounded through R2 to the rest of the chemical compound:

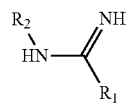

wherein R1 is a methyl, methlyamine or amino group and wherein R2 is an amino group or methylene group.

Preferably, the iNOS blocker/blocker is an iNOS selective inhibitor. More preferably, the iNOS inhibitor is selected from the group consisting of 1400W, L-NAME, BYK191023, GW274150, GW273629, MEG (sodium succinate), Aminoguanidine (AG) hydrocloride, L-Canavanine, S-(2-Aminoethyl)-ITU dihydrobromide, 2-Iminopiperidine hydrochloride, 1-Amino-2-hydroxyguanidine, p-Toluene-sulfonate, 1,3-BP-ITU dihydrobromide, 2-Amino-4-methylpyridine, S-Methylisothiourea sulfate, Canavanine sulfate, MEG(sulfate), AMT hydrochloride, L-NIL dihydrochloride, 1,3-PBITU, Dihydrobromide, S-(3-Aminopropyl)-ITU dihydrobromide, S-Isopropylisothiourea hydrobromide, Propenyl-L-NIO (hydrochloride), 2-Imino-4-methylpiperidine acetate, N-Benzylacetamide Hydrobromide, 2-Imino-4,6-dimethylpiperidine, a coumarin or is represented by the formula:

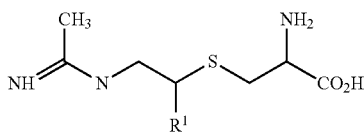

wherein R1 is selected from C1-4 alkyl, C3-4 cycloalkyl, C1-4 hydroxyalkyl, and C1-4 haloalkyl or or a pharmaceutically acceptable salt thereof.

Some of the compounds referred to above, are represented herein below:

L-NMA

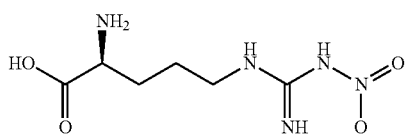

L-NMMA

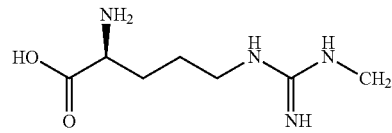

7-M

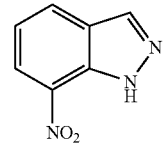 [SMILES: O=[N+]([O-])c1cccc2cn[nH]c12]

ARL 17177

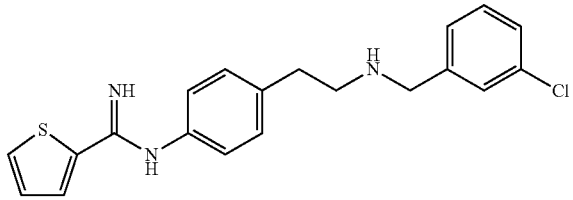 [SMILES: N=C(Nc1ccc(CCNCc2cccc(Cl)c2)cc1)c1cccs1]

Aminoguanidine

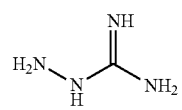

L-NIL

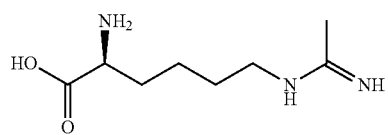

1400W

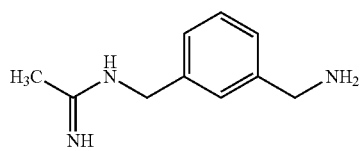

-continued

GW273629

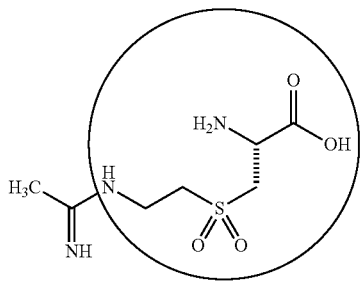

GW274150

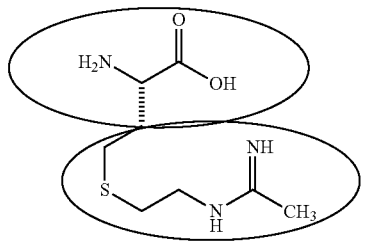

In a preferred embodiment of the first aspect of the invention, said iNOS inhibitor is selected from the group consisting of:
S—((R)-2-(1-iminoethylamino)propyl)-L-cysteine;
S—((S)-2-(1-iminoethylamino)propyl)-L-cysteine;
S—((R/S)-2-(1-iminoethylamino)propyl)-L-cysteine;
S—((R)-2-(1-iminoethylamino)propyl)-D-cysteine;
S—((S)-2-(1-iminoethylamino)propyl)-D-cysteine;
S—((R/S)-2-(1-iminoethylamino)propyl)-D-cysteine;
S—((R/S)-2-(1-iminoethylamino)butyl)-L-cysteine;
S—((R/S)-2-(1-iminoethylamino,2-cyclopropyl)ethyl)-L-cysteine; and
S—((R/S)-2-(1-iminoethylamino,3-hydroxy)propyl)-L-cysteine,
or a pharmaceutically acceptable salt, solvate, or physiologically functional derivative thereof.

In another preferred embodiment of the first aspect of the invention, the iNOS inhibitor is selected from the group consisting of:
a compound having Formula I

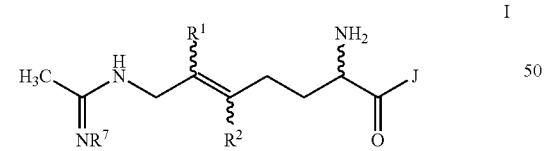

I wherein:
R1 is selected from the group consisting of H, halo and alkyl which may be optionally substituted by one or more halo;
R2 is selected from the group consisting of H, halo and alkyl which may be optionally substituted by one or more halo;
with the proviso that at least one of R1 or R2 contains a halo;
R7 is selected from the group consisting of H and hydroxy;
J is selected from the group consisting of hydroxy, alkoxy, and NR3R4 wherein;

R3 is selected from the group consisting of H, lower alkyl, lower alkylenyl and lower alkynyl;
R4 is selected from the group consisting of H, and a heterocyclic ring in which at least one member of the ring is carbon and in which 1 to about 4 heteroatoms are independently selected from oxygen, nitrogen and sulfur and said heterocyclic ring may be optionally substituted with heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, lower alkylamino, alkylthio, alkylthioalkyl, arylamino, aralkylamino, arylthio, alkylsulfinyl, alkyl sulfonyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, aryl sulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, cyanoalkyl, dicyanoalkyl, carboxamidoalkyl, dicarboxamidoalkyl, cyanocarboalkoxyalkyl, carboalkoxyalkyl, dicarboalkoxyalkyl, cyanocycloalkyl, dicyanocycloalkyl, carboxamidocycloalkyl, dicarboxamidocycloalkyl, carboalkoxycyanocycloalkyl, carboalkoxycycloalkyl, dicarboalkoxycycloalkyl, formylalkyl, acylalkyl, dialkoxyphosphonoalkyl, diaralkoxyphosphonoalkyl, phosphonoalkyl, dialkoxyphosphonoalkoxy, diaralkoxyphosphonoalkoxy, phosphonoalkoxy, dialkoxyphosphonoalkylamino, diaralkoxyphosphonoalkylamino, phosphonoalkylamino, dialkoxyphosphonoalkyl, diaralkoxyphosphonoalkyl, guanidino, amidino, and acylamino;
a compound having a structure corresponding to Formula II

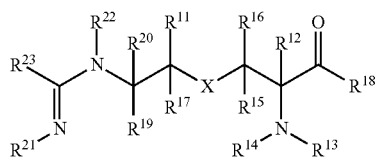

wherein X is selected from the group consisting of —S—, —S(O)—, and —S(O)₂—, R12 is selected from the group consisting of C1-C6 alkyl, C2-C6 alkenyl, C2-C6 alkynyl, C1-C5 alkoxy-C1 alkyl, and C1-C5 alkylthio-C1 alkyl wherein each of these groups is optionally substituted by one or more substituent selected from the group consisting of —OH, alkoxy, and halogen, R18 is selected from the group consisting of —OR24 and —N(R25)(R26), and R13 is selected from the group consisting of —H, —OH, —C(O)—R27, —C(O)—O—R28, and —C(O)—S—R29; or R18 is —N(R30)-, and R13 is —C(O)—, wherein R18 and R13 together with the atoms to which they are attached form a ring; or R18 is —O—, and R13 is —C(R31)(R32)-, wherein R18 and R13 together with the atoms to which they are attached form a ring, wherein if R13 is —C(R321)(R32)-, then R14 is —C(O)—O—R33; otherwise R14 is —H, R11, R15, R16, and R17 independently are selected from the group consisting of —H, halogen, C1-C6 alkyl, C2-C6 alkenyl, C2-C6 alkynyl, and C1-05 alkoxy-C1 alkyl, R19 and R20 independently are selected from the group consisting of —H, C1-C6 alkyl, C2-C6 alkenyl, C2-C6 alkynyl, and C1-C5 alkoxy-C1 alkyl, R21 is selected from the group consisting of —H, —OH, —C(O)—O—R34, and —C(O)—S—R35, and R22 is selected from the group consisting of —H, —OH, —C(O)—O—R36, and —C(O)—S—R37; or R21 is —O—, and R22 is —C(O)—, wherein R21 and R22 together with the atoms to which they are attached form a ring; or R21 is —C(O)—, and R22 is —O—, wherein R21 and R22 together with the atoms to which they are attached form a ring, R23 is C1 alkyl, R24 is selected from the group consisting of —H and C1-C6 alkyl, wherein when R24 is C1-C6 alkyl, R24 is optionally substituted by one or more moieties selected from the group consisting of cycloalkyl, heterocyclyl, aryl, and heteroaryl, R25 is selected from the group consisting of —H, alkyl, and alkoxy, and R26 is selected from the group consisting of —H, —OH, alkyl, alkoxy, —C(O)—R38, —C(O)—O—R39, and —C(O)—S—R40; wherein when R25 and R26 independently are alkyl or alkoxy, R25 and R26 independently are optionally substituted with one or more moieties selected from the group consisting of cycloalkyl, heterocyclyl, aryl, and heteroaryl; or R25 is —H; and R26 is selected from the group consisting of cycloalkyl, heterocyclyl, aryl, and heteroaryl, R27, R28, R29, R30, R31, R32, R33, R34, R35, R36, R37, R38, R39, and R40 independently are selected from the group consisting of —H and alkyl, wherein alkyl is optionally substituted by one or more moieties selected from the group consisting of cycloalkyl, heterocyclyl, aryl, and heteroaryl, wherein when any of R11, R12, R13, R14, R15, R16, R17, R18, R199, R20, R21, R22, R23, R24, R25, R26, R27, R28, R29, R30, R31, R32, R33, R34, R35 R36, R37, R38, R39, and R40 independently is a moiety selected from the group consisting of alkyl, alkenyl, alkynyl, alkoxy, alkylthio, cycloalkyl, heterocyclyl, aryl, and heteroaryl, then the moiety is optionally substituted by one or more substituent selected from the group consisting of —OH, alkoxy, and halogen;
a compound represented by Formula III

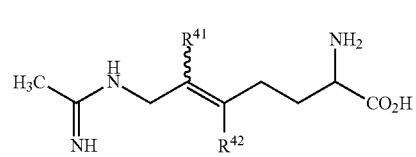

wherein:
R41 is H or methyl; and
R42 is H or methyl;
a compound of Formula IV

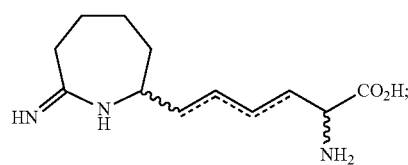

a compound of Formula V:

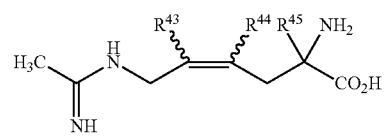

wherein:
R43 is selected from the group consisting of hydrogen, halo, C1-C5 alkyl and C1-C5 alkyl substituted by alkoxy or one or more halo;
R44 is selected from the group consisting of hydrogen, halo, C1-C5 alkyl and C1-C5 alkyl substituted by alkoxy or one or more halo;
R45 is C1-C5 alkyl or C1-C5 alkyl be substituted by alkoxy or one or more halo;
a compound of Formula VI:

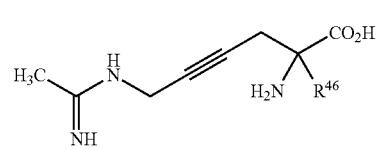

wherein:
R46 is C1-C5 alkyl, said C1-C5 alkyl optionally substituted by halo or alkoxy, said alkoxy optionally substituted by one or more halo;

a compound of Formula VII

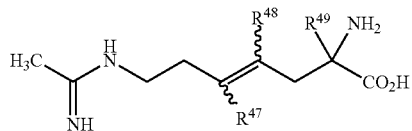

wherein:
R47 is selected from the group consisting of hydrogen, halo, C1-C5 alkyl and C1-C5 alkyl substituted by alkoxy or one or more halo;
R48 is selected from the group consisting of hydrogen, halo, C1-C5 alkyl and C1-C5 alkyl substituted by alkoxy or one or more halo;
R49 is C1-C5 alkyl or C1-C5 alkyl be substituted by alkoxy or one or more halo;

a compound of Formula VIII

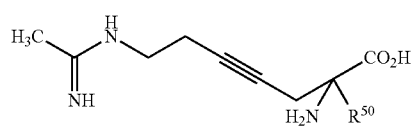

wherein:
R50 is C1-C5 alkyl, said C1-C5 alkyl optionally substituted by halo or alkoxy, said alkoxy optionally substituted by one or more halo;

a compound of Formula IX

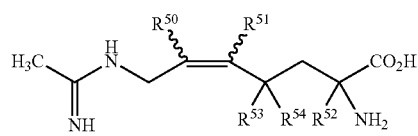

wherein:
R50 is selected from the group consisting of hydrogen, halo, and C1-C5 alkyl, said C1-C5 alkyl optionally substituted by halo or alkoxy, said alkoxy optionally substituted by one or more halo;
R51 is selected from the group consisting of hydrogen, halo, and C1-C5 alkyl, said C1-C5 alkyl optionally substituted by halo or alkoxy, said alkoxy optionally substituted by one or more halo;
R52 is C1-C5 alkyl, said C1-C5 alkyl optionally substituted by halo or alkoxy, said alkoxy optionally substituted by one or more halo;
R53 is selected from the group consisting of hydrogen, halo, and C1-C5 alkyl, said C1-C5 alkyl optionally substituted by halo or alkoxy, said alkoxy optionally substituted by one or more halo; and
R54 is selected from the group consisting of halo and C1-C5 alkyl, said C1-C5 alkyl optionally substituted by halo or alkoxy, said alkoxy optionally substituted by one or more halo;

a compound of Formula X

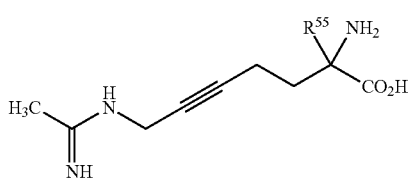

wherein:
R55 is C1-C5 alkyl, said C1-C5 alkyl optionally substituted by halo or alkoxy, said alkoxy optionally substituted by one or more halo.

a compound having the Formula XI

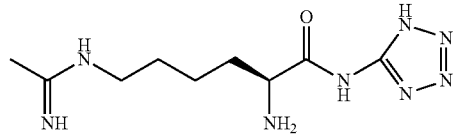 [SMILES: CC(=N)NCCCC[C@H](N)C(=O)Nc1nnn[nH]1]

2S-amino-6-[(1-iminoethyl)amino]-N-(1H-tetrazol-5-yl) hexanamide, hydrate, dihydrochloride XI A compound of Formula XII:

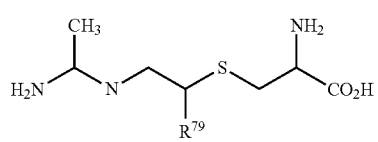

wherein R79 is selected from C1-4 alkyl, C3-4 cycloalkyl, C1-4 hydroxyalkyl, and C1-4 haloalkyl;

a compound of Formula XIII, Formula XIV or Formula XV:

Formula XIII

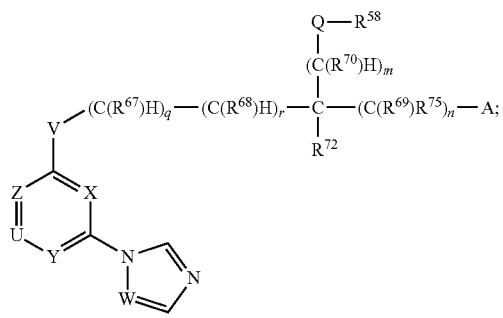

Formula XIV

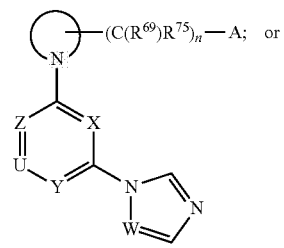

-continued

Formula XV

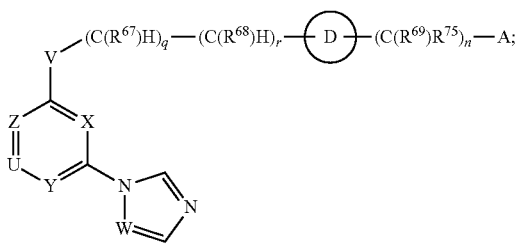

wherein:
- A is —R56, —OR56, C(O)N(R56)R57, P(O)[N(R56)R57]2, —N(R56)C(O)R57, —N(R76)C(O)OR56, —N(R56)R76, —N(R71)C(O)N(R56)R71, —S(O)tR56, —SO2NHC(O)R56, —NHSO2R77, —SO2NH(R56)H, —C(O)NHSO2R77, and —CH=NOR56;
- each X, Y and Z are independently N or C(R19);
- each U is N or C(R60), provided that U is N only when X is N and Z and Y are CR74;
- V is N(R59), S, O or C(R59)H;
- Each W is N or CH;
- Q is chosen from the group consisting of a direct bond, —C(O)—, —O—, —C(=N—R56)-, S(O)t, and —N(R61)-;
- m is zero or an integer from 1 to 4;
- n is zero or an integer from 1 to 3;
- q is zero or one;
- r is zero or one, provided that when Q and V are heteroatoms, m, q, and r cannot all be zero;
- when A is —OR56, N(R56)C(O)R57, —N(R71)C(O)OR57, —N(R56)R76, N(R71)C(O)N(R56)R71, —S(O)tR56 (where t is zero), or —NHSO2R77, n, q, and r cannot all be zero; and when Q is a heteroatom and A is —OR56, N(R56)C(O)R57, —N(R71)C(O)OR57, N(R56)R76, N(R71)C(O)N(R56)R71, —S(O)tR56 (when t is zero), or —NHSO2R77, m and n cannot both be zero;
- t is zero, one or two;

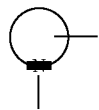

is an optionally substituted N-heterocyclyl;

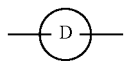

is an optionally substituted carbocyclyl or optionally substituted N-heterocyclyl;
each R56 and R57 are independently chosen from the group consisting of hydrogen, optionally substituted C1-C20 alkyl, optionally substituted cycloalkyl, —[C0-C8 alkyl]-R64, —[C2-C8 alkenyl]-R64, —[C2-C8 alkynyl]-R64, —[C2-C8 alkyl]-R65 (optionally substituted by hydroxy), —[C1-C8]—R66 (optionally substituted by hydroxy), optionally substituted heterocyclyl;
or R56 and R57 together with the nitrogen atom to which they are attached is an optionally substituted N-heterocyclyl;

R58 is chosen from the group consisting of hydrogen, alkyl, cycloalkyl, optionally substituted aryl, haloalkyl, —[C1-C8 alkyl]-C(O)N(R56)R57, —[C1-C8 alkyl]-N(R56)R57, —[C1-C8 alkyl]-R63, —[C2-C8 alk2yl]-R65, —[C1-C8 alkyl]-R66, and heterocyclyl (optionally substituted by one or more substitutents selected from the group consisting of halo, alkyl, alkoxy and imidazolyl);
or when Q is —N(R58)- or a direct bond to R58, R58 may additionally be aminocarbonyl, alkoxycarbonyl, alkyl sulfonyl, monoalkylaminocarbonyl, dialkylaminocarbonyl and —C(=NR73)-NH2;
or -Q-R58 taken together represents —C(O)OH, —C(O)N(R56)R57 or

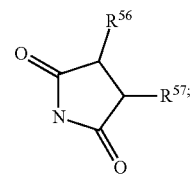

R59 is chosen from the group consisting of hydrogen, alkyl, aryl, aralkyl and cycloalkyl;
Provided that when A is —R56 or —OR56, R59 cannot be hydrogen, and when V is CH, R59 may additionally be hydroxy;
R60 is chosen from the group consisting of hydrogen, alkyl, aryl, aralkyl, haloalkyl, optionally substituted aralkyl, optionally substituted aryl, —OR71, —S(O)t-R71, N(R71)R76, N(R71)C(O)N(R56)R71, N(R71)C(O)OR71, N(R71)C(O) R71, —[C0-C8 alkyl]-C(H)[C(O)R71]2 and —[C0-C8 alkyl]-C(O)N(R56)R71;
R61 is chosen from the group consisting of hydrogen, alkyl, cycloalkyl, —[C1-C8 alkyl]-R63, [C2-C8]alkyl]-R65, —[C1-C8 alkyl]-R66, acyl, —C(O)R63, —C(O)— —[C1-C8 alkyl]-R63, alkoxycarbonyl, optionally substituted arylcarbonyl, optionally substituted aralkoxycarbonyl, alkylsulfonyl, optionally substituted aryl, optionally substituted heterocyclyl, alkoxycarbonylalkyl, carboxyalkyl, optionally substituted aryl sulfonyl, aminocarbonyl, monoalkylaminocarbonyl, dialkylaminocarbonyl, optionally substituted arylaminocarbonyl, aminosulfonyl, monoalkylaminosulfonyl dialkylaminosulfonyl, arylaminosulfonyl, aryl sulfonylaminocarbonyl, optionally substituted N-heterocyclyl, —C(=NH)—N(CN)R56, —C(O)R78-N(R56)R57, —C(O)—N(R56)R78-C(OOR56;
each R63 and R64 are independently chosen from the group consisting of haloalkyl, cycloalkyl, (optionally substituted with halo, cyano, alkyl or alkoxy), carbocyclyl (optionally substituted with one or more substituents selected from the group consisting of halo, alkyl and alkoxy) and heterocyclyl (optionally substituted with alkyl, aralkyl or alkoxy);
each R65 is independently chosen from the group consisting of halo, alkoxy, optionally substituted aryloxy, optionally substituted aralkoxy, optionally substituted —S(O)t-R77, acylamino, amino, monoalkylamino, dialkylamino, (triphenylmethyl)amino, hydroxy, mercapto, alkylsulfonamido;
each R66 is independently chosen from the group consisting of cyano, di(alkoxy)alkyl, carboxy, alkoxycarbonyl, aminocarbonyl, monoalkylaminocarbonyl and dialkylaminocarbonyl;
each R67, R68, R69, R70, R72, and R75 are independently hydrogen or alkyl;

each R71 is independently hydrogen, alkyl, optionally substituted aryl, optionally substituted aralkyl or cycloalkyl;

R73 is hydrogen, NO2, or toluenesulfonyl;

each R74 is independently hydrogen, alkyl (optionally substituted with hydroxy), cyclopropyl, halo or haloalkyl;

each R76 is independently hydrogen, alkyl, cycloalkyl, optionally substituted aryl, optionally substituted aralkyl, —C(O)R77 or —SO2R77;

or R76 taken together with R56 and the nitrogen to which they are attached is an optionally substituted N-heterocyclyl;

or R76 taken together with R71 and the nitrogen to which they are attached is an optionally substituted N-heterocyclyl;

each R77 is independently alkyl, cycloalkyl, optionally substituted aryl or optionally substituted aralkyl; and R78 is an amino acid residue; and

PPA250

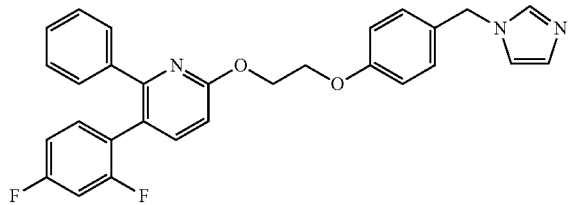

PPA250 or a pharmaceutically acceptable salt or prodrug of any of said inducible nitric oxide synthase inhibitors.

In still another preferred embodiment of the first aspect of the invention, the iNOS inhibitor is a coumarin and is selected from the group consisting of a compound of formula (XVI):

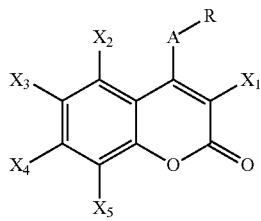

(I)

wherein:

A is O,

R is selected from the group consisting of $(CH_2)_n NR_1R_2$, wherein $R_1$ and $R_2$ are the same or different and are selected from the group consisting of hydrogen, $C(=NH)NH_2$ and $C_1$-$C_6$ alkyl, n is an integer of from 2-5;

$X_1$ is hydrogen $X_2$ is hydrogen;

$X_3$ is halogen, $X_4$ is hydrogen; and $X_5$ is hydrogen with the proviso that when n is 2, $R_1$ and $R_2$ are not both hydrogen or both ethyl and $X_3$ chlorine, and the pharmaceutically acceptable salts and optical isomers thereof.

In a preferred embodiment of the first aspect of the invention, refers to the compound of formula XVI wherein:

A is O;

R is $(CH_2)_n NR_1R_2$, and $X_3$ is halogen.

Preferably, $R_1R_2$ are selected from the group consisting of hydrogen, $C_{1-6}$alkyl, and $C(=NH)NH_2$.

More preferably, $X_3$ is selected from the group consisting of bromine and chlorine.

More preferably, the compound is selected from the group consisting of:

6-Chloro-4-(3-aminopropoxy)-1-benzopyran-2-one,
6-Chloro-4-(3-methylamino-propoxy)-1-benzopyran-2-one,
4-(2-Amino-ethoxy)-6-chloro-1-benzopyran-2-one,
4-(3-Amino-propoxy)-6-bromo-1-benzopyran-2-one,
4-(3-Amino-propoxy)-6-fluoro-1-benzopyran-2-one,
6-Chloro-4-(3-dimethylamino-propoxy)-1-benzopyran-2-one,
N-[3-(6-Chloro-2-oxo-2H-1-benzopyran-4-yloxy)-propyl]-guanidine,
N-[3-(6-Chloro-2-oxo-2H-1-benzopyran-4-yloxy)-propyl]-acetamide,
4-(5-Amino-pentyloxy)-6-chloro-1-benzopyran-2-one.

or a pharmaceutically acceptable salt, solvate, or physiologically functional derivative thereof.

The method according to the first aspect of the invention or to any of its preferred embodiments, wherein the subject has or suffers from bicuspid aortic valve; a syndromic thoracic aortic aneurysm (TAA) such as Marfan Syndrome, vascular Ehlers Danlos, Loeys Dietz Syndrome (Types 1 and 2), and Familial thoracic aortic aneurysm and dissection (familial TAAD); a non-syndromic TAAs or any other disease associated with an aorthopathy triggered by Adamts1 deficiency.

The method according to the first aspect of the invention or to any of its preferred embodiments, wherein administering an iNOS selective inhibitor or pharmaceutically acceptable salt or prodrug thereof comprises administering to the subject orally, by inhalation, enterally or parenterally in at least one dose per day.

A second aspect of the invention refers to a composition for use in the treatment, prevention or inhibition of TAA, or a bicuspid aortic valve; or a syndromic thoracic aortic aneurysm (TAA) such as Marfan Syndrome, vascular Ehlers Danlos, Loeys Dietz Syndrome (Types 1 and 2), and Familial thoracic aortic aneurysm and dissection (familial TAAD); or a non-syndromic TAAs; or any other disease associated with an aorthopathy triggered by Adamts1 deficiency, in a subject in need of such treatment, prevention or inhibition comprising an amount of an iNOS selective inhibitor or pharmaceutically acceptable salt or prodrug thereof. Preferably, such iNOS selective inhibitor is as defined in the first aspect of the invention or as defined in any of its preferred embodiments. In a preferred embodiment of the second aspect of the invention, said composition is administered to the subject orally, by inhalation, enterally or parenterally in at least one dose per day.

In another preferred embodiment of the second aspect of the invention, the subject has or suffers from Marfan syndrome.

On the other hand, and in addition to the above said method of treatment, the authors of the present invention have also found that Adamts1 deficiency in mice or humans has a clear correlation with the thoracic aortic phenotype, particularly the syndromic thoracic aortic aneurysm (TAA), more particularly the syndromic thoracic aortic aneurysm (TAA) of subjects or patients having or suffering from MFS (see examples).

Thus a third aspect of the invention refers to an in vitro method for screening for subjects at risk of developing TAA comprising: (a) measuring the expression pattern or level of at least A Disintegrin And Metalloproteinase with Thrombospondin Motifs 1 (ADAMTS1) obtained from an isolated biological sample of the subjects to be screened; and (b) comparing said expression pattern or level of at least ADAMTS1 of the subjects to be screened with an already established expression pattern or level, wherein reduced expression of at least ADAMTS1 is indicative of thoracic aortic aneurysm (TAA).

It is noted that ADAMTS1 substrates can also be used for the purpose of the third aspect of the invention. In this sense, alternatively or in addition to the method described in the third aspect of the invention, a fourth aspect of the invention thus refers to an in vitro method for screening subjects at risk of developing TAA comprising:

(a) measuring the expression pattern or level in an isolated biological sample of the subjects to be screened of at least ADAMTS1 and/or at least the inducible form of the nitric oxide synthase (iNOS) and/or at least the expression pattern of any of the following ADAMTS1 substrates: Aggrecan, versican, tissue factor pathway inhibitor-2 (TFPI-2), semaphorin 3C, nidogen-1, nidogen-2, desmocollin-3, dystroglycan, mac-2, Collagen type I, amphiregulin, TGF-α, heparin-binding EGF, Syndecan 4, versican neoepitopes or aggrecan neoepitopes; and b) comparing said expression pattern or level of at least ADAMTS1 and/or at least the inducible form of the nitric oxide synthase (iNOS) and/or at least the expression pattern of any of the following ADAMTS1 substrates: Aggrecan, versican, tissue factor pathway inhibitor-2 (TFPI-2), semaphorin 3C, nidogen-1, nidogen-2, desmocollin-3, dystroglycan, mac-2, Collagen type I, amphiregulin, TGF-α, heparin-binding EGF, Syndecan 4, versican neoepitopes or aggrecan neoepitopes, of the subjects to be screened with an already established expression pattern or level, wherein reduced expression of at least ADAMTS1, Syndecan 4, versican neoepitopes and/or aggrecan neoepitopes and overexpression of at least iNOS, Aggrecan, versican, tissue factor pathway inhibitor-2 (TFPI-2), semaphorin 3C, nidogen-1, nidogen-2, desmocollin-3, dystroglycan, mac-2, Collagen type I, amphiregulin, TGF-α and/or heparin-binding EGF, is indicative of thoracic aortic aneurysm (TAA). Preferably, the method of the third or fourth aspects of the invention screens for subjects at risk of developing diseases causing TAA such as bicuspid aortic valve; or a syndromic thoracic aortic aneurysm (TAA) such as Marfan Syndrome, vascular Ehlers Danlos, Loeys Dietz Syndrome (Types 1 and 2), and Familial thoracic aortic aneurysm and dissection (familial TAAD); or a non-syndromic TAA; or any other disease associated with the aorthopathy triggered by Adamts1 deficiency (from hereinafter TAA and any other disease included in the list of diseases referred to in this paragraph, will be herein referred to as "TAA related diseases" or "TAA related disease").

A fifth aspect of the invention refers to an in vitro method for the diagnosis of a subject suspected of suffering from a TAA related disease, comprising the steps a) and b) of any of the third or fourth aspects of the invention, and optionally (c) confirming the presence of the disease by means of a clinical examination.

A sixth aspect of the invention refers to a method for obtaining useful data for the in vitro diagnosis of a TAA related disease, comprising the steps a) and b) of any of the third or fourth aspects of the invention.

A seventh aspect of the invention refers to an in vitro method for classifying subjects as healthy subjects or as subjects suffering from a TAA related disease, comprising the steps a) and b) of any of the third or fourth aspects of the invention.

An eight aspect of the invention refers to an in vitro method for monitoring the response to a therapy or for monitoring the progression of a TAA related disease, in a subject suffering from a TAA related disease comprising the steps a) and b) of any of the third or fourth aspects of the invention.

A ninth of the invention refers to a method for treating subjects suffering from a TAA related disease, comprising the steps a) and b) of any of the third or fourth aspects of the invention, and (c) treating the patient diagnosed with said disease. Preferably said treatment is with iNOS inhibitors, more preferably with an iNOS inhibitor as defined in the first aspect of the invention or as defined in any of its preferred embodiments. Alternatively, the invention refers to a composition comprising an iNOS inhibitor for use in the treatment of a TAA related disease in a patient diagnosed with said disease by a method comprising the steps a) and) of any of the third or fourth aspects of the invention. Preferably said treatment is with selective iNOS inhibitors, more preferably with an iNOS inhibitor as defined in the first aspect of the invention or as defined in any of its preferred embodiments.

In a preferred embodiment, the methods or compositions of any of aspects third to ninth, the TAA related disease is selected from the group consisting of Marfan Syndrome, vascular Ehlers Danlos, Loeys Dietz Syndrome (Types 1 and 2), aorthopathy triggered by Adamts1 deficiency and Familial thoracic aortic aneurysm and dissection (familial TAAD); preferably, Marfan syndrome.

In another preferred embodiment, the methods or compositions of any of the precedent aspects, the biological sample is selected from the group consisting of a biopsy sample (such as an aortic biopsy) or of a minimally-invasive biological sample of the subjects to be screened such as a plasma sample, blood sample, Cerebrospinal fluid (CSF) sample or a serum sample.

A tenth aspect of the invention refers to the in vitro use of a kit comprising biomarker detecting reagents for determining a differential expression level (of proteins, peptides or nucleotides) in an isolated biological sample of at least ADAMTS1 and/or at least the inducible form of the nitric oxide synthase (iNOS) and/or at least the expression pattern of any of the following ADAMTS1 substrates: Aggrecan, versican, tissue factor pathway inhibitor-2 (TFPI-2), semaphorin 3C, nidogen-1, nidogen-2, desmocollin-3, dystroglycan, mac-2, Collagen type I, amphiregulin, TGF-α, heparin-binding EGF, Syndecan 4, versican neoepitopes and aggrecan neoepitopes, for diagnosing in vitro the risk that a subject suffers or has a TAA related disease. More preferably said kit is use for identifying a risk of suffering from a TAA related disease such as Familial thoracic aortic aneurysm and dissection (familial TAAD) or Marfan syndrome (MFS).

Preferably, the tenth aspect of the invention refers to the in vitro use of a kit comprising biomarker detecting reagents for determining a differential expression level in an isolated biological sample of at least ADAMTS1, wherein a reduced expression of at least ADAMTS1 is indicative of a TAA related disease, for diagnosing in vitro the risk that a subject suffers or has a TAA related disease.

In another preferred embodiment of the tenth aspect of the invention, the kit comprises at least the following nucleotides for the detection of at least Adamts1 and optionally the nitric oxide synthase 2:

Adamts1
(ACACTGGCGGTTGGCATCGT (SEQ ID NO: 1),

GCCAGCCCTGGTCACCTTGC (SEQ ID NO: 2)},

Nos2
(CAGCTGGGCTGTACAAACCTT (SEQ ID NO: 3),

CATTGGAAGTGAAGCGTTTCG (SEQ ID NO: 4)).

Preferably, the above kit is especially suitable and comprises additional reagents for performing qPCR reactions. Preferably, these reactions are performed in triplicate with SYBR-master mix (Applied Biosystems) according to the manufacturer's guidelines.

In a still further preferred embodiment of the tenth aspect of the invention, the kit comprises the reagents suitable, such as antibodies or fragments thereof, for detecting any of the peptides or proteins as defined in the kits of the tenth aspect of the invention.

In a still further preferred embodiment of the tenth aspect of the invention, the isolated biological sample is selected from the group consisting of a biopsy sample (such as an aortic biopsy) or of a minimally-invasive biological sample of the subjects to be screened such as a plasma sample, blood sample, Cerebrospinal fluid (CSF) sample or a serum sample.

It is noted that the present invention further refers to computer implemented processes of any of the methods described in any of aspects third to ninth as well as to the devices used for the implementation of such processes.

Lastly, in virtue of the fact that the present invention identifies the NO pathway, in particular iNOS, as an essential mediator of aortic disease in mouse models and suggests such pathway as a possible target for intervention in thoracic aortopathies, the authors of the present invention have configured a new screening method for identifying compounds useful for the treatment, prevention or inhibition of a thoracic aortic aneurysm (TAA). Said screening method for identifying compounds useful for the treatment, prevention or inhibition of a thoracic aortic aneurysm (TAA), comprising the following steps:

1. Identifying a compound or a group of compounds capable of acting as NOS inhibitors, in particular iNOS inhibitors. For this purpose, although not limiting the invention, usually a reliable method to measure nitric oxide metabolites is needed. NO can be determined by direct in vivo use of electrochemical probes (though these are subject to many limitations), electron paramagnetic resonance spectroscopy and fluorescence imaging. Nitrite can be determined by use of the Griess reaction and its derivatives, chromatography and chemiluminescence. S-nitrosothiols can also be quantified by chemiluminescence; determination of their location on proteins requires tagging the sites of S-nitrosation, such as by the Biotin switch technique or a derivative thereof. Other ways, non limiting the present invention, of identifying a compound or a group of compounds capable of acting as NOS inhibitors is by determining whether nitric oxide stimulates soluble guanylyl cyclase to increase cellular cGMP levels. In this sense, kinase activity can be assayed with 35 ng recombinant PKG1 protein in reactions containing 8 µg kemptide. Reactions are performed for 5 min at 30° C. in 40 mM HEPES (pH 7.0), 8 µg kemptide (Sigma-Aldrich), 10 mM MgCl2, 60 µM ATP, 0.6 µCi 32P-g-ATP, and variable amounts of cGMP (0-3000 nM). Reactions are stopped by spotting on P81 phosphocellulose paper, and activity is measured by liquid scintillation counting. Lastly, computational design of iNOS inhibitors also forms part of the present invention;

2. Determining the usefulness of the selected compounds identified in 1) above for the treatment, prevention or inhibition of a thoracic aortic aneurysm (TAA), by the corresponding in vivo or in vitro methods. For example, by determining the levels of phosphorylated RLC (pRLC) by immunoblotting of protein extracts derived from normal fibroblasts exposed to variable amounts of the selected inhibitors. These levels are normalized to total RLC levels. Those compounds that increase the pRLC/RLC ratio are selected for validation in mouse models, including Adamts1$^{+/-}$ mice and the Fbn1$^{C1039G/+}$ mouse model of Marfan syndrome. Those compounds that decrease the diameter of the ascending thoracic aorta without increasing the blood pressure are candidates for clinical trials.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of groups, those skilled in the art will recognize that the invention is also thereby described in terms of any individual member or subgroup of members of the group.

EXAMPLES

Example 1. Experimental Procedures

Animal Procedures

Animal procedures were approved by the CNIC Ethics Committee and conformed to European Union guidelines for the care and experimental use of animals. Adamts1+/− mice were obtained from the European Mouse Mutant Archive [(EM:02291) B6; 129P2-Adamts1<tm1Dgen>/H] and carried a LacZ-Neo cassette to replace a genomic sequence (c7784) between exon1 and 2 in the Adamts1 target allele. Fbn1C1039G/+ mice (Judge et al., 2004), harboring a mutation in the Fbn1 gene, and Nos2−/− mice (Laubach et al., 1995) were obtained from Jackson Laboratories (JAX mice stock #012885 and 007072, respectively). These 3 strains had been previously backcrossed to C57BL/6 for more than nine generations. All mice were genotyped by PCR of tail samples using the following primers: Adamts1 mice (5'-GCCATCGGGGTCAGCTTTTCAAATG-3'(SEQ ID NO: 5), 5'-GGGCCAGCTCATTCCTCCCACTCAT (SEQ ID NO: 6)/GGTTGTAGTTTCGCGCTGAGTTTTG-3' (SEQ ID NO: 7)); Nos2−/− mice (5'ACATGCAGAATGAGTACCGG 3' (SEQ ID NO: 8); 5' TCAACATCTCCTGGTGGAAC 3'(SEQ ID NO: 9), 5' AATATGCGAAGTGGACCTCG 3') (SEQ ID NO: 10); Fbn1C1039G/+ mice (5'CTC ATC ATT TTT GGC CAG TTG 3' (SEQ ID NO: 11), 5'GCA CTT GAT GCA CAT TCA CA 3' (SEQ ID NO: 12)). Wild-type littermates were used as controls unless otherwise specified. Mice were treated with Ang-II (Sigma-Aldrich) at 1 µg/kg/min or losartan (Sigma Aldrich) at 10 mg/kg/day using subcutaneous osmotic minipumps (Alzet Corp). The monoclonal pan-antibody against TGFβ1, 2, 3 clone 1D11 (BioXcell) was injected intraperitoneally 3 times per week at 10 mg/kg. Nω-Nitro-L-arginine methyl ester hydrochloride (L-NAME, Sigma-Aldrich), was given to mice over 21 d (and an additional 3 d before LVi inoculation in infected mice) at 0.5 mg/ml in drinking water.

Blood Pressure Measurements and In Vivo Imaging

Arterial blood pressure (BP) was measured in mouse tails using the automated BP-2000 Blood Pressure Analysis System (Visitech Systems, Apex, NC, USA). In brief, mice were trained for BP measurements every day for one week. After training, BP was measured one day before treatment or before lentiviral infection to determine the baseline BP values in each mouse cohort. Measurements were repeated several times during experiments. BP measurements were recorded in mice located in a tail-cuff restrainer, over a warmed surface (37° C.). Fifteen consecutive systolic and diastolic BP measurements were made, and the last ten readings per mouse were recorded and averaged.

For in vivo ultrasound images, the aortic diameter was monitored in isofluorane-anesthetized mice (2% isofluorane) by high-frequency ultrasound with a VEVO 2100 echography device (VisualSonics, Toronto, Canada). Maximal internal diameters of aortic images were measured using VEVO 2100 software, version 1.5.0. All recordings were made by a cardiologist and a technician who were blinded to animal genotype and treatment. Measurements were taken before lentivirus administration or the corresponding treatments to determine the baseline diameters, and measurements were repeated several times during the experiment.

Whole body skeleton was imaged in anesthetized mice (1.5-2% isofluorane) using an X-Ray CT system integrated in a nano PET-CT scanner (Mediso Medical Imaging Systems, Budapest). Images were acquired at 55 Kv, 500 mA/sec, 360 frames per Rx rotation, and pitch=1. Skeletal 3D reconstruction was performed with Medis software (Medis, The Netherlands).

Cell Procedures

Mouse vascular smooth muscle cells (VSMCs) were isolated and grown as described (Esteban et al., 2011). All experiments were performed during passages 3-7. VSMCs were infected at a multiplicity of infection (MOI)=3 over 5 h. The medium was then replaced with fresh DMEM supplemented with 10% FBS, and cells were cultured for 3 more days, serum-starved for 48 h and then stimulated with Ang-II for 6 h for protein assays or 4 h for mRNA expression analysis.

siRNA-Encoding Lentivirus Production and Infection.

Lentiviruses expressing GFP and siRNA targeting mouse Adamts1 mRNA were purchased from ABM-GOOD. siRNA sequences were as follows: #siRNA27 (GGAAAGAATCCGCAGCTTTAGTCCACTCA) (SEQ ID NO: 13); #siRNA57 (ACCGCCAGTGTCAGTTTACATTCGGAGAG) (SEQ ID NO: 14); #siRNA69 (CTTCCGAATGTGCAAAGGAAGTGAAGCCA) (SEQ ID NO: 15). siCtl (GGGTGAACTCACGTCAGAA) (SEQ ID NO: 16) was used as a control. Pseudo-typed lentiviral production was obtained by transient calcium phosphate transfection of HEK-293T cells. Supernatant containing the lentiviral particles was collected 48 h after removal of the calcium phosphate precipitate, and ultracentrifuged for 2 h at 26,000 rpm (Ultraclear Tubes, SW28 rotor and Optima L-100 XP Ultracentrifuge; Beckman). Viruses were suspended in cold sterile PBS solution and titrated by transduction of Jurkat cells for 48 h. Transduction efficiency (GFP-expressing cells) and cell death (propidium iodide staining) were quantified by flow cytometry.

For in vivo transduction experiments, animals were anesthetized (ketamine/xilacine) and a small incision was made to expose the right jugular vein (Esteban et al., 2011). Virus solution (100μ, 109 particles/ml in PBS) was inoculated directly into the right jugular vein 3 weeks before Ang-II mini-pump implantation or one day before monitoring of aortic dilation. Transduction efficiency was analyzed in aortic samples by immunohistochemistry for GFP and Adamts1.

Aortic Histology

After $CO_2$-induced euthanasia, mouse aortas were perfused with saline, isolated, and fixed in 4% paraformaldehyde overnight at 4° C. 5-μm paraffin cross sections from fixed aortas were stained with Masson's trichrome (Masson), alcian blue or Verhoeff elastic—van Gieson (EVG) or were used for immunohistochemistry or immunofluorescence. Deparaffinized sections were rehydrated, boiled to retrieve antigens (10 mM citrate buffer, pH6) and blocked for 45 min with 10% goat serum plus 2% BSA in PBS. Samples were incubated with the following antibodies for immunohistochemistry or immunofluorescence: anti-Adamts1 (1/100; Santa Cruz), anti-GFP (1/100; Invitrogen), anti-pSMAD2 (1/50 Cell Signaling) anti-pSMAD2,3 (1/100 Santa Cruz), anti-TGFβ1 (1/100; Abcam ab92486), NOS2 (1/100 Santa Cruz for mice, and Millipore for human). Specificity was determined by substitution of primary antibody with unrelated IgG (Santa Cruz). For immunohistochemistry, color was developed with DAB (Vector Laboratories) and sections were counterstained with hematoxylin and mounted in DPX (Fluka). Images were acquired under a Leica DM2500 microscope with 20×, 40× or 63×HCX PL Fluotar objective lenses and Leica Application Suite V3.5.0 acquisition software. For immunofluorescence, secondary antibodies were AlexaFluor546-conjugated goat anti-rabbit and AlexaFluor647-conjugated goat anti-rabbit (BD Phramigen). Sections were mounted in Citifluor AF4 mounting medium (Aname) with DAPI. Images were acquired at 1024×1024 pixels, 8 bits, using a Leica SP5 confocal microscope with 20× or 40× oil immersion objectives.

Images of Masson's trichrome and EVG staining were analyzed for collagen content with ImageJ (http://rsbweb.nih.gov/ij/index.html) and with MetaMorph (Molecular Devices; Sunnyvale, California) for quantification of elastin breaks. For each animal, elastin breaks were counted in 3 sections and the mean number of breaks was calculated. Images were processed for presentation with Photoshop and Illustrator (Adobe).

Immunoblot Analysis

Mouse aortic samples were isolated, frozen in liquid nitrogen and then homogenized (MagNA lyzer, Roche). Protein extracts were obtained by lysis in ice-cold RIPA buffer (50 mM NaCl, 50 mM Tris HCl pH8, 1% NP40, 0.1% SDS, 0.5% sodium deoxycolate) completed with protease, phosphatase, and kinase inhibitors. For VSMCs, cells were infected and then stimulated with AngII, washed with ice-cold PBS, and lysed in RIPA buffer.

Proteins were separated under reducing conditions on SDS-polyacrylamide gels and transferred to nitrocellulose membranes. Protein detection was performed with the following primary antibodies: anti-Adamts1 (1/1000; Santa Cruz), anti-GFP (1/1000; Invitrogen), anti-pSMAD2 (1/500; Cell Signaling), Anti-alpha Tubulin (1/40,000; Sigma-Aldrich), Anti-GAPDH (1/10,000; Abcam). Bound antibodies were detected with enhanced chemiluminescence (ECL) detection reagent (Millipore).

RT and Quantitative PCR

Aortas were extracted after perfusion with 5 ml saline solution perfusion, and the adventitia layer was discarded. Frozen tissue was homogenized using a mortar and an automatic bead homogenizer (MagNA Lyzer, Roche). Total RNA was isolated with TRIZOL (Life Technologies). Total RNA (2 μg) was reverse transcribed at 37° C. for 50 min in a 20 ul reaction mix containing 200 U Moloney murine leukemia virus (MMLV) reverse transcriptase (Life Technologies), 100 ng random primers, and 40 U RNase Inhibitor (Life Technologies). Real-time quantitative RT-PCR was performed with the following PCR primers: Adamts1 (ACACTGGCGGTTGGCATCGT (SEQ ID NO: 1), GCCAGCCCTGGTCACCTTGC (SEQ ID NO: 2)), Tgfβ1 (CGCCATCTATGAGAAAACC (SEQ ID NO: 17), GTAACGCCAGGAATTGT (SEQ ID NO: 18)), Ctgf (GTGCCAGAACGCACACTG (SEQ ID NO: 19), CCCCGGTTACACTCCAAA (SEQ ID NO: 20)), Col1a1 (GCTCCTCTTAGGGGCCACT (SEQ ID NO: 21), CCACGTCTCACCATTGGGG (SEQ ID NO: 22)), Pai-1 (GCCAGATTT ATCATCAATGACTGGG (SEQ ID NO: 23), GGAGAGGTGCACATCTTTCTC AAAG (SEQ ID NO: 24)), Nos3 (GTTTGTCTGCGGCGATGTC (SEQ ID NO: 25), CATGCCGCCCTCTGTTG (SEQ ID NO: 26)), Nos2 (CAGCTGGGCTGTACAAACCTT (SEQ ID NO: 3), CATTGGAAGTGAAGCGTTTCG (SEQ ID NO: 4)). qPCR reactions were performed in triplicate with SYBR-master mix (Applied Biosystems) according to the manufacturer's guidelines. To examine probe specificity, we conducted a post-amplification melting-curve analysis. For each reaction, only one Tm peak was produced. The amount of target mRNA in samples was estimated by the 2-ΔCT relative quantification method, using GAPDH for normalization. Fold ratios were calculated relative to control animals.

Nitric Oxide Staining

NO staining was performed in unfixed fresh aortic sections from mice with DAF-FM Diacetate reagent (Molecular Probes) according to manufacturer's instructions. Samples were incubated with 10 μmol/L DAF-FM Diacetate reagent during 1 hour at RT and mounted in 10% glycerol/PBS. Images were acquired in Leica SP5 microscope.

Zymography Assays

Aortic extracts were prepared from whole aortas as described for immunoblot assays, but in the absence of DTT. Extracts (15 μg) were fractionated under nonreducing conditions on SDS-polyacrylamide gels containing 1% gelatin. Gels were washed three times in 2.5% Triton x-100 for 30 min at RT, incubated in 50 mM Tris-HCl pH 7.5, 10 mM CaCl2, and 200 mM NaCl overnight at 37° C., and stained with Coomasie Blue. The areas of gelatinolytic or MMP activity were visualized as transparent bands. Images were analyzed with Quantity One software (Bio-Rad).

Adamts1 ELISA

Serum Adamts1 was measured in 50 μl mouse serum with an ELISA kit (BioNova).

Human Samples

The study was approved by the Ethics and Clinical Research Committee of Cantabria. Ascending aorta was anonymously obtained from multi-organ transplant donors after written informed consent from their families. During preparation of the heart for transplantation, excess ascending aortic tissue was harvested for the study. Clinical data from patients were retrieved while maintaining anonymity. The tissue was immediately fixed, kept at room temperature for 48 hours, and included in paraffin.

Statistical Analysis

Graphpad Prism software 6.01 was used for the analysis. The aortic diameter data were presented as box and whiskers plots, with 75th and 25th percentiles; bars represent maximal and minimal data. Differences were analyzed by one-way or two-way analysis of variance (ANOVA) and Bonferroni's post-hoc test or Newman's post-hoc test (experiments with ≥3 groups). For survival curves, differences were analyzed with the Log-rank (Mantel-Cox) test. Statistical significance was assigned at * $p<0.05$,  $p<0.01$, * $p<0.001$, and **** $p<0.0001$.

Example 2. Constitutive Adamts1 Deficiency Induces a Syndromic Form of TAA

Figure 1:
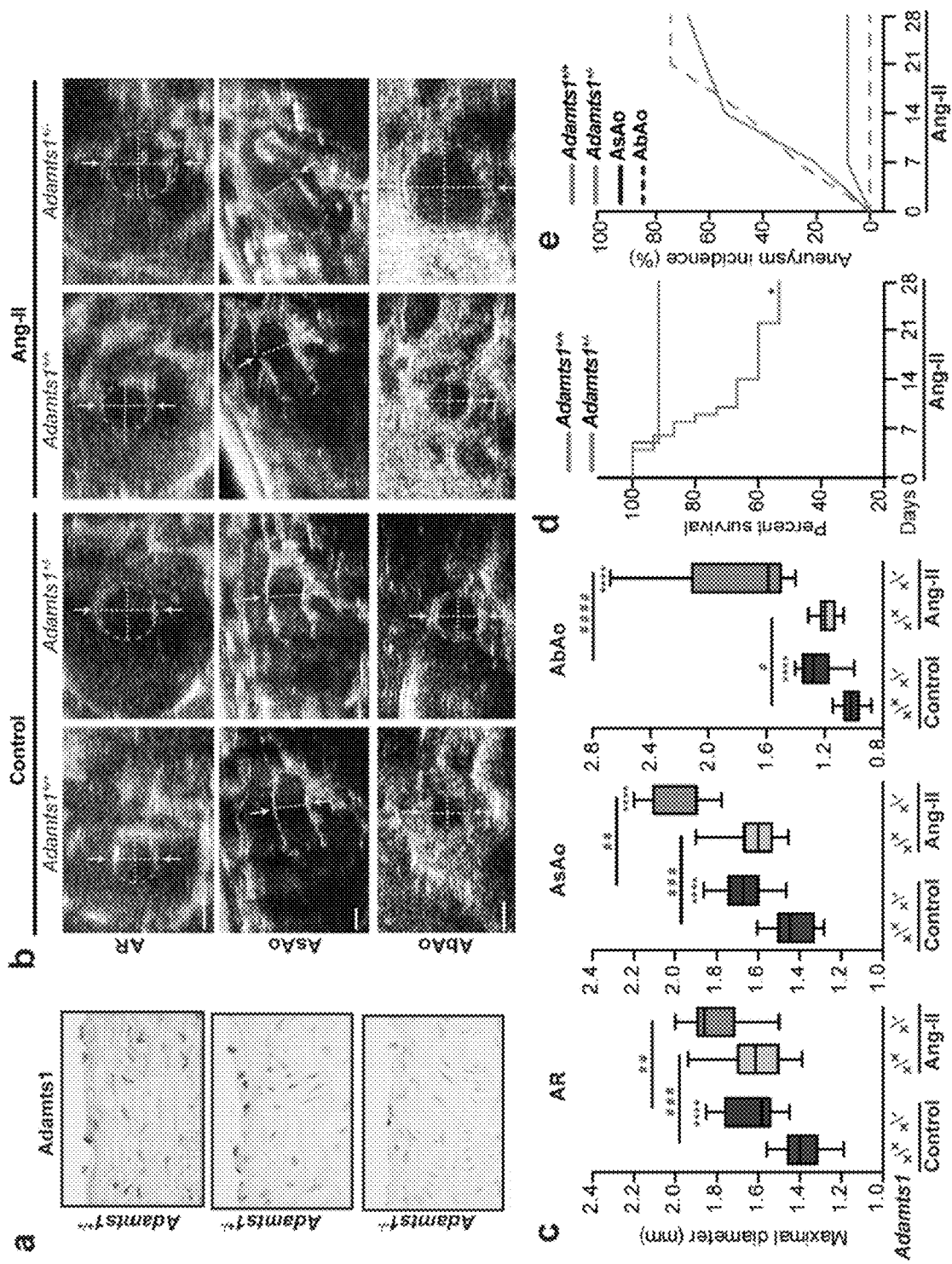
FIG. 1. Induction of syndromic TAA by Adamts1 deficiency. (a) Representative images of Adamts1 immunostaining on aortic sections from the indicated mice (n=3). Scale bar, 20 µm. (b) Representative ultrasound images of AR, AsAo and AbAo control-treated or treated with Ang-II for 28 days. Red lines mark the lumen boundary and yellow the lumen diameter. Scale bars, 1 mm. (c) Maximal diameter (mean±SEM) of the indicated aortic sections from control-treated Adamts1+/+(n=13) and Adamts1+/−(n=15) mice and from AngII treated Adamts1+/+(n=11) and Adamts1+/− (n=14) mice. One-way ANOVA, ****p<0.0001 Adamts1+/+ vs Adamts1+/−; ####p<0.0001, ###p>0.001, ##p<0.01, #p<0.05 Control vs Ang-II. (d) Survival curve of the Ang-II-treated cohort of Adamts1+/+ and Adamts1+/− mice shown in (c). Log-rank (Mantel-Cox) test, *p<0.05. (e) Aneurysm incidence in the same cohort. (f) End-of treatment systolic and diastolic BP. One-way ANOVA, ****p<0.001 Adamts1+/+vs Adamts1+/−; ####p<0.0001 Control vs Ang-II. (g) Representative H&E staining of sections from 10 Adamts1+/+ and 7 Adamts1+/− insufflated lungs. *indicates progressive distal airspace enlargement. Scale bars, 500 µm (left) and 50 µm (right). (h) Representative skeletal PET CT images of 16-20-week-old Adamts1+/+ (n=10) and Adamts1+/− mice (n=9). Red dotted lines, 1.67 cm. Kyphosis incidence is indicated. (i) Anteroposterior and transverse thoracic diameters (mean±SEM) and length quantification of (j) cranium and (k) humerus, femur and tibia (mean±SEM) of 20 Adamts1+/+ and 17 Adamts1+/− mice. Student's t-test, ns, non-significant; p<0.01 and *p<0.001.
Figure 1:
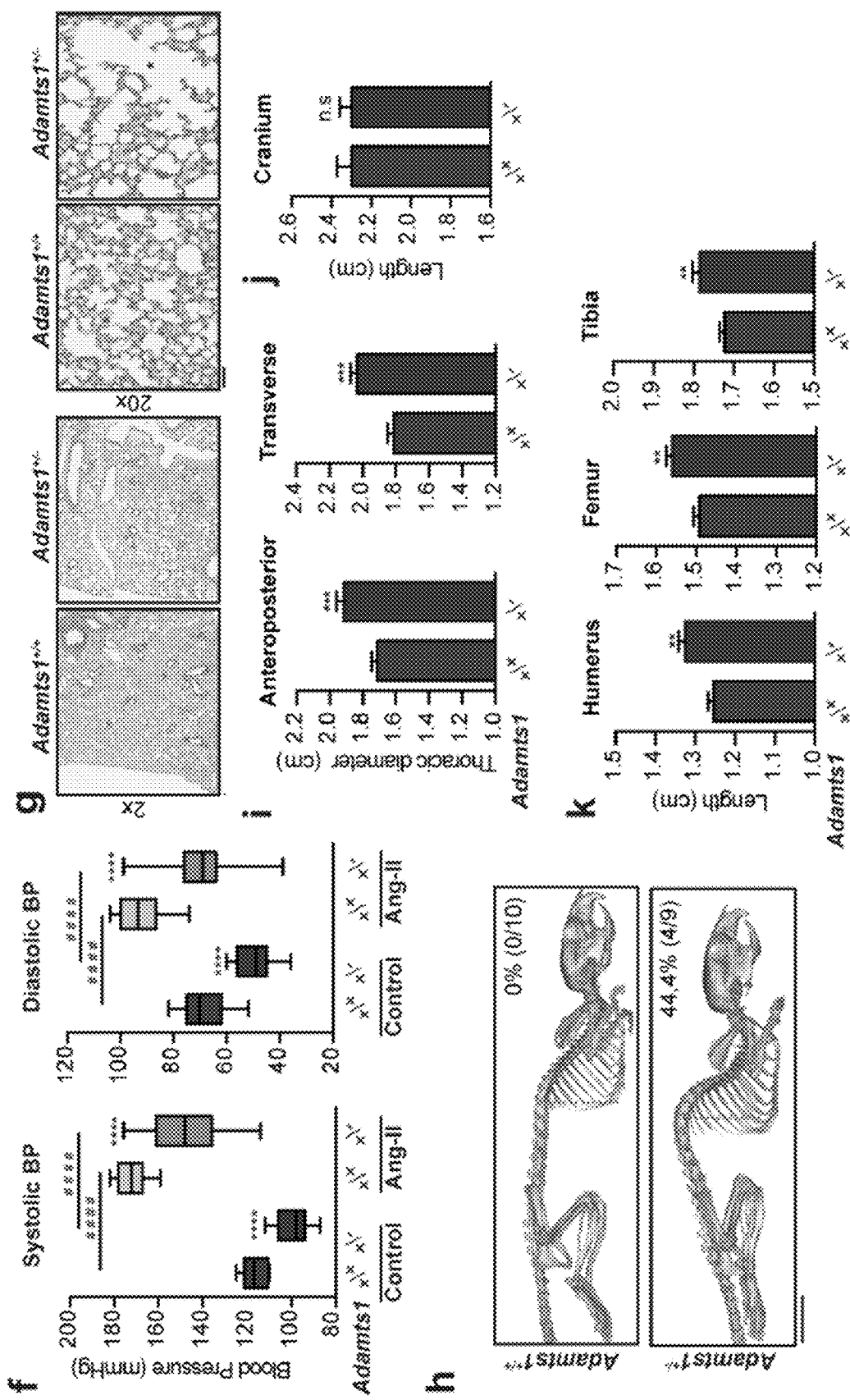

To investigate the contribution of Adamts1 to Ang-II-elicited aortic dilation and aneurysm, we used Adamts1 deficient mice from the European Mouse Mutant Archive (EM: 02291). Adamts1+/− mice expressed lower levels of aortic Adamts1 than wild-type (wt) littermates (FIGS. 1A and 7A). Adamts1−/− mice were not used because of their very low survival at weaning (FIG. 7B). In contrast, Adamts1+/− survival was similar to that of wt littermates, and these mice appeared healthy at this stage. Treatment of 8-week-old wt mice with Ang-II for 28 days promoted generalized aortic dilation, confirmed by ultrasonography of the aortic ring (AR), ascending aorta (AsAo) and abdominal aorta (AbAo) (FIGS. 1B-1C). Unexpectedly, inactivation of 1 Adamts1 allele induced aortic dilation in untreated mice, and this effect was exacerbated by Ang-II (FIGS. 1B-1C). In addition, whereas Ang-II barely induced AA or lethal aortic dissections in wt mice, it readily triggered their formation in Adamts1+/− mice (FIGS. 1D-1E). No aneurysms or lethal dissections were detected in Adamts1+/− mice in the absence of Ang-II at this age. Since Ang-II induces hypertension, we investigated whether Adamts1 inactivation had a similar effect. We found that, unlike Ang-II, Adamts1 gene dose reduction decreased systolic and diastolic blood pressure (BP) (FIG. 1F), suggesting that Ang-II and Adamts1 haploinsufficiency might induce aortic dilation through separate mechanisms.

In line with developmental kidney abnormalities in other Adamts1-targeted mice, the kidneys of our Adamts1+/− mice had an enlarged caliceal space, indicating hydronephrosis (FIG. 7C). However, plasma urea and creatinine were similar in wt and heterozygous mice (FIGS. 7D-7E), suggesting that renal function was not compromised.

The presence of renal abnormalities suggested that the aortic pathology induced by Adamts1 deficiency might be syndromic. Syndromic aortic conditions in humans and mice, including MFS, involve alterations to the lungs and the skeleton. Examination of 3-month-old Adamts1+/− mice revealed a marked increase in distal airspace caliber, characteristic of emphysema (FIG. 1G). Significant kyphosis was detected in 44.4% of 3-4-month-old Adamts1+/− mice (FIG. 1H). This was associated with increased anterioposterior and transverse diameters of the chest due to overgrowth of the ribs (FIG. 1I). Other long bones (humerus, tibia and femur) were also longer in sex-matched Adamts1+/− mice, whereas cranial size and morphology showed no between-genotype differences (FIGS. 1J-1K).

Example 3. Aortic Adamts1 Knockdown Promotes TAA

Figure 2:
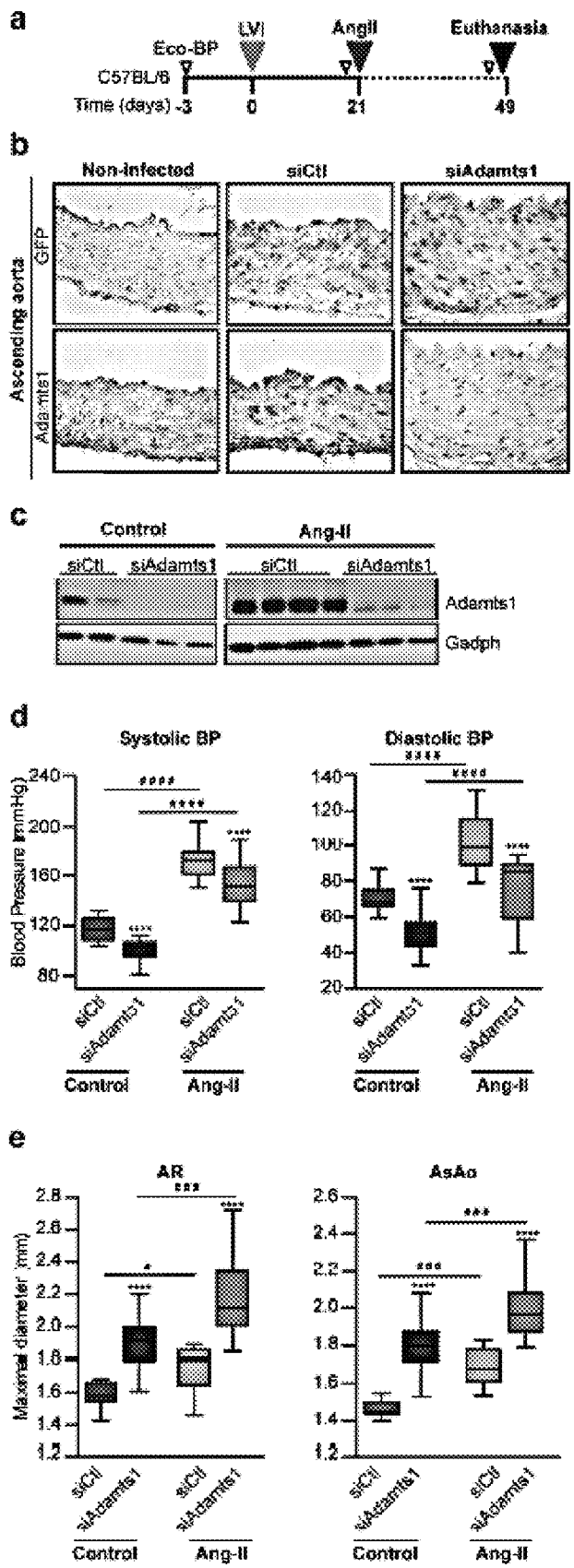
FIG. 2. Adamts1 knockdown in the aorta of adult mice causes an aortic disease similar to that induced by Adamts1 genetic deficiency. Eight-week-old C57BL/6 mice were inoculated through the jugular vein with lentivirus expressing GFP and either siCtl or siAdamts1. (a) Experimental timeline. White triangle, Eco-BP: ultrasound and BP analysis; LVi, lentivirus inoculation; Ang II, Ang-II minipump implantation. (b) Representative GFP and Adamts1 immunostaining on AsAo sections. Scale bar, 50 µm. (c) Adamts1 immunoblot analysis in aortic samples from mice transduced and treated as indicated. Gapdh expression was used as a loading control. End-of-treatment (d) systolic and diastolic BP (mean±SEM) and maximal aortic diameter (mean±SEM) in 12 control siCtl, 16 control siAdamts1, 13 Ang-II siCtl, and 16 Ang-II siAdamts1 mice. One-way ANOVA, **p<0.001 siCtl vs siAdamts1; #p<0.05, ###p<0.001, and ####p<0.0001, control vs Ang-II. Results in D-E are pooled data from two independent experiments. (f) Images show Masson's trichrome (Masson T.), elastic van Gieson (EVG) and alcian blue staining. Scale bar, 50 µm. (g,h) Quantification of elastin breaks and collagen content in AsAo sections from the mouse cohorts shown in FIGS. 1 and 2d-2e. One-way ANOVA, p<0.01, *p<0.001, **p<0.0001 siCtl vs siAdamts1 or Adamts1+/+ vs Adamts1+/−; #p<0.05, ##p<0.01, ####p<0.0001 Control vs Ang-II. (i) Representative TGFβ1, pSMAD2 and total SMAD2/3 immunohistochemistry of AsAo sections from Control or Ang-II-treated Adamts1+/+ and Adamts1+/− mice (n=3).
Figure 2:
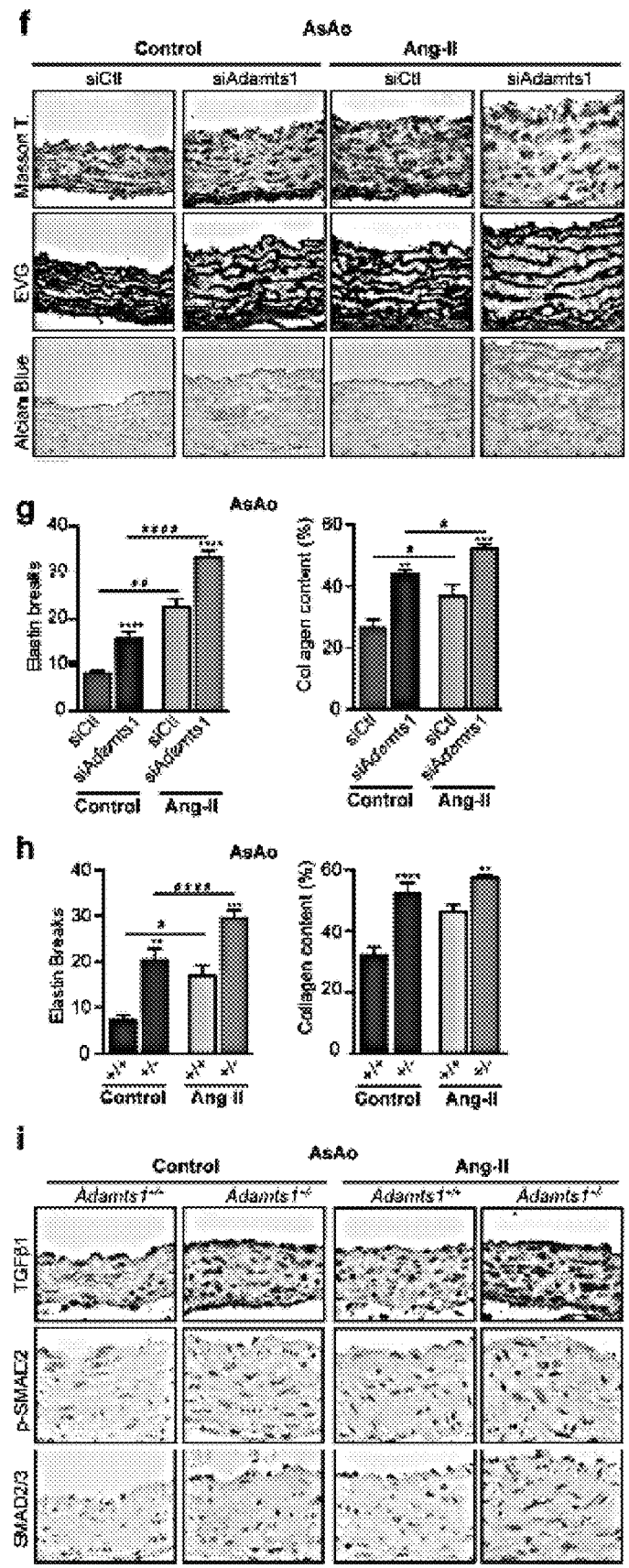

To investigate the direct effects of Adamts1 depletion on aortic dilation, we knocked down aortic expression in adult mice by transducing the aortic wall with lentivirus encoding Adamts1 specific siRNA. A screen of Adamts1 siRNAs in cultured VSMCs identified the high silencing capacity of siRNA-27 (FIGS. 8A-8B). Lentiviral-driven co-expression of green fluorescent protein (GFP) facilitated assessment of transduction efficiency. Intra-jugular inoculation of lentivirus into C57BL/6 mice yielded efficient and steady transduction of all aortic wall layers, determined by GFP immunostaining of the AsAo and AbAo aorta 7 weeks later (FIGS. 2A-2B). The expression of Adamts1 was almost undetectable in aortic samples of mice inoculated with lentivirus encoding siRNA-27 (siAdamts1) (FIGS. 2B-2C), even in mice treated with Ang-II for the last 4 weeks (FIGS. 2C and 8C). Indeed, Adamts1 mRNA levels in aortic samples of transduced mice were below those in Adamts1+/− aorta (FIG. 8D). Adamts1 silencing was confirmed in all layers of the AsAo and AbAo (FIG. 2B). Consistent with the data from Adamts1+/− mice, aortic Adamts1 silencing in adult aorta decreased systolic and diastolic BP (FIG. 2D) and induced strong dilation of the AR, AsAo, and AbAo that was further increased by treatment with Ang-II (FIG. 2E).

Example 4. Medial Degeneration and Activation of the TGFβ Pathway in the Aortic Wall of Adamts1 Deficient Mice Histologic analysis of AsAo and the AbAo revealed that reduction of Adamts1 levels, by lentiviral transduction or genetic inactivation, caused the characteristic features of medial degeneration: aortic wall thickening, elastic-fiber fragmentation and disarray, excessive collagen deposition, and proteoglycan accumulation (FIGS. 2F-2H and 9A-9E). These features were exacerbated by Ang-II (FIGS. 2F-2H and 9A-9E).

Aortic medial degeneration in Marfan and Loeys-Dietz syndromes is linked to activation of the TGFβ pathway. Immunohistochemistry of aortic sections from Adamts1+/− mice revealed increased TGFβ 1 and Smad2/3 expression (FIG. 2I) and increased Smad2 activation, determined by elevated phosphorylation and nuclear location (FIG. 2I). Similar results were found in Adamts1 knock-down mice (FIG. 10A). Consistently, aortas of Adamts1+/− and siAdamts1-inoculated mice had elevated mRNA levels of the TGFβ transcriptional targets Ctgf, Col1a1, and Pai-1 (FIG. 10B and FIG. 10C).

Example 5. Aortic Dilation Induced by Adamts1 Deficiency is Fast and Independent of TGFβ

Figure 3:
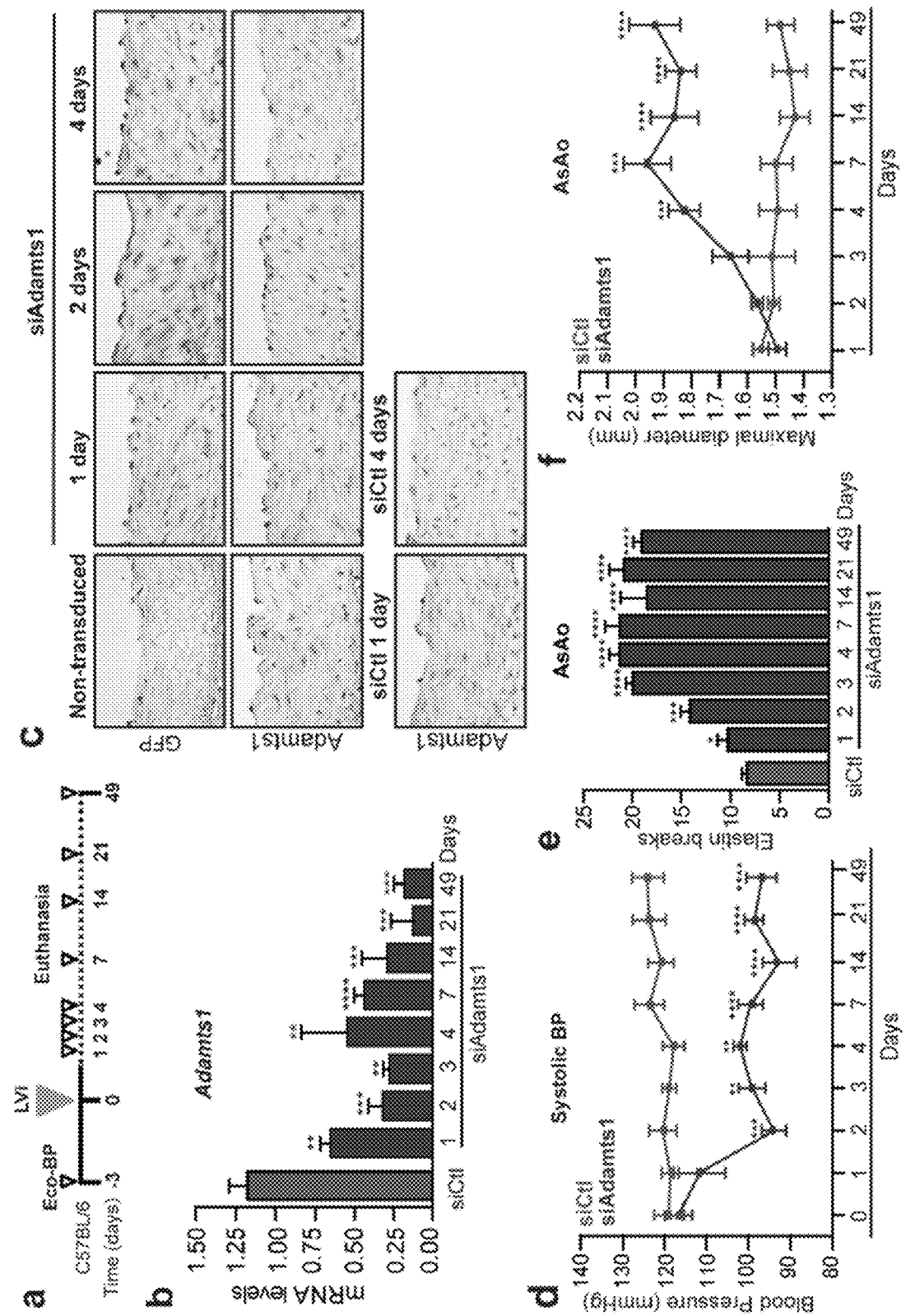
FIG. 3. Adamts1 knockdown rapidly induces aortic dilation, hypotension and medial degeneration independently of TGFβ activation. (a) Experimental timeline. Eight-week-old C57BL/6 mice were inoculated through the jugular vein with siCtl or siAdamts1 lentivirus and monitored for aortic dilation and BP at the indicated times. Adamts1 expression analyzed in aortic extracts by (b) RT-qPCR and (c) immunohistochemistry. Representative images are shown of Adamts1 and GFP in AsAo sections. mRNA amounts were normalized to Gapdh expression (means±SEM). One-way ANOVA, **p<0.001, *p<0.001, **p<0.0001 vs siCtl. Scale bar, 50 µm. (d) Systolic BP; (e) elastin breaks; maximal diameter of (f) AsAo and (g) AbAo; and (h) collagen content (mean±SEM; n=5-12) at the indicated times in mice transduced with siCtrl or siAdamts1 lentivirus. (e,h) One-way ANOVA and (d,e,g) two-way ANOVA, p<0.001, **p<0.0001 vs siCtl at the same time-point. (i) Representative zymogram analysis of Mmp2 and Mmp9 activity in aortic extracts prepared 4 days after transduction of mice with siCtl or siAdamts1 (n=3). (j) Experimental scheme. One group of animals received intraperitoneal injection of a neutralizing anti-TGFβ antibody 3 days before lentivirus inoculation, and injections were repeated 3 times per week. Another group was treated with losartan by osmotic minipump delivery beginning immediately before lentivirus inoculation. (k) Changes in maximal AsAo diameter and end-of-experiment quantification of (l) elastin breaks and (m) collagen content in aortic sections in the indicated experimental groups (mean±SEM). Numbers of mice per group were 8 siCtrl, 4 siCtrl losartan, 5 siAdamts1, 7 siAdamts1 losartan, and 6 siAdamts1 anti-TGFβ. (k) Two-way ANOVA of group means and (l,m) one-way ANOVA, p<0.001, *p<0.001, **p<0.0001 vs si-Ctl; n.s., non-significant. (b,e,h) siCtl results were stable throughout the experimental period, and data are means of readings at 2, 4, 7, 14, 21, and 49 days. (n) Representative images of Mmp9 (red), SMA (white), and F4/80 (green) immunofluorescence, elastin autofluorescence (green) and DAPI-stained nuclei (blue) in aortic sections from mice 4 d after inoculation with siCtl-expressing or siAdamts1-expressing lentivirus. Atheroma plaques in Apoe−/− mice that were fed a high-fat diet were used as a positive control for F4/80 staining. Scale bar,50 µm.
Figure 3:
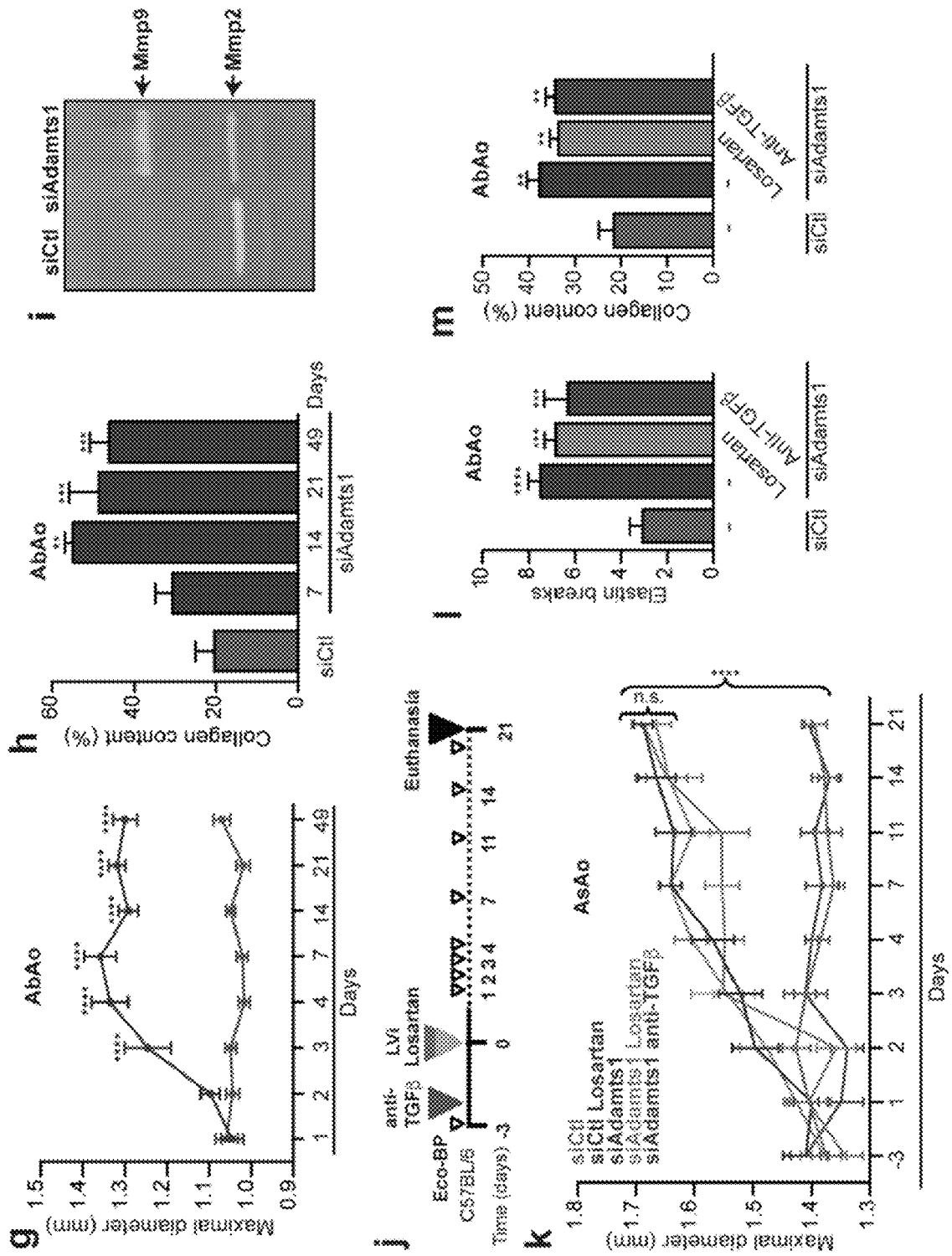
Figure 3:
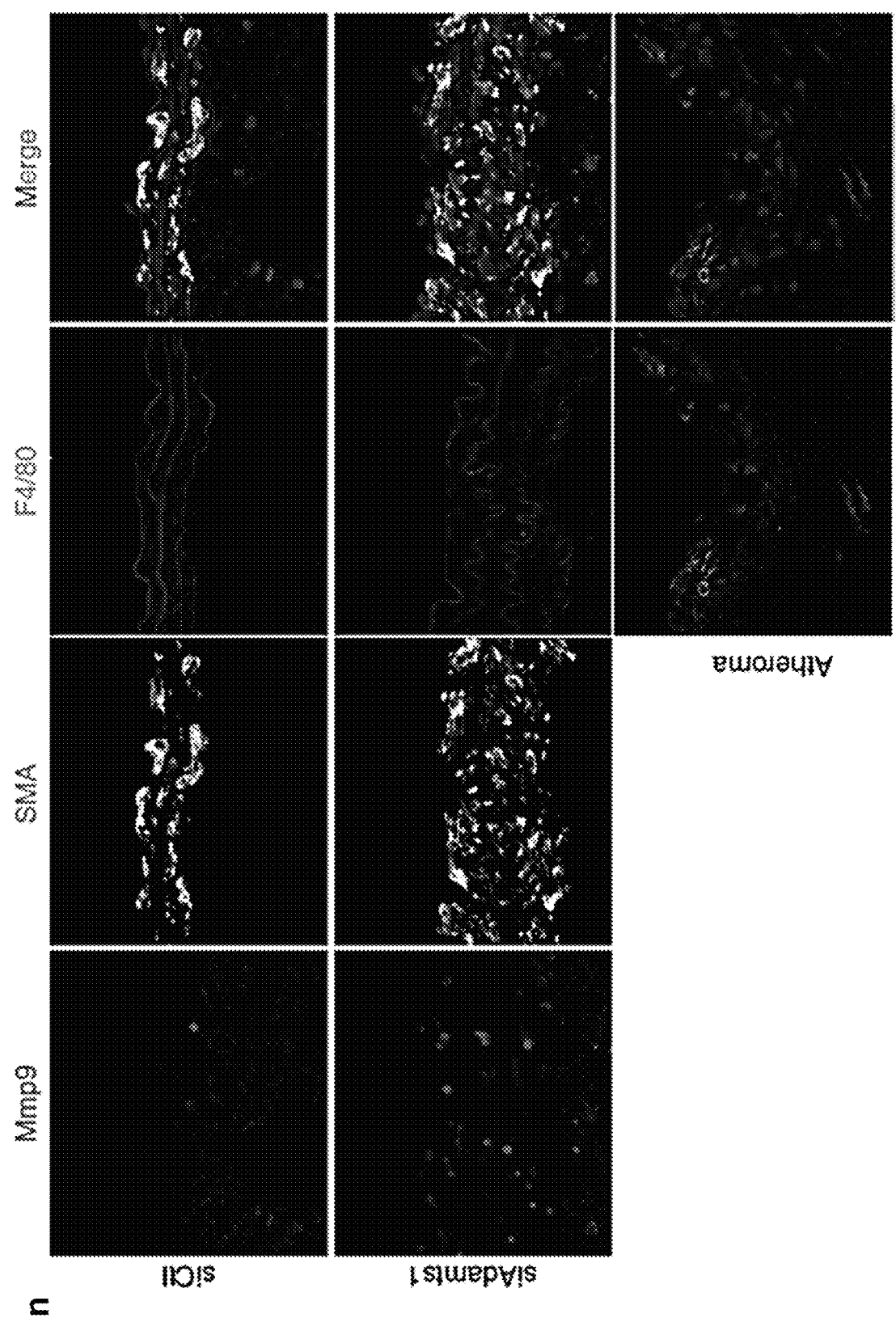

To assess the pathogenesis of Adamts1-deficiency-dependent aortopathy, we monitored AsAo and AbAo diameter and BP after intrajugular inoculation of siCtl or siAdamts1 lentiviruses (FIG. 3A). Reduced Adamts1 mRNA and protein levels were detected from as early as 1-2 days post-inoculation (FIGS. 3B-3C), coinciding with the first drop in systolic and diastolic BP and the induction of elastolysis (FIGS. 3D-3E and 11A-11B). However, AsAo and AbAo diameter did not increase significantly until 2-3 days post-inoculation (FIGS. 3F-3G). These events preceded collagen deposition in the aortic wall (FIG. 3H) and transcriptional activation of the TGFβ pathway, which began 1-2 weeks post-inoculation (FIG. 11C). The early induction of elastolysis prompted us to assess the activity of Mmp2 and Mmp9, major elastolytic proteins in the aortic wall. Activity of Mmp9, but not Mmp2, was rapidly and markedly induced after Adamts1 silencing (FIG. 3I).

Canonical and non-canonical pathways of TGFβ activation play critical roles in a mouse model of MFS, and a TGFβ-neutralizing antibody and the AT1R antagonist losartan can both prevent aneurysm formation in this model. Although the timing of TGFβ activation after Adamts1 silencing suggested a secondary role in aortopathy onset, we used losartan and a TGFβ-neutralizing antibody to assess the contribution of the TGFβ pathway (FIG. 3J). Strikingly, neither treatment inhibited aortic dilation induced by siAdamts1 (FIGS. 3K and 11D). Moreover, these treatments did not prevent hypotension (FIG. 11E) and did not reduce elastic fiber fragmentation or fibrosis (FIGS. 3L-3M). Detection of mRNA levels of TGFβ transcriptional targets, as surrogate molecular readouts of treatment efficacy, showed that the TGFβ antibody efficiently inhibited induction of Tgfb1, Pai-I, Ctgf, and Col1a1 (FIG. 11F). These results indicate that the neutralizing antibody worked efficiently and that fibrosis is independent of TGFβ activation during disease onset. Losartan, as expected, reduced BP in control mice (FIG. 11E). These results support the conclusion that TGFβ pathway activation is secondary to aortic dilation and elastolysis in Adamts1-related aortopathy.

Example 6. Nos2-Derived Nitric Oxide Mediates the Aortopathy Induced by Adamts1 Deficiency To further investigate the mechanism of Adamts1-related aortopathy, we focused on potential mediators of hypotension, the earliest effect detected upon Adamts1 silencing. A candidate factor is nitric oxide (NO), an endogenous vasorelaxant that relaxes smooth muscle and lowers BP. NO can be produced by constitutively expressed NO synthase (NOS) of endothelial (eNOS, NOS3) or neuronal (nNOS, NOS1) origin or by inducible NOS (iNOS, NOS2). To test the contribution of NO to the induction of aortic dilation, we treated C57BL/6 mice with N□-nitro-L-arginine-methylesther (L-NAME), an inhibitor of all NOS enzymes (FIG. 4A). Despite the hypertensive effect of L-NAME (FIG. 12A), it prevented siAdamts1-induced dilation of the AsAo and the AbAo (FIG. 4B), blocked elastolysis (FIGS. 4C and 12B), decreased the fibrosis (FIG. 4D) and prevented Mmp9 activation (FIG. 4E).

To determine the therapeutic potential of NOS activity inhibition, we used L-NAME to treat Adamts1+/− mice. L-NAME rapidly decreased AsAo and AbAo diameter to normal levels (FIG. 4F), reverted the systolic and diastolic hypotension (FIGS. 4G and 12C), decreased elastic fiber fragmentation (FIG. 4H), and diminished fibrosis (FIG. 4I).

Under physiological conditions, vascular NOS3 produces low levels of NO to maintain vascular homeostasis, whereas under pathological conditions NOS2 can be transcriptionally activated and produce 1000-fold more NO than its constitutive counterparts. We therefore hypothesized that Nos2 levels might be increased in Adamts1 deficient mice and mediate aortic dilation and medial degeneration. Nos2 expression was significantly induced as early as 2 days after siAdamts1 inoculation (FIG. 5A), whereas Nos3 was unaffected (FIG. 13A). Endothelin-1, another BP regulator, was not affected by Adamts1 silencing (FIG. 13B). Immunostaining of aortic cross sections from siAdamts1 and Adamts1+/− mice confirmed increased Nos2 levels (FIG. 5B).

To investigate whether Nos2-derived NO mediates the aortopathy induced by Adamts1 deficiency, we inoculated Nos2−/− and wt mice with siAdamts1 lentivirus (FIG. 5C). Nos2-deficiency blocked siAdamts1-induced AsAo and AbAo dilation (FIG. 5D), elastic fiber fragmentation (FIG. 5E) and fibrosis (FIG. 5F). Nos2−/− mice were normotensive and Adamts1 silencing failed to decrease their systolic and diastolic BP (FIGS. 5G and 13D). Consistent with a critical role for Nos2-derived NO in Adamts1-deficiency-induced aortopathy, unfixed sections of siAdamts1-transduced aorta contained higher NO levels than sections from control mice (FIG. 5H). Similarly, NO levels were higher in unfixed sections of Adamts1+/− aorta than in those from wt mice (FIG. 5H). NO did not accumulate in aortic sections of Nos2−/− mice inoculated with siAdamts1 (FIG. 5H).

Example 7. Nitric Oxide and Adamts1 Play a Critical Role in Marfan Syndrome

We hypothesized that NO might mediate medial degeneration in other syndromic forms of TAA. To determine the role of NO in MFS, we administered L-NAME to mice heterozygous for an Fbn1 allele including a cysteine substitution (C1039G), equivalent to a mutation frequent in MFS patients (FIG. 6A). The Fbn1C1039G/+ phenotype resembles human MFS, including thoracic aortic dilation, aneurysm and dissection, and histological features of aortic medial degeneration. Similar to Adamts1-deficient mice, 12-week-old Fbn1C1039G/+ mice exhibited dilation of the AsAo and AbAo (FIGS. 6B and 14A). L-NAME rapidly decreased the AsAo and AbAo diameters to normal levels (FIGS. 6B and 14A), augmented the systolic and diastolic BP (FIGS. 6C and 14b), and diminished elastic fiber fragmentation (FIGS. 6C and 14C). Fbn1C1039G/+ mice showed no significant collagen accumulation, and collagen content was unaffected by L-NAME (FIG. 14D). Fbn1C1039G/+ mice also exhibited markedly elevated levels of Nos2 and NO production relative to littermate controls, while Nos3 was unaffected (FIG. 6E).

These similarities suggested a link between Adamts1 and the aortic pathology of Fbn1C1039G/+ mice. Immunostaining of Fbn1C1039G/+ aortic sections revealed reduced levels of Adamts1, confirmed by immunoblot analysis of aortic protein extracts (FIG. 6G). However, Adamts1 mRNA levels were similar in Fbn1C1039G/+ mice and control littermates (FIG. 14E), suggesting posttranscriptional downregulation of Adamts1 expression in Marfan syndrome.

Assessment of the contribution of ADAMTS1 and NOS2 to human MFS revealed depressed ADAMTS1 expression in the medial layer of aortic sections from MFS patients compared with aortas from organ transplant donors, regardless of sex and age (FIGS. 6H and 14F). Quantification of the ADAMTS1-positive area in immunohistochemistry-stained sections confirmed a sharp expression decrease in MFS samples (FIG. 6I). Elastin autofluorescence was barely detected in MFS aortic sections and showed a disorganized pattern. NOS2 immunofluorescence revealed higher expression in the medial layer of 6 out of 8 MFS aortic sections (FIGS. 6J and 14G) and quantification of NOS2-positive area in these sections showed a marked increase in MFS samples (FIG. 6K). Together, these data support the notion that ADAMTS1 and NOS2 might be important mediators of the aortic pathology in human MFS (FIG. 6L).

Example 8. Docking of Human NOS2 and Interaction with Inhibitors

Fasta sequences of oxigenase domain of human NOS2 protein (Uniprot Id: P35228, residues 511-1153) and reductase domain (Uniprot Id: P35228, residues 1-535) were submitted to a local implementation of I-Tasser software suite v5.0 (1) for modeling with homology. For each one, the best model with minimal energy and correct folding (best structural alignment to template: PDB ID 4nos and 3hr4 respectively) was selected as final template. The overlapping region of both templates (residues 511-535) was structural aligned using the pymol program (The PyMOL Molecular Graphics System, Version 1.8, www.pymol.org) to produce a final full monomer template for close loop using the loop-model tool of Rosetta suite v3.6 release (www.rosettacommons.org). The model with less score, but high energy yet, was selected as final template for refinement using the relax tool of Rosetta suite v3.6 (www.rosettacommons.org) to obtain the final monomeric model.

Two truncated forms (residues 83-1153) of the previous model were structural aligned to the PDB ID 4cx7 structure to make a template for docking the NOS2 dimer using the docking tool of Rosetta suite v3.6 (www.rosettacommons.org). The best model (minimal energy with correct structural alignment to 4cx7) was selected as final homodimer model with the ligands hemo, H4B and Arg fixed from the 4cx7 structure (FIG. 18a-b)

For in-silico docking of the NOS2 dimer with inhibitors, default 3D structure for each ligand L-NAME, 1400W, Aminoguanidine, GW273629, L-NIL and Clotrimazole were obtained from PubChem (pubchem.ncbi.nlm.nih.gov) and 100 conformers for each one were produced using the Frog2 web tool. The centroid coordinates of the default conformer for each inhibitor was located in the centroid coordinates of the guanidine site in both chains to make a initial template for docking the final model of the NOS2 with inhibitors using the ligand docking tool of the of Rosetta suite v3.6 release (www.rosettacommons.org). As before, the model with less score, but high energy yet, was selected as final template for refinement using the relax tool of Rosetta suite v3.6 (www.rosettacommons.org) to obtain the final model.

TABLE

| Predicted energy of the ligand interface for complex NOS2-inhibitor. | |
|---|---|
| Interface ΔΔG | Inhibitor |
| −8.431 | L-NAME |
| −5.880 | 1400W |
| −8.238 | Aminoguanidine |
| −7.296 | GW273629 |
| −7.833 | L-NIL |
| −8.497 | Clotrimazole |

All the inhibitors models bind in the guanidine site of the ligand region and have minor energy in the ligand interface region than the canonical NOS2/L-Arginine complex, suggesting more stable complex NOS2-inhibitor than the normal complex with L-Arginine ligand. This suggests that the inhibitors might displace and substitute the Arg normal ligand. Values shown as Rosetta suite internal units.

The invention claimed is:

1. A method for therapeutic treatment of a thoracic aortic aneurysm (TAA) in a patient in need thereof, comprising administering a composition comprising an iNOS inhibitor to the patient, wherein the iNOS inhibitor is selected from the group consisting of 1400W, L-NAME, GW274150, GW273629, Aminoguanidine (AG) hydrochloride L-NIL and clotrimazale.

2. The method according to claim 1, wherein the patient is suffering from a disease selected from the group consisting of: bicuspid aortic valve; a syndromic thoracic aortic aneurysm (TAA) and a non-syndromic TAA.

3. The method according to claim 1, wherein the patient is suffering from a syndromic thoracic aortic aneurysm (TAA).

4. The method according to claim 1, wherein the patient is suffering from Marfan syndrome (MFS).

5. The method according to claim 1, wherein the patient is a human patient.

6. The method of claim 1, wherein the patient is suffering from a disease associated with an aorthopathy triggered by Adamts1 deficiency.

7. The method of claim 2, wherein the TAA is Marfan Syndrome, vascular Ehlers Danlos, Loeys Dietz Syndrome Type 1, Loeys Dietz Syndrome Type 2 or Familial thoracic aortic aneurysm and dissection (familial TAAD).

8. The method of claim 3, wherein the TAA is Marfan Syndrome, vascular Ehlers Danlos, Loeys Dietz Syndrome Type 1, Loeys Dietz Syndrome Type 2 or Familial thoracic aortic aneurysm and dissection (familial TAAD).

9. The method of claim 1, wherein the patient is suffering from Marfan syndrome (MFS) and wherein the iNOS inhibitor is GW274150.

10. The method of claim 1, wherein the patient is suffering from a non-syndromic TAA.

11. The method of claim 10, wherein the TAA is Marfan Syndrome, vascular Ehlers Danlos, Loeys Dietz Syndrome Type 1, Loeys Dietz Syndrome Type 2 or Familial thoracic aortic aneurysm and dissection (familial TAAD).

12. The method of claim 1, wherein the method reduces the risk of aortic dissection or rupture in the patient.

* * * * *